(12) United States Patent
Cicortas Gunnarsson et al.

(10) Patent No.: US 8,637,017 B2
(45) Date of Patent: Jan. 28, 2014

(54) ANTI-EPCAM ANTIBODIES

(75) Inventors: Lavinia Diana Cicortas Gunnarsson, Oslo (NO); Didrik Paus, Oslo (NO); Jenny Margareta Karlsson, Oslo (NO); Remko Albert Griep, Slemmestad (NO); Sergej Michailovic Kiprijanov, Oslo (NO)

(73) Assignee: Affitech Research AS, Oslo (NO)

( * ) Notice: Subject to any disclaimer, the term of this patent is extended or adjusted under 35 U.S.C. 154(b) by 499 days.

(21) Appl. No.: 12/797,052

(22) Filed: Jun. 9, 2010

(65) Prior Publication Data

US 2010/0310463 A1 Dec. 9, 2010

Related U.S. Application Data

(60) Provisional application No. 61/185,387, filed on Jun. 9, 2009.

(30) Foreign Application Priority Data

Jun. 9, 2009 (GB) .................................. 0909904.5

(51) Int. Cl.
*A61K 39/395* (2006.01)
(52) U.S. Cl.
USPC ..................................... 424/133.1; 530/387.1
(58) Field of Classification Search
None
See application file for complete search history.

(56) References Cited

U.S. PATENT DOCUMENTS

| 7,227,002 | B1 | 6/2007 | Kufer et al. |
| 2005/0009027 | A1 | 1/2005 | Krupp et al. |
| 2005/0106722 | A1 | 5/2005 | Jones et al. |

FOREIGN PATENT DOCUMENTS

| WO | 9846645 A2 | 10/1998 |
| WO | 0069914 A2 | 11/2000 |
| WO | 0148485 A2 | 7/2001 |

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Lutterbuese, Petra, et al., "Exchanging human Fc gamma 1 with murine Fc gamma 2a highly potentiates anti-tumor activity of anti-EpCAM antibody adecatumumab in a syngeneic mouse lung metastasis model" Cancer Immunol. Immunother., 56, (2007), 459-68.
Prang, N, et al., "Cellular and complement-dependent cytotoxicity of Ep-CAM-specific monoclonal antibody MT201 against breast cancer cell lines" BJ Cancer, 92, (2005), 342-9.
Raum, Tobais, et al., "Anti-self antibodies selected from a human IgD heavy chain repertoire: A novel approach to generate therapeutic human antibodies against tumor-associated differentiation antigens" Cancer Immunol. Immunother., 50, (2001), 141-50.
Beiboer, Sigrid H.W., et al., "Guided selection of a pan carcinoma specific antibody reveals similar binding characteristics yet structural divergence between the original murine antibody and its human equivalent" J. Mol. Biol., 296, (2000), 833-49.
Di Paolo, Claudio, et al., "A Recombinant Immunotoxin Derived from a Humanized Epithelial Cell Adhesion Molecule-specific Single-chain Antibody Fragment Has Potent and Selective Antitumor Activity" Clin. Cancer Res., 9, (2003), 2837-48.
Davies, Julian & Riechmann, Lutz, "Affinity improvement of single antibody VH domains: residues in all three hypervariable regions affect antigen binding", Immunotechnology, 2, (1996), 169-79.
Kirman, Irena & Whelan, Richard L. "Drug evaluation: Adecatumumab, an engineered human anti-EpCAM antibody", Curr. Opin. Mol. Ther., 9, (2007), 190-6.
Willuda, Jorg, et al., "High Thermal Stability Is Essential for Tumor targeting of Antibody Fragments: Engineering of a Humanized Anti-epithelial Glycoprotein-2 (Epithelial Cell Adhesion Molecule) Single-Chain Fv Fragment", Cancer Res., 59, (1999), 5758-67.
Munz, Markus et al., "The carcinoma-associated antigen EpCAM upregulates c-myc and induces cell proliferation", Oncogene, 23, (2004), 5748-58.
Went, P., et al., "Frequent high-level expression of the immunotherapeutic target Ep-CAM in colon, stomach, prostate and lung cancers", Br. J. Cancer, 94, (2006),128-35.
Spizzo, Gilbert, et al., "High Ep-CAM expression is associated with poor prognosis in node-positive breast cancer", Breast Cancer Res. Treat., 86, (2004), 207-13.
Spizzo, Gilbert, et al., "Overexpression of epithelial cell adhesion molecule (Ep-CAM) is an independent prognostic marker for reduced survival of patients with epithelial ovarian cancer", Gynecol. Oncol., 103, (2006), 483-8.
Varga, Meri, et al., "Overexpression of epithelial cell adhesion molecule antigen in gallbladder carcinoma is an independent marker for poor survival", Clin. Cancer Res., 10, (2004), 3131-6.
O'Brien, et al., "A human colon cancer cell capable of initiating tumour growth in immunodeficient mice", Nature, 445, (2007), 106-10.
Marhaba, Rachid, et al., "CD44 and EpCAM: cancer-initiating cell markers", Curr. Mol. Med., 8, (2008), 784-804.

(Continued)

*Primary Examiner* — Laura B Goddard
*Assistant Examiner* — Meera Natarajan
(74) *Attorney, Agent, or Firm* — Rothwell, Figg, Ernst & Manbeck, p.c.

(57) ABSTRACT

Disclosed are antibodies that bind to Epithelial Cell Adhesion Molecule (EpCAM) and display certain advantages over known antibodies which bind to EpCAM, for example, the antibodies of the invention show good affinity, good cross-reactivity profiles and excellent ADCC and CDCC activity. Antibodies comprising specific heavy and light chain CDRs are disclosed. The invention thus relates to these antibodies and all uses thereof, in particular in the treatment of cancer. The present invention thus provides new antibody-based compositions, methods and combined protocols for treating cancer. Advantageous immunoconjugate compositions and methods using the new anti-EpCAM antibodies are also provided.

26 Claims, 17 Drawing Sheets

(56) References Cited

OTHER PUBLICATIONS

Baeuerle, P.A. & Gires, O. "EpCAM (CD326) finding its role in cancer", Br. J. Cancer, 96, (2007), 417-23.

Trzpis, M., et al., "EpCAM homologues exhibit epithelial-specific but different expression patterns in the kidney", Transgenic Res., 17, (2008), 229-38.

Roovers, R.C., et al, "High-affinity Recombinant phage antibodies to the pan-carcinoma marker epithetial glycoprotein-2 for tumour targetting" Br. J. Cancer, 78, (1998), 1407-16.

Naundorf, Stefanie, et al., "In vitro and in vivo activity of MT201, a fully human monoclonal antibody for pancarcinoma treatment" Int. J. Cancer, 100, (2002), 101-110.

Armstrong, Andrew & Eck, Stephen L. "EpCam: A new therapeutic target for an old cancer antigen", Cancer Biol. Ther., 2, (2003), 320-5.

Osta, Walid, et al., "EpCAM is overexpressed in breast cancer and is a potential target for breast cancer gene thereapy", Cancer Res., 64, (2004), 5818-24.

Velders, Markwin P., et al., "Immunotherapy with low and high affinity monoclonal antibodies 17-1A and 323/A3 in a nude mouse xenograft carcinoma model", Cancer Res., 55, (1995), 4398-4403.

Riethmuller, G., et al., "Randomised trial of monoclonal antibody for adjuvant therapy of resected Dukes' C colorectal carcinoma. German Cancer Aid 17-1A Study Group", Lancet, 343, (1994), 1177-83.

Punt, Cornelis J.A., et al., "Edrecolomab alone or in combination with fluorouracil and folinic acid in the adjuvant treatment of stage III colon cancer: a randomised study", Lancet, 360, (2002), 671-7.

Oberneder, Ralf, et al., "A phase I study with adecatumumab, a human antibody directed against epithelial cell adhesion molecule, in hormone refractory prostate cancer patients", Eur. J. Cancer, 42, (2006), 2530-8.

De Bono, Johann S., et al., "ING-1, a monoclonal antibody targeting Ep-CAM in patients with advanced adenocarcinomas", Clin. Cancer Res., 10, (2004), 7555-65.

Goel, S., et al., "Pharmacokinetic and safety study of subcutaneously administered weekly ING-1, a human engineered monoclonal antibody targeting human EpCAM, in patients with advanced solid tumors", Ann. Oncol., 18, (2007), 1704-7.

Connor, Joseph P., et al., "Ex vivo evaluation of anti-EpCAM immunocytokine huKS-IL2 in ovarian cancer", J. Immunother., 27, (2004), 211-9.

Ko, Yoo-Joung, et al, "Safety, pharmacokinetics, and biological pharmacodynamics of the immunocytokine EMD 273066 (huKS-IL2): results of a phase I trial in patients with prostate cancer", J Immunother., 27, (2004), 232-9.

Brischwein, K., et al., "MT110: A novel bispecific single-chain antibody construct with high efficacy in eradicating established tumors", Mol. Immunol., 43, (2006), 1129-43.

\* cited by examiner

Figure 1 scFv 3-17I Nucleotide sequence

<u>CCATGGCC</u>CAGGTCCAGCTGGTGCAGTCTGGGGCTGAGGTGAAGAAGCCTGGGTCCTCGGT
  NcoI    |---------V$_H$ Start (SEQ ID No.20 Start)

GAAGGTCTCCTGCAAGGCTTCTGGAGGCACCTTCAGCAGCTATGCTATCAGCTGGGTGCGA

CAGGCCCCTGGACAAGGGCTTGAGTGGATGGGAGGGATCATCCCTATCTTTGGTACAGCAA

ACTACGCACAGAAGTTCCAGGGCAGAGTCACGATTACCGCGGACGAATCCACGAGCACAGC

CTACATGGAGCTGAGCAGCCTGAGATCTGAGGACACGGCCGTGTATTACTGTGCGAGAGGC

CTTCTATGGAACTACTGGGGCCAGGGAACCCTGGTCACCGTCTCCTCA*AAGCTTTCAGGGA*
                                                V$_H$ End----   |--HindIII--Linker
*GTGCATCCGCCCCAAAACTTGAAGAAGGTGAATTTTCAGAAGC*<u>ACGCGT</u>AGAAATTGTAAT
Start                                      Linker End ------MluI-|------V$_L$ Start
  GACACAGTCTCCAGCCACCCTGTCTGTGTCTCCAGGGGAAAGAGCCACCCTCTCCTGCAGG

GCCAGTCAGAGTGTTAGCAGCAACTTAGCCTGGTACCAGCAGAAACCTGGCCAGGCTCCCA

GGCTCATCATCTATGGTGCATCCACCACGGCCTCTGGTATCCCAGCCAGGTTCAGTGCCAG

TGGGTCTGGGACAGACTTCACTCTCACCATCAGCAGCCTGCAGTCTGAAGATTTTGCAGTT

TATTACTGTCAGCAGTATAATAACTGGCCTCCGGCGTACACTTTTGGCCAGGGGACCAAGC
                                                                           (SEQ ID No. 20 End)-
TGGAGATCAAA<u>GCGGCCGC</u>
---V$_L$ End----|  NotI scFv 3-17I Amino acid sequence

QVQLVQSGAEVKKPGSSVKVSCKASGGTFSSYAISWVRQAPGQGLEWMGGIIPIFGTANYAQK
|---------V$_H$ Start (SEQ ID No.21 Start)
FQGRVTITADESTSTAYMELSSLRSEDTAVYYCARGLLWNYWGQGTLVTVSS*KLSGSASAPKL*
                                                                  V$_H$ End-|--------------
*EEGEFSEARV*EIVMTQSPATLSVSPGERATLSCRASQSVSSNLAWYQQKPGQAPRLIIYGAST
---Linker---|------V$_L$ Start
TASGIPARFSASGSGTDFTLTISSLQSEDFAVYYCQQYNNWPPAYTFGQGTKLEIK
                                   (SEQ ID No. 21 End)  V$_L$End------|

3-17I IgG

MT201 IgG

MOC31 IgG

Cell line: MDA-MB-453

Cell line: MDA-MB231

Cell line: BT-474

ANTI-EPCAM ANTIBODIES

This application claims priority from U.S. Provisional Application No. 61/185,387, filed Jun. 9, 2009 and GB Application No. 0909904.5, filed Jun. 9, 2009. These applications are incorporated herein by reference.

The invention relates to binding proteins which bind to Epithelial Cell Adhesion Molecule (EpCAM) and all uses thereof. In particular, the invention relates to antibodies or antibody fragments that bind to EpCAM and to methods of use thereof, including cancer treatment.

In the year 2000, an estimated 22 million people were suffering from cancer worldwide and 6.2 millions deaths were attributed to this class of diseases. Every year, there are over 10 million new cases and this estimate is expected to grow by 50% over the next 15 years (WHO, World Cancer Report. Bernard W. Stewart and Paul Kleihues, eds. IARC Press, Lyon, 2003). Cancer causes about 13% of all human deaths. According to the American Cancer Society, 7.6 million people died from cancer in the world during 2007.

The most common current cancer treatments are generally limited to invasive surgery, radiation therapy and chemotherapy, all of which cause either potentially severe side-effects, non-specific toxicity and/or traumatizing changes to ones body image and/or quality of life. Cancer can become refractory to chemotherapy reducing further treatment options and likelihood of success. Some cancers with a relatively high treatment success rate, such as breast cancer, also have a very high incidence rate and, thus, remain major killers.

There are many more examples of cancer where current treatments do not meet the needs of patients either due to their lack of efficacy and/or because they have high morbidity rates and severe side-effects. Thus, there is clearly a need for cancer treatments with better safety and efficacy profiles.

One of the causes for the inadequacy of many current cancer treatments is their lack of selectivity for affected tissues and cells. Surgical resection always involves the removal of apparently normal tissue as a "safety margin" which can increase morbidity and risk of complications. It also always removes some of the healthy tissue that may be interspersed with tumor cells and that could potentially maintain or restore the function of the affected organ or tissue. Radiation and chemotherapy will kill or damage many normal cells due to their non-specific mode of action. This can result in serious side-effects such as severe nausea, weight loss and reduced stamina, loss of hair etc., as well as increasing the risk of developing secondary cancer later in life. Treatment with greater selectivity for cancer cells would leave normal cells unharmed thus improving outcome, side-effect profile and quality of life.

The selectivity of cancer treatment can be improved by using antibodies that are specific for molecules present only or mostly on cancer cells or which are present in higher levels on cancer cells or overexpressed in cancer cells. Thus, immunotherapy treatments, e.g. involving antibodies, of various diseases, including cancer, are currently a very active field of research and development, and show much promise in terms of achieving successful therapeutic regimes. Such antibodies can be used to modulate the immune system and enhance the recognition and destruction of the cancer by the patient's own immune system.

Most antibodies tested to date have been raised against known cancer markers in the form of mouse monoclonal antibodies, sometimes "humanized" through molecular engineering. Unfortunately, these antibodies are mouse proteins that are being seen by the human patient's immune system as foreign proteins. The ensuing immune reaction and antibody response can result in a loss of efficacy or in side-effects.

EpCAM (CD326) is also referred as EGP-2, 17-1A, HEA125, MK-1, GA733-2, EGP34, KSA, TROP-1, ESA, TACSTD1 and KS1/4 and is one of the first identified tumor-associated antigens. The EpCAM antigen is unique in that it is not a member of any of the major families of adhesion molecules such as cadherins, selectins, or integrins. It is a type I membrane protein of 314 amino acids (aa) of which only 26 aa are facing the cytoplasm. EpCAM has been postulated to function as a homophilic cell adhesion molecule that interferes with cadherin-mediated cell-cell contact. EpCAM upregulates c-myc, cyclin A and E, promotes cell cycling and enhances cell proliferation (Munz et al., 2004, Oncogene 23: 5748-58).

EpCAM is abundantly and homogeneously expressed on human carcinomas of different origin (Went et al. 2006, Br J Cancer 94: 128-35). Immunohistochemical studies of prostate cancer and cervical intraepithelial neoplasia have shown that EpCAM expression can increase with disease progression and proliferation. This apparent overexpression has also been described in patients with invasive breast and ovarian cancers and was a strong predictor of poor disease-free and overall survival (Spizzo et al., 2004, Breast Cancer Res Treat 86: 207-13; Spizzo et al., 2006, Gynecol Oncol 103: 483-8). Similar correlations between EpCAM overexpression and disease progression could be observed in patients suffering from gallbladder carcinoma (Varga et al., 2004. Clin Cancer Res 10: 3131-6). Moreover, EpCAM is overexpressed cancer-initiating or cancer stem cells isolated from colon, breast, pancreas and prostate carcinomas (O'Brien et al., 2007, Nature 445: 106-10; Marhaba et al., 2008, Curr Mol Med 8: 784-804). These data impressively underscore the potential utility of EpCAM as an immunotherapeutic target for treatment of the most frequent human cancers.

EpCAM is also a validated target for carcinoma-directed immunotherapy. In this regard, a number of antibodies to EpCAM have been used in immunotherapy, although it should be noted that several of these have failed in clinical trials for various reasons. These EpCAM antibodies take a number of formats, including naked antibodies, immunotoxins and bi or tri-specific antibodies (Baeuerle and Gires, Br. J. Cancer, 2007, 96: 417-423).

Whilst a bi-specific antibody approach (e.g. as used by Micromet in the case of their MT110 antibody and by Trion Pharma in the case of Catumaxomab (Removab®)) has some advantages, it is also highly desirable to develop antibodies which can have a therapeutic effect in a monospecific format, i.e. in a format in which only one antibody specificity is present. Equally, as the mechanism of action of a bi- or tri-specific antibody is fundamentally different from that of a monospecific format, direct comparison is simply not possible or relevant.

Another format of EpCAM antibody which has been used in clinical trials is an immunotoxin format (e.g. as used by Viventia in the case of Proxinium™/Vicinium™), i.e. where an antibody moiety is conjugated to a toxic molecule to effect tumor cell killing. Proxinium™/Vicinium™ is a fusion protein of humanized scFv (MOC31 derived) and *Pseudomonas* exotoxin (Di Paolo et al., 2003, Clin Cancer Res 9: 2837-48). Although this antibody has shown some encouraging results in the clinic, due to immunogenic side effects systemic administration is not possible and direct/local administration to the tumor site is required. Again, as the mechanism of action of an immunotoxin is fundamentally different from that of a naked antibody, direct comparison is not really possible or relevant.

The most effective naked format anti EpCAM antibody currently in clinical trials is MT201 (Adecatumumab, developed by Micromet, Inc. and out-licensed to Merck Serono), which is fully human IgG1 monoclonal antibody. This antibody has shown some promising results in phase I and II clinical trials in prostate and metastatic breast cancer and, unlike the case with some other naked EpCAM antibodies (e.g. ING-1, a high affinity human engineered IgG1 of Xoma, Inc.) to date patients have shown no signs of pancreatitis. Other trialled anti EpCAM antibodies have shown clinical disadvantages. For example, despite having a benign safety profile, Edrecolomab (17-1A; Panorex®), shows only borderline clinical activity and is rapidly neutralised by a human anti-mouse antibody (HAMA) response. MOC31 (a humanized version of which is being used by Viventia) is another anti-EpCAM antibody which has been studied extensively and is a chimeric antibody with mouse variable domains and human constant domains.

Since EpCAM is expressed on a wide range of normal epithelia, systemic intolerability of an EpCAM-specific immunotoxin (Proxinium™/Vicinium™) and trifunctional antibodies (Removab®), as well as acute pancreatitis, as seen with high-affinity anti-EpCAM MAb ING-1, appear consistent with a collateral damage of normal EpCAM-expressing tissue. On the other hand, edrecolomab (Panorex®) and adecatumumab (MT201) appear well tolerated and seemingly ignore most normal EpCAM-expressing tissues. Thus, the therapeutic potential of anti EpCAM antibodies is clear and the challenge is to develop anti EpCAM antibodies which show alternative or improved properties to those known in the art, in particular to the current apparent leader, MT201.

The present inventors have identified antibodies that bind to EpCAM and show improved properties over prior art antibodies, in particular over MT201 and MOC31 as described above. For example, the antibodies of the invention show good affinity, good cross-reactivity profiles and excellent ADCC and CDCC activity. In addition, preferably such antibodies are fully compatible with the patient's immune system by virtue of being fully-human proteins. The antibodies of the invention can be used for diagnostic or therapeutic uses (in particular for cancer) or as a basis for engineering other antibodies or binding molecules for the target antigen, EpCAM, such as bispecific antibodies, immunotoxins or antibody-drug conjugates (ADC).

Amino acid and/or DNA sequences of antibody molecules of the invention that bind to EpCAM, their $V_H$ and $V_L$ domains including complementarity determining regions (CDRs), are set forth in the various SEQ ID NOs. listed herein. All the specific antibodies described herein have the same CDRs in their VH domains but slightly different CDRs in their VL domains.

In one embodiment, the present invention provides an antibody that binds to EpCAM comprising a heavy (VH) chain CDR1 domain comprising the amino acid sequence of SEQ ID NO:5 or a sequence substantially homologous thereto.

Alternatively or in addition, in an embodiment of the invention, the antibody that binds to EpCAM comprises a heavy (VH) chain CDR2 domain comprising the amino acid sequence of SEQ ID NO:6 or a sequence substantially homologous thereto.

Alternatively or in addition, in an embodiment of the invention, the antibody that binds to EpCAM comprises a heavy (VH) chain CDR3 domain comprising the amino acid sequence of SEQ ID NO:7 or a sequence substantially homologous thereto. As the CDR3 domains of antibodies are often particularly important for antigen binding, the presence of such a VH CDR3 domain based on SEQ ID NO:7 is particularly preferred in the antibodies of the invention. Indeed, such a sequence is present in all the specific antibodies described herein.

Alternatively or in addition, in an embodiment of the invention, the antibody that binds to EpCAM comprises a light chain (VL) CDR1 domain comprising the amino acid sequence of SEQ ID NO:8 or a sequence substantially homologous thereto.

Alternatively or in addition, in an embodiment of the invention, the antibody that binds to EpCAM comprises a light chain (VL) CDR2 domain comprising the amino acid sequence of SEQ ID NO:9 or a sequence substantially homologous thereto. In an alternative embodiment of the invention, the antibody comprises a light chain (VL) CDR2 domain comprising the amino acid sequence of SEQ ID NO:29 or a sequence substantially homologous thereto.

Alternatively or in addition, in an embodiment of the invention, the antibody that binds to EpCAM comprises a light chain (VL) CDR3 domain comprising the amino acid sequence of SEQ ID NO:10 or a sequence substantially homologous thereto. In alternative embodiments of the invention, the antibody comprises a light chain (VL) CDR3 domain comprising the amino acid sequence of SEQ ID NO:30, SEQ ID NO: 43, SEQ ID NO:56, SEQ ID NO:69 or SEQ ID NO:82, or a sequence substantially homologous thereto.

Thus, in certain embodiments, the invention provides an antibody that binds to EpCAM comprising one or more heavy chain CDR domains, wherein the heavy chain CDR domain is selected from the group consisting of:
(a) a heavy chain CDR1 domain comprising the amino acid sequence of SEQ ID NO:5 or a sequence substantially homologous thereto;
(b) a heavy chain CDR2 domain comprising the amino acid sequence of SEQ ID NO:6 or a sequence substantially homologous thereto; and
(c) a heavy chain CDR3 domain comprising the amino acid sequence of SEQ ID NO:7 or a sequence substantially homologous thereto.

The invention also provides, in certain embodiments, an antibody that binds to EpCAM comprising one or more light chain CDR domains, wherein the light chain CDR domain is selected from the group consisting of:
(a) a light chain CDR1 domain comprising the amino acid sequence of SEQ ID NO:8 or a sequence substantially homologous thereto;
(b) a light chain CDR2 domain comprising the amino acid sequence of SEQ ID NO:9 or SEQ ID NO:29, or a sequence substantially homologous thereto; and
(c) a light chain CDR3 domain comprising the amino acid sequence of SEQ ID NO:10, SEQ ID NO:30, SEQ ID NO:43, SEQ ID NO:56, SEQ ID NO:69 or SEQ ID NO:82, or a sequence substantially homologous thereto.

In certain preferred embodiments, the antibody that binds to EpCAM comprises both
(a) a heavy chain CDR3 comprising the amino acid sequence of SEQ ID NO:7 or a sequence substantially homologous thereto; and
(b) a light chain CDR3 comprising the amino acid sequence of SEQ ID NO:10, SEQ ID NO:30, SEQ ID NO:43, SEQ ID NO:56, SEQ ID NO:69 or SEQ ID NO:82, or a sequence substantially homologous thereto.

More preferably, a heavy chain CDR1 domain comprising the amino acid sequence of SEQ ID NO:5 or a sequence substantially homologous thereto and/or a light chain CDR1 domain comprising the amino acid sequence of SEQ ID NO:8 or a sequence substantially homologous thereto, and/or a heavy chain CDR2 domain comprising the amino acid sequence of SEQ ID NO:6 or a sequence substantially homologous thereto and/or a light chain CDR2 domain comprising the amino acid sequence of SEQ ID NO:9 or SEQ ID NO:29, or a sequence substantially homologous thereto, are also present.

In one preferred embodiment, the heavy chain CDR1 comprising the amino acid sequence of SEQ ID NO:5 or a sequence substantially homologous thereto, CDR2 comprising the amino acid sequence of SEQ ID NO:6 or a sequence substantially homologous thereto, and CDR3 comprising the amino acid sequence of SEQ ID NO:7, or a sequence substantially homologous thereto, are present individually or in combination.

In yet another preferred embodiment, the light chain CDR1 comprising the amino acid sequence of SEQ ID NO:8 or a sequence substantially homologous thereto, CDR2 comprising the amino acid sequence of SEQ ID NO:9 or SEQ ID NO:29, or a sequence substantially homologous thereto, and CDR3 comprising the amino acid sequence of SEQ ID NO:10, SEQ ID NO:30, SEQ ID NO:43, SEQ ID NO:56, SEQ ID NO:69 or SEQ ID NO:82, or a sequence substantially homologous thereto, are present individually or in combination.

Viewed alternatively, in certain embodiments, the present invention provides an antibody that binds to EpCAM comprising:
a heavy chain CDR3 domain comprising the amino acid sequence of SEQ ID NO:7 or a sequence substantially homologous thereto and/or a light chain CDR3 domain comprising the amino acid sequence of SEQ ID NO:10, SEQ ID NO:30, SEQ ID NO:43, SEQ ID NO:56, SEQ ID NO:69 or SEQ ID NO:82, or a sequence substantially homologous thereto.

Said antibody optionally further comprises:
a heavy chain CDR2 domain comprising the amino acid sequence of SEQ ID NO:6 or a sequence substantially homologous thereto and/or a light chain CDR2 domain comprising the amino acid sequence of SEQ ID NO:9 or SEQ ID NO:29, or a sequence substantially homologous thereto and/or further comprises:
a heavy chain CDR1 domain comprising the amino acid sequence of SEQ ID NO:5 or a sequence substantially homologous thereto and/or
a light chain CDR1 domain comprising the amino acid sequence of SEQ ID NO:8 or a sequence substantially homologous thereto.

Viewed alternatively, in certain embodiments, the present invention provides an antibody that binds to EpCAM comprising:
a heavy chain CDR2 domain comprising the amino acid sequence of SEQ ID NO:6 or a sequence substantially homologous thereto and/or a light chain CDR2 domain comprising the amino acid sequence of SEQ ID NO:9 or SEQ ID NO:29, or a sequence substantially homologous thereto.

Said antibody optionally further comprises:
a heavy chain CDR3 domain comprising the amino acid sequence of SEQ ID NO:7 or a sequence substantially homologous thereto and/or a light chain CDR3 domain comprising the amino acid sequence of SEQ ID NO:10, SEQ ID NO:30, SEQ ID NO:43, SEQ ID NO:56, SEQ ID NO:69 or SEQ ID NO:82, or a sequence substantially homologous thereto and/or further comprises:
a heavy chain CDR1 domain comprising the amino acid sequence of SEQ ID NO:5 or a sequence substantially homologous thereto and/or
a light chain CDR1 domain comprising the amino acid sequence of SEQ ID NO:8 or a sequence substantially homologous thereto.

Viewed alternatively, in certain embodiments, the present invention provides an antibody that binds to EpCAM comprising:
a heavy chain CDR1 domain comprising the amino acid sequence of SEQ ID NO:5 or a sequence substantially homologous thereto and/or a light chain CDR1 domain comprising the amino acid sequence of SEQ ID NO:8 or a sequence substantially homologous thereto.

Said antibody optionally further comprises:
a heavy chain CDR3 domain comprising the amino acid sequence of SEQ ID NO:7 or a sequence substantially homologous thereto and/or a light chain CDR3 domain comprising the amino acid sequence of SEQ ID NO:10, SEQ ID NO:30, SEQ ID NO:43, SEQ ID NO:56, SEQ ID NO:69 or SEQ ID NO:82, or a sequence substantially homologous thereto and/or further comprises:
a heavy chain CDR2 domain comprising the amino acid sequence of SEQ ID NO:6 or a sequence substantially homologous thereto and/or
a light chain CDR2 domain comprising the amino acid sequence of SEQ ID NO:9 or SEQ ID NO:29, or a sequence substantially homologous thereto.

Certain preferred antibodies of the invention comprise one or more of the CDRs selected from the group consisting of SEQ ID NOs:5, 6, 7, 8, 9 and 10 or a sequence substantially homologous to any one of the foregoing SEQ ID NOs. Other preferred CDRs are selected from the group consisting of SEQ ID NOs:29 (for VL CDR2), and SEQ ID NOs: 30, 43, 56, 69 and 82 (for VL CDR3).

Other certain preferred antibodies comprise two or more of the heavy chain CDRs of SEQ ID NOs:5, 6 or 7, or sequences substantially homologous to any one of the foregoing SEQ ID NOs. Especially preferred binding molecules comprise 3 of the heavy chain CDRs of SEQ ID NOs:5, 6 and 7, or sequences substantially homologous to any one of the foregoing SEQ ID NOs (i.e. one of each of the aforementioned heavy chain CDR1 and CDR2 and CDR3 or sequences substantially homologous thereto).

Certain preferred antibodies comprise two or more of the light chain CDRs of SEQ ID NOs:8 (for VL CDR1), 9 or 29 (for VL CDR2), or 10, 30, 43, 56, 69 or 82 (for VL CDR3), or sequences substantially homologous to any one of the foregoing SEQ ID NOs. Especially preferred binding molecules comprise 3 of the light chain CDRs of SEQ ID NOs:8 (for VL CDR1), 9 or 29 (for VL CDR2), or 10, 30, 43, 56, 69 or 82 (for VL CDR3), or sequences substantially homologous to any one of the foregoing SEQ ID NOs (i.e. one of each of the aforementioned light chain CDR1 and CDR2 and CDR3 or sequences substantially homologous thereto).

Certain more especially preferred antibodies comprise 3 of the light chain CDRs of SEQ ID NOs:8 (for VL CDR1), 9 or 29 (for VL CDR2), or 10, 30, 43, 56, 69 or 82 (for VL CDR3), or sequences substantially homologous to any one of these sequences (i.e., one of each of the aforementioned light chain CDR1 and CDR2 and CDR3 or sequences substantially homologous thereto), and 3 of the heavy chain CDRs of SEQ ID NOs:5, 6 or 7, or sequences substantially homologous any one of these sequences (i.e., one of each of the aforementioned heavy chain CDR1 and CDR2 and CDR3 or sequences substantially homologous thereto).

Certain especially preferred antibodies comprise:
a heavy chain CDR1 domain of SEQ ID NO:5,
a heavy chain CDR2 domain of SEQ ID NO:6, and
a heavy chain CDR3 domain of SEQ ID NO:7,
or sequences substantially homologous to any one of the aforementioned sequences;
and/or comprise:
a light chain CDR1 domain of SEQ ID NO:8,
a light chain CDR2 domain of SEQ ID NO:9, and
a light chain CDR 3 domain of SEQ ID NO:10,
or sequences substantially homologous to any one of the aforementioned sequences.

Alternative preferred light chain CDR combinations are SEQ ID NO:8 (for VL CDR1) and SEQ ID NO:29 (for VL CDR2) and SEQ ID NO:30 or SEQ ID NO:43 or SEQ ID NO:56 or SEQ ID NO:69 or SEQ ID NO:82 (for VL CDR3), or sequences substantially homologous to any one of the aforementioned sequences.

In a further embodiment, the invention provides an antibody that binds to EpCAM and that comprises at least one heavy chain variable region that comprises three CDRs and at least one light chain variable region that comprises three CDRs, wherein said heavy chain variable region comprises:
(c) a VH CDR3 that has the amino acid sequence of SEQ ID NO:7 or a sequence substantially homologous thereto.

In a further embodiment, the invention provides an antibody that binds to EpCAM and that comprises at least one heavy chain variable region that comprises three CDRs and at least one light chain variable region that comprises three CDRs, wherein said heavy chain variable region comprises:
(a) a VH CDR1 that has the amino acid sequence of SEQ ID NO:5 or a sequence substantially homologous thereto,
(b) a VH CDR2 that has the amino acid sequence of SEQ ID NO:6 or a sequence substantially homologous thereto, and
(c) a VH CDR3 that has the amino acid sequence of SEQ ID NO:7 or a sequence substantially homologous thereto.

In a preferred aspect of this embodiment, one or more of said light chain variable region CDRs are selected from the group consisting of:
(d) a variable light (VL) CDR1 that has the amino acid sequence of SEQ ID NO:8 or a sequence substantially homologous thereto,
(e) a VL CDR2 that has the amino acid sequence of SEQ ID NO:9 or SEQ ID NO:29, or a sequence substantially homologous thereto, and
(f) a VL CDR3 that has the amino acid sequence of SEQ ID NO:10, SEQ ID NO:30, SEQ ID NO:43, SEQ ID NO:56, SEQ ID NO:69 or SEQ ID NO:82, or a sequence substantially homologous thereto.

In a further preferred aspect of this embodiment, two of said light chain variable region CDRs are selected from the group consisting of:
(d) a variable light (VL) CDR1 that has the amino acid sequence of SEQ ID NO:8 or a sequence substantially homologous thereto,
(e) a VL CDR2 that has the amino acid sequence of SEQ ID NO:9 or SEQ ID NO:29 or a sequence substantially homologous thereto, and
(f) a VL CDR3 that has the amino acid sequence of SEQ ID NO:10, SEQ ID NO:30, SEQ ID NO:43, SEQ ID NO:56, SEQ ID NO:69 or SEQ ID NO:82, or a sequence substantially homologous thereto.

In a yet further preferred aspect of this embodiment, three of said light chain variable region CDRs are selected from the group consisting of:
(d) a variable light (VL) CDR1 that has the amino acid sequence of SEQ ID NO:8 or a sequence substantially homologous thereto,
(e) a VL CDR2 that has the amino acid sequence of SEQ ID NO:9 or SEQ ID NO:29, or a sequence substantially homologous thereto, and
(f) a VL CDR3 that has the amino acid sequence of SEQ ID NO:10, SEQ ID NO:30, SEQ ID NO:43, SEQ ID NO:56, SEQ ID NO:69 or SEQ ID NO:82, or a sequence substantially homologous thereto.

In a further embodiment, the invention provides an antibody that binds to EpCAM and that comprises at least one heavy chain variable region that comprises three CDRs and at least one light chain variable region that comprises three CDRs, wherein said light chain variable region comprises:
(i) a variable light (VL) CDR1 that has the amino acid sequence of SEQ ID NO:8 or a sequence substantially homologous thereto,
(ii) a VL CDR2 that has the amino acid sequence of SEQ ID NO:9 or SEQ ID NO:29, or a sequence substantially homologous thereto, and
(iii) a VL CDR3 that has the amino acid sequence of SEQ ID NO:10, SEQ ID NO:30, SEQ ID NO:43, SEQ ID NO:56, SEQ ID NO:69 or SEQ ID NO:82, or a sequence substantially homologous thereto.

In a preferred aspect of this embodiment, one or more of said heavy chain variable region CDRs are selected from the group consisting of:
(i) a VH CDR1 that has the amino acid sequence of SEQ ID NO:5 or a sequence substantially homologous thereto,
(ii) a VH CDR2 that has the amino acid sequence of SEQ ID NO:6 or a sequence substantially homologous thereto, and
(iii) a VH CDR3 that has the amino acid sequence of SEQ ID NO:7 or a sequence substantially homologous thereto.

In a further preferred aspect of this embodiment, two of said heavy chain variable region CDRs are selected from the group consisting of:
(i) a VH CDR1 that has the amino acid sequence of SEQ ID NO:5 or a sequence substantially homologous thereto,
(ii) a VH CDR2 that has the amino acid sequence of SEQ ID NO:6 or a sequence substantially homologous thereto, and
(iii) a VH CDR3 that has the amino acid sequence of SEQ ID NO:7 or a sequence substantially homologous thereto.

In a yet further preferred aspect of this embodiment, three of said heavy chain variable region CDRs are selected from the group consisting of:
(i) a VH CDR1 that has the amino acid sequence of SEQ ID NO:5 or a sequence substantially homologous thereto,
(ii) a VH CDR2 that has the amino acid sequence of SEQ ID NO:6 or a sequence substantially homologous thereto, and
(iii) a VH CDR3 that has the amino acid sequence of SEQ ID NO:7 or a sequence substantially homologous thereto.

Certain further preferred embodiments of the invention provide an antibody that binds to EpCAM and that comprises:
a VH domain that comprises one, two or three of the heavy chain CDRs of SEQ ID NOs:5, 6, or 7, or sequences substantially homologous to one or more of SEQ ID NOs:5, 6, or 7, and/or
a VL domain that comprises one, two or three of the light chain CDRs of SEQ ID NOs:8 (for VL CDR1), 9 or 29 (for VL CDR2), or 10, 30, 43, 56, 69 or 82 (for VL CDR3), or sequences substantially homologous to one or more of these sequences.

Especially preferred VH domains comprise 3 of the heavy chain CDRs of SEQ ID NOs:5, 6, and 7, or sequences substantially homologous to one or more of SEQ ID NOs:5, 6, or 7 (i.e., one of each of CDR1, CDR2 and CDR3 or sequences substantially homologous thereto).

Especially preferred VL domains comprise 3 of the light chain CDRs of SEQ ID NOs:8 (for VL CDR1), 9 or 29 (for VL CDR2), or 10, 30, 43, 56, 69 or 82 (for VL CDR3), or sequences substantially homologous to one or more of these sequences, (i.e., one of each of CDR1, CDR2 and CDR3 or sequences substantially homologous thereto).

More especially preferred embodiments of the invention provide an antibody that binds to EpCAM and that comprises:
a VH domain that comprises 3 heavy chain CDRs of SEQ ID NOs:5, 6 and 7, and a VL domain that comprises 3 light chain CDRs. In preferred embodiments one, two or three of the light chain CDRs are as defined in SEQ ID NOs:8, 9, and 10.
Sequences substantially homologous thereto are also included.
In alternative VL domains, one, two or three of the light chain CDRs are as defined in SEQ ID NOs: 8, 29 and 30; 8, 29 and 43; 8, 29 and 56; 8, 29 and 69; and 8, 29 and 82. Sequences substantially homologous thereto are also included.

Certain preferred embodiments of the invention provide an antibody that binds EpCAM comprising a VH domain that comprises the amino acid sequence of SEQ ID NO:3 or a sequence substantially homologous thereto and/or a VL domain that comprises the amino acid sequence of SEQ ID NOs:4, 27, 40, 53, 66 or 79, or a sequence substantially homologous thereto.

Further preferred embodiments provide an antibody that binds EpCAM comprising a VH domain that comprises the amino acid sequence of SEQ ID NO:3 and a VL domain that comprises 3 light chain CDRs. Preferably said VL domain comprises the amino acid sequence of SEQ ID NOs:4, 27, 40, 53, 66 or 79.

Other embodiments of the invention provide an antibody that binds to EpCAM and that comprises:
a VL domain that comprises 3 light chain CDRs of SEQ ID NOs:8, 9 and 10, and a VH domain that comprises 3 heavy chain CDRs. In preferred embodiments one, two or three of the heavy chain CDRs are as defined in SEQ ID NOs:5, 6, and 7.

Further preferred embodiments provide an antibody that binds EpCAM comprising a VL domain that has the amino acid sequence of SEQ ID NOs:4, 27, 40, 53, 66 or 79, and a VH domain that comprises 3 heavy chain CDRs. Preferably said VH domain has the amino acid sequence of SEQ ID NO:3.

In a yet further embodiment, the present invention provides an antibody that binds EpCAM comprising the amino acid sequence of SEQ ID NO:21 (said antibody also being referred to herein as 3-17I ScFv), or comprising a fragment thereof that binds EpCAM, or a sequence substantially homologous thereto.

Other antibodies of the invention comprise the amino acid sequence of SEQ ID NO:36 (said antibody also being referred to herein as 7-F17 scFv), SEQ ID NO:49 (said antibody also being referred to herein as 12-C15 scFv), SEQ ID NO:62 (said antibody also being referred to herein as 16-G5 scFv), SEQ ID NO:75 (said antibody also being referred to herein as 17-C20 scFv) and SEQ ID NO:88 (said antibody also being referred to herein as 24-G6 scFv), or comprising a fragment thereof that binds EpCAM, or a sequence substantially homologous thereto.

The invention is exemplified by monoclonal antibody 3-17I, a single chain form of which is shown in FIG. 1 (SEQ ID NO:21 and SEQ ID NO:20) and a full length IgG form of which is described in Example 1 and Table 1. The 3-17I antibody comprises a VH domain of SEQ ID No:3 and a VL domain of SEQ ID NO:4. The CDR domains, VH and VL domains of the 3-17I antibody are shown in Table 1 and FIG. 1. Antibodies comprising these CDR domains or VH and VL domains (or sequences substantially homologous thereto) are preferred aspects of the invention.

Other exemplified antibodies of the invention are 7-F17, 12-C15, 16-G5, 17-C20 and 24-G6. The 7-F17 antibody comprises a VH domain of SEQ ID No:3 and a VL domain of SEQ ID NO:27. The 12-C15 antibody comprises a VH domain of SEQ ID No:3 and a VL domain of SEQ ID NO:40. The 16-G5 antibody comprises a VH domain of SEQ ID No:3 and a VL domain of SEQ ID NO:53. The 17-C20 antibody comprises a VH domain of SEQ ID No:3 and a VL domain of SEQ ID NO:66. The 24-G6 antibody comprises a VH domain of SEQ ID No:3 and a VL domain of SEQ ID NO:79. Thus, these antibodies have the same heavy chain as 3-17I but different light chains the sequences of which are shown in Tables 2, 3, 4, 5 and 6, respectively. Antibodies comprising these CDR domains or VH and VL domains (or sequences substantially homologous thereto) are preferred aspects of the invention.

A preferred embodiment of the invention is a scFv form of the 3-17I antibody shown in SEQ ID NO:21 (amino acid), which is preferably encoded by SEQ ID NO:20 (nucleic acid). Another embodiment of the invention is a scFv form of the 7-F17 antibody shown in SEQ ID NO:36 (amino acid), which is preferably encoded by SEQ ID NO:35 (nucleic acid). Another embodiment of the invention is a scFv form of the 12-C15 antibody shown in SEQ ID NO:49 (amino acid), which is preferably encoded by SEQ ID NO:48 (nucleic acid). Another embodiment of the invention is a scFv form of the 16-G5 antibody shown in SEQ ID NO:62 (amino acid), which is preferably encoded by SEQ ID NO:61 (nucleic acid). Another embodiment of the invention is a scFv form of the 17-C20 antibody shown in SEQ ID NO:75 (amino acid), which is preferably encoded by SEQ ID NO:74 (nucleic acid). Another embodiment of the invention is a scFv form of the 24-G6 antibody shown in SEQ ID NO:88 (amino acid), which is preferably encoded by SEQ ID NO:87 (nucleic acid).

Another preferred embodiment of the invention is a full length IgG form of the 3-17I antibody, the heavy chain of which is shown in SEQ ID NO:24 (amino acid), which is preferably encoded by SEQ ID NO:22 (nucleic acid); and the light chain of which is shown in SEQ ID NO:25 (amino acid), which is preferably encoded by SEQ ID NO:23 (nucleic acid). Full length IgG forms of the 7-F17, 12-C15, 16-G5,17-C20 and 24-G6 antibodies are also preferred embodiments.

Thus, preferred antibodies of the invention comprise the VH and VL domains of 3-171, i.e. comprise SEQ ID NO:3 and SEQ ID NO:4 or sequences substantially homologous thereto. Other preferred antibodies comprise the VH and VL domains of 7-F17, 12-C15, 16-G5,17-C20 and 24-G6, or sequences substantially homologous thereto.

In all the embodiments of the invention described herein, the VL CDR2 domain has or comprises an amino acid sequence of G A S T $X_5$ A $X_7$ (SEQ ID NO:37) or a sequence substantially homologous thereto, wherein $X_5$ and $X_7$ can be any amino acid. In these embodiments $X_5$ can be R or T, preferably T. $X_7$ can be T or S, preferably S. Thus, a preferred VL CDR2 has or comprises an amino acid sequence of G A S T R/T A T/S (SEQ ID NO:38). See also Table 7.

In all the embodiments of the invention described herein, the VL CDR3 domain has or comprises an amino acid sequence of Q $X_2$ Y N $X_5$ W P P $X_9$ $X_{10}$ T (SEQ ID NO:89) or a sequence substantially homologous thereto, wherein $X_2$, $X_5$, $X_9$ and $X_{10}$ can be any amino acid. In these embodiments $X_2$ can be Q or H or K, preferably Q. $X_5$ can be N or D, preferably N. $X_9$ can be G or T or S or M or A, preferably A. $X_{10}$ can be F or W or Y, preferably Y. Thus, a preferred VL CDR3 has or comprises an amino acid sequence of Q Q/H/K Y N N/D W P P G/T/S/M/A F/W/Y T (SEQ ID NO:90). See also Table 7.

Certain examples of substantially homologous sequences are sequences that have at least 70% identity to the amino acid sequences disclosed.

In certain embodiments, the antibodies of the invention that bind to EpCAM comprise at least one light chain variable region that includes an amino acid sequence region of at least about 70% or 75%, more preferably at least about 80%, more preferably at least about 85%, more preferably at least about 90% or 95% and most preferably at least about 97%, 98% or 99% amino acid sequence identity to the amino acid sequence of SEQ ID NOs:4, 27, 40, 53, 66 or 79; and/or at least one heavy chain variable region that includes an amino acid sequence region of at least about 70% or 75%, more preferably at least about 80%, more preferably at least about 85%, more preferably at least about 90% or 95% and most preferably at least about 97%, 98% or 99% amino acid sequence identity to the amino acid sequence of SEQ ID NO:3.

Other preferred examples of substantially homologous sequences are sequences containing conservative amino acid substitutions of the amino acid sequences disclosed.

Other preferred examples of substantially homologous sequences are sequences containing 1, 2 or 3, preferably 1 or 2, altered amino acids in one or more of the CDR regions disclosed. Such alterations might be conserved or non-conserved amino acid substitutions, or a mixture thereof.

In all such embodiments, preferred alterations are conservative amino acid substitutions.

In all embodiments, the antibodies containing substantially homologous sequences retain the ability to bind EpCAM and preferably retain one or more of the other properties described herein, e.g. the ability to bind at least to human EpCAM, preferably to human and monkey EpCAM.

Other embodiments of the present invention provide binding proteins that bind to EpCAM and that comprise an antibody of the invention, a VH or VL domain of the invention, or one or more of the CDRs of the invention. In a preferred embodiment, such binding proteins are antibodies. Preferred combinations of VH, VL and CDR domains for use in such binding proteins are discussed elsewhere herein.

Preferred antibodies of the invention comprise at least one heavy chain variable region that comprises three CDRs and at least one light chain variable region that comprises three CDRs. Exemplary and preferred sequences for these CDRs are described herein.

As used herein, the succinct term "EpCAM", unless otherwise specifically stated or made clear from the scientific terminology, means Epithelial Cell Adhesion Molecule. EpCAM may also be referred to as EGP-2, 17-1A, HEA125, MK-1, GA733-2, EGP34, KSA, TROP-1, ESA, TACSTD1 or KS1/4.

"EpCAM" may also refer to any form of EpCAM, particularly as EpCAM is conserved across mammalian species (Trzpis et al., 2008, Transgenic Res 17:229-238). The antibodies or antibody fragments of the invention may thus bind to human, monkey (e.g. cynomolgus monkey), cow (bovine), mouse, rat, hamster, ferret, guinea pig and/or rabbit EpCAM, for example. Preferably, the antibodies or antibody fragments of the invention will bind at least to human EpCAM. In certain preferred embodiments, the antibodies or antibody fragments of the invention will bind at least to human and monkey (e.g. cynomologus monkey) EpCAM. In other preferred embodiments the antibodies or antibody fragments of the invention will bind at least to human and mouse EpCAM. In other preferred embodiments the antibodies or antibody fragments of the invention will bind at least to human, monkey and mouse EpCAM. EpCAM may be free EpCAM, e.g. recombinant or purified EpCAM, or may be present in a native form, e.g. on the surface of a cell.

The antibodies or binding proteins of the invention can also bind to fragments of EpCAM, in particular fragments comprising or consisting of the extracellular domain, or can bind to entities comprising EpCAM or fragments of EpCAM. Indeed, the epitopes of the antibodies of the invention are located in the extracellular domain of EpCAM.

As used herein, the term "that binds to EpCAM" or "anti-EpCAM" in the context of antibodies or antibody fragments of the present invention, means antibodies or antibody fragments that are capable of one or more of the following; preferably, of more than one of the following; and most preferably, of all of the following:

(a) bind to free EpCAM; e.g. recombinantly expressed EpCAM, on a solid support, e.g. as assessed by ELISA assay or BIAcore assay;

(b) bind to a conformationally dependent (e.g. non linear) EpCAM epitope, e.g. as assessed by binding to EpCAM in a Western blot under non-reducing conditions;

(c) bind to EpCAM expressed on the surface of a cell, e.g. as assessed by flow cytometry or immunohistochemistry;

(d) bind at least to human EpCAM, more preferably to human and monkey EpCAM or to human and mouse EpCAM, most preferably to human, monkey and mouse EpCAM;

(e) bind to human EpCAM with a binding affinity (Kd) of 10 nM or less, preferably 5 nM or less, more preferably 3 nM or less or 2 nM or less, most preferably 1 nM or less as also discussed elsewhere herein;

(f) bind to human and monkey EpCAM or to human and mouse EpCAM with similar affinities, e.g. with a Kd of 10 nM or less, preferably 5 nM or less, more preferably 3 nM or less or 2 nM or less, for example 1 nM or less as also discussed elsewhere herein.

Preferred antibodies or antibody fragments of the present invention are also capable of one or more of the following; preferably, of more than one of the following; and most preferably, of all of the following functional properties:

(g) localize to tumors upon administration to an animal with a tumor;

(h) induce ADCC of tumor cells as described elsewhere herein;

(i) induce CDC of tumor cells as described elsewhere herein;

(j) induce anti-tumor effects in vivo.

Further information about these preferred properties is described elsewhere herein. Other preferred properties include the absence of significant toxicity in vivo when the antibodies of the invention are administered and the absence of significant other side effects in vivo, e.g. side effects such as pancreatitis or other collateral damage to normal tissues which have for example been observed with other anti-EpCAM antibodies. The antibodies of the invention may also inhibit or significantly reduce the function of EpCAM or prevent or reduce the interaction of EpCAM with its natural ligands. Another preferred (but not essential) property of the antibodies of the invention is a capability to have a therapeutic effect in a monospecific format, i.e. in a format in which only one antibody specificity is present.

In light of this invention, therefore, a range of anti-EpCAM antibodies can be made and used in a variety of embodiments, including in the treatment of cancer.

As used throughout the entire application, the terms "a" and "an" are used in the sense that they mean "at least one", "at least a first", "one or more" or "a plurality" of the referenced components or steps, except in instances wherein an upper limit is thereafter specifically stated. Therefore, an "antibody", as used herein, means "at least a first antibody". The operable limits and parameters of combinations, as with the amounts of any single agent, will be known to those of ordinary skill in the art in light of the present disclosure.

Preferred embodiments of the invention are compositions comprising at least one anti-EpCAM antibody of the invention, or antigen binding fragment thereof.

Nucleic acid molecules comprising nucleotide sequences that encode the antibodies of the present invention as defined herein or parts or fragments thereof, or nucleic acid molecules substantially homologous thereto, form yet further aspects of the invention. Preferred nucleic acid molecules comprise sequences which encode the amino acid sequence set out in SEQ ID NO:21 (which is preferably encoded by SEQ ID NO:20). Other preferred nucleic acid molecules comprise sequences which encode the amino acid sequence set out in SEQ ID NO:36 (which is preferably encoded by SEQ ID NO:35), or sequences which encode the amino acid sequence set out in SEQ ID NO:49 (which is preferably encoded by SEQ ID NO:48), or sequences which encode the amino acid sequence set out in SEQ ID NO:62 (which is preferably encoded by SEQ ID NO:61), or sequences which encode the amino acid sequence set out in SEQ ID NO:75 (which is preferably encoded by SEQ ID NO:74), or sequences which encode the amino acid sequence set out in SEQ ID NO:88 (which is preferably encoded by SEQ ID NO:87). Other preferred nucleic acid molecules comprise sequences which encode a heavy chain that has the amino acid sequence of SEQ ID NO:24 (which is preferably encoded by SEQ ID NO:22) and/or comprise sequences which encode a light chain which has the amino acid sequence of SEQ ID NO:25 (which is preferably encoded by SEQ ID NO:23), or a light chain which has the amino acid sequence of SEQ ID NO:51 (which is preferably encoded by SEQ ID NO:50), or a light chain which has the amino acid sequence of SEQ ID NO:64 (which is preferably encoded by SEQ ID NO:63), or a light chain which has the amino acid sequence of SEQ ID NO:77 (which is preferably encoded by SEQ ID NO:76).

Other preferred nucleic acid molecules comprise sequences that encode IgG forms of the antibodies of the invention, for example those as described in Example 1, or murine chimeric forms.

As indicated above, other nucleic acid molecules encompassed by the present invention are those encoding parts or fragments of the human antibodies of the present invention, e.g., those encoding a heavy chain of an antibody (e.g., those encoding SEQ ID NO:24, such as SEQ ID NO:22) or those encoding a light chain of an antibody (e.g., those encoding SEQ ID NO:25, such as SEQ ID NO:23). Other preferred nucleic acid molecules are those encoding a VH region of an antibody of the present invention (e.g., those encoding SEQ ID NO:3, such as SEQ ID NO:1. Other preferred nucleic acid molecules are those encoding a VL region of an antibody of the present invention (e.g., those encoding SEQ ID NO:4, such as SEQ ID NO:2, those encoding SEQ ID NO:27, such as SEQ ID NO:26, those encoding SEQ ID NO:40, such as SEQ ID NO:39, those encoding SEQ ID NO:53, such as SEQ ID NO:52, those encoding SEQ ID NO:66, such as SEQ ID NO:65, or those encoding SEQ ID NO:79, such as SEQ ID NO:78).

Thus, fragments of the antibodies of the invention as defined herein, or sequences substantially homologous thereto, or nucleic acid molecules comprising sequences encoding such fragments form a yet further aspect of the invention.

There is a general consideration that the high affinity anti-EpCAM antibodies have intolerable toxicity profiles, since they cannot distinguish the malignant and normal tissues. Therefore, a therapeutic window may exist only for low affinity antibodies such as edrecolomab and MT201. On the other hand, the low affinity antibodies have relatively low efficacy in tumor eradication. For example, according to the Micromet website, Adecatumumab (MT201) missed primary endpoint (i.e., 25 percent clinical benefit rate at week 24) as a single agent in Phase II trials for treatment of metastatic breast and prostate cancer.

The antibodies of the present invention, when in IgG format, have unique features of EpCAM-binding affinity. Although the calculated affinity at equilibrium ($K_D$) seems to be high (around 1 nM), the kinetic components (on- and off-rates) have different contribution to the affinity. The antibodies of the present invention have very high on-rates (of the order of $10^7$ $M^{-1}s^{-1}$) which determine quick recognition and binding to target cells, and, at the same time, relatively high off-rates ($10^{-2}$–$10^{-3}$ $s^{-1}$) that determine quick antibody dissociation with half-lives on the cell surface of 3-4 min. This unique binding profile will potentially lead to a combination of high anti-tumor efficacy with low toxicity profile. This kinetic profile, which is distinctively different from what is shown in the prior art, may result in different (and potentially superior) pharmocokinetics of the antibody when used in vivo.

Any appropriate method of determining on- and especially off-rates may be used. However, preferably the kinetic constants are determined by testing various concentrations of the test antibody against fixed concentrations of immobilized antigen (EpCAM) in vitro by using commercially available binding model software, such as the 1:1 binding model (e.g. the Langmuir binding model) in the BIAcore T100 model. A suitable assay is described in Example 3 for illustrative purposes. Preferably the constants are determined by immobilizing antigen (EpCAM) on a solid support, e.g. a BIAcore chip, and assessing the binding of the antibody to the antigen. Preferably the binding affinity is assessed at 37° C. (e.g. body temperature), although it may also be assessed at other temperatures, e.g. room temperature, e.g. a temperature of 25° C.

Alternatively, the off-rate and the antibody half-life on the surface of the EpCAM positive cell can be determined by performing the cell surface retention assay (Adams et al., 1998, Br J Cancer 77: 1405-12; Le Gall et al., 1999, FEBS Lett 453: 164-8). The latter method allows more appropriate mimicking the real situation in human patient under the treatment conditions.

The antibodies of the present invention, when in IgG format, have a relatively high binding affinity for EpCAM, i.e., have a Kd in the range of $1\times10^{-8}$ M or $1\times10^{-9}$ M or less. Thus, the antibodies of the invention, when in IgG format, have a binding affinity for EpCAM (preferably human EpCAM) that corresponds to a Kd of less than 20 nM, 15 nM or 10 nM, more preferably of less than 10, 9.5, 9, 8.5, 8, 7.5, 7, 6.5, 6, 5.5, 5, 4.5, 4, 3.5, 3, 2.5, 2, 1.5, 1, 0.9, 0.8, 0.7, 0.6, 0.5, 0.4, 0.3, 0.2 or 0.1 nM, However, antibodies with higher Kds may equally be used in the present invention providing they have the appropriate functional properties as described elsewhere herein.

Any appropriate method of determining Kd may be used. However, preferably the Kd is determined by testing various concentrations of the test antibody against various concentrations of immobilized antigen (EpCAM) in vitro to establish a saturation curve, for example using the Lineweaver-Burk method, or preferably by using commercially available binding model software, such as the 1:1 binding model (e.g. the Langmuir binding model) in the BIAcore T100 model. Thus, BIAcore assays are preferred for measuring Kd and a suitable assay is described in Example 3 for illustrative purposes. Preferably the Kd is determined by immobilizing antigen (EpCAM), preferably free antigen, e.g. free EpCAM or a molecule comprising the extracellular domain of EpCAM, on a solid support, e.g. a BIAcore chip, and assessing the binding of the antibody to the antigen. Preferably the binding affinity is assessed at 37° C. (e.g. body temperature), although it may also be assessed at other temperatures, e.g. room temperature, e.g. a temperature of 25° C. Preferably IgG forms of the antibodies are used to determine binding affinity.

As discussed elsewhere herein, preferred antibodies of the invention bind to both human EpCAM and monkey EpCAM. Such cross-reactivity between species and in particular between humans and species commonly used as pre-clinical animal models is an important advantage as it allows a more effective translation from pre-clinical studies to clinical use. For example, having an antibody which cross reacts with the native EpCAM present in the particular animal model used means that the results in this model are more likely to reflect the situation in a human patient, thereby allowing a more accurate assessment of for example dosing to be made and an increased likelihood of identifying any potentially relevant or problematic side effects. This is especially the case if the antibody has similar affinity to both monkey and human EpCAM.

For example, the ability of an antibody of the invention to bind to both human EpCAM and monkey EpCAM means that such antibodies can be tested in preclinical toxicity studies to assess adverse side effects of the treatment and to find appropriate tolerated dosages.

In addition, the ability to bind both human EpCAM and mouse EpCAM means that the results shown by such antibodies of the invention in mouse models, e.g. mouse syngeneic models using immunocompetent mice, are more likely to be representative of the activity of the antibodies in human subjects. This is especially the case if the antibody has similar affinity to both murine and human EpCAM. The reason for this is that antibodies which can bind to human EpCAM but not mouse EpCAM will bind to EpCAM expressed by the human tumor cells in the mouse model but will not be able to bind to endogenous murine EpCAM. This is of course unlike the situation in a human patient, in which EpCAM expressed by the tumor and endogenous EpCAM would be present.

The potential disadvantage with such a situation is that an antibody which binds to human EpCAM but not, or with significantly lower affinity, to mouse EpCAM might perform well in a human tumor xenograft model in immunocompromized mice (e.g. nude or SCID mice) but this might not be reflected by a similar performance in a human system where much more EpCAM was present. In other words, the anti-tumor effect seen in a mouse xenograft system with an antibody which can bind to human EpCAM but not mouse EpCAM might look better than the clinical reality. In contrast, when working with an antibody that can bind to both human and mouse EpCAM then this will bind to all forms of EpCAM present in the mouse model system and is likely to be more representative of the situation when the antibody is put into humans. This is especially the case if the antibody has similar affinity to both murine and human EpCAM.

The similar affinity for monkey and human EpCAM displayed by the 3-171 antibody of the invention (and other preferred antibodies of the invention) is a clear advantage over the MOC31 prior art antibody (which has a much lower affinity for monkey EpCAM than for human EpCAM) and is also an advantage over the MT201 antibody which shows no detectable binding to monkey EpCAM.

Thus, preferred antibodies of the invention bind to human and monkey EpCAM or to human and mouse EpCAM with similar affinities or similar on-rates or similar off-rates, e.g. as described elsewhere herein.

By "similar affinity", "similar on-rate" or "similar off-rate" is also meant that the binding affinity, on-rate or off-rate, as appropriate, of the antibody for human EpCAM and for one or more of the other species of interest (e.g. monkey or mouse) is comparable, e.g. is not more than a factor of 20 different. More preferably the difference between the binding affinities is less than a factor of 15, more preferably less than a factor of 10, most preferably less than a factor of 5, 4, 3 or 2.

It is believed that the antibodies of the invention may bind to a different epitope to the known anti-EpCAM antibodies which have been analysed. Certainly, the epitope appears to be different from the epitope of the MOC31 antibody, as the MOC31 epitope on human EpCAM is still present after subjecting EpCAM to reducing conditions, whereas the epitope of the preferred antibody of the present invention, 3-171, is apparently destroyed under such conditions (see Example 3). In addition, it appears that the epitope recognised by the antibodies of the invention, e.g. 3-171, may be different from the epitope recognised by the MT201 antibody. The results showing that the 3-17I antibody (and other antibodies of the invention) binds to both human and monkey EpCAM, whereas the MT201 antibody only binds to human EpCAM are indirect evidence of this.

Thus, a yet further embodiment of the invention provides an antibody, preferably an isolated antibody, more preferably a human antibody, which binds to an epitope in the extracellular domain of EpCAM and which has the ability to compete with the 3-17I antibody (i.e. an antibody comprising the VL of SEQ ID NO:4 and the VH of SEQ ID NO:3) as described herein, or the ability to compete with an antibody comprising the same CDRs as 3-171, i.e. an antibody comprising VL CDR sequences of SEQ ID NOs: 8, 9 and 10 and VH CDR sequences of SEQ ID NOs: 5, 6 and 7, for binding to EpCAM. Antibodies which compete with the 7-F17, 12-C15, 16-G5, 17-C20 or 24-G6 antibodies for binding to EpCAM are also preferred.

Binding to the same epitope/antigen can be readily tested by methods well known and described in the art, e.g. using binding assays, e.g. a competitive inhibition assay. Thus, a person skilled in the art will appreciate that binding assays can be used to identify other antibodies and antibody fragments with the same binding specificities as the antibodies and antibody fragments of the invention. As described below, a competition binding assay can be used to find such other antibodies. The method described below is only one example of a suitable competition assay. The skilled person will be aware of other suitable methods and variations.

Before a competition assay is performed using flow cytometry, some quantities of the tested antibody should be labeled, e.g. by biotinylation. The functionality (retention of the cell-binding properties) of the biotinylated product and the minimal concentration of the biotinylated antibody of the invention (Ab1) that gives sub-maximal binding against a fixed number of tumor cells, e.g. breast cancer cells, is determined. A total of $10^6$ cells are harvested from exponentially growing cultures and incubated with various antibody concentrations for 1 hr at 4° C. The cells are washed and incubated with a suitable detection antibody for an additional hour at 4° C. After washing, the cells are analyzed by flow cytometry. For each test antibody, a saturation curve is generated from the data by plotting median fluorescence intensity (MFI) against the antibody concentration.

For the competition assay, tumor cells, e.g. breast cancer cells, are prepared as above and treated in duplicate with a mixture of fixed concentration of labeled (biotinylated) antibody (bio-Ab1) and increasing concentrations of non-labeled competitive antibody. The fixed concentration is the minimal concentration of antibody that generates reasonable fluorescence signal against a fixed number of tumor cells as determined above. Ideally, this fixed concentration in nM should be below the affinity of the teated antibody at equilibrium ($K_D$). In this case the described method can be used for estimation of affinities of competitive antibodies (Schodin and Kranz, 1993, J Biol Chem 268: 25722-7). The antibody mixture is incubated with target cells for 1 hr at 4° C. The cells are washed and the cell binding of biotinylated antibody is revealed by incubation with FITC-labeled streptavidin. After subtracting the background fluorescence (PBS-5% FCS) from the median fluorescence reading for each test sample (bio-Ab1+Ab2), the percent of inhibition is calculated for each Ab2 concentration "c" according to the formula:

$$\% \text{ inhibition} = (1 - \text{MFI}^{bio-Ab1+Ab2\text{"}c\text{"}}/\text{MFI}^{bio-Ab1}) \times 100.$$

is calculated.

The percent inhibition is compared to a control value and a percent inhibition that has a statistically significant difference from the control percent inhibition indicates that the test antibody is capable of binding the same epitope/antigen. Preferably the statistically significant difference has a probability value of <0.05. Appropriate methods of determining statistical significance are well known and documented in the art and any of these may be used. Preferably, the test antibody reduces the amount of antibody of the invention that binds to EpCAM by at least about 95%.

Preferably, such antibodies have one or more of the other binding and functional properties as defined elsewhere herein, for example in points (a) to (j) above.

The antibodies of the invention bind to EpCAM. Thus the antibodies or binding proteins of the invention can be used to detect EpCAM in vivo or in vitro. As EpCAM is overexpressed on tumor cells, the antibodies or binding proteins of the invention can be used to detect tumor cells in vivo or in vitro. In addition, the ability of the antibodies to localize to tumor cells means that the antibodies of the invention can target body sites at which tumor cells are present, whereupon the antibody can act at the target site. For example, the antibody may induce an anti-tumor effect itself i.e. as a naked antibody, e.g. by activating or inducing ADCC or CDC. This ability to act as a naked Ab is extremely advantageous. Alternatively, or in addition, the antibody can induce an anti-tumor effect by virtue of being conjugated to an additional therapeutic molecule, e.g. a toxin or other anti-cancer molecule as described herein.

The antibodies of the invention preferably have the ability to induce ADCC of tumor cells in vitro, e.g. tumor cells which express EpCAM, e.g. breast cancer cells or gastric cancer cells, etc. A suitable in vitro test for ADCC is described in Example 4. Thus, the antibodies of the invention may for example cause at least 30%, 40%, 50%, 60%, 70%, 80% or 90% killing of tumor cells in vitro, e.g., in the presence of human PBMCs. Examples of appropriate tumor cells which can be used in such tests or assays are provided in Example 4, but generally any tumor cell which expresses EpCAM can be used. For example, the 3-17I antibody of the invention has been shown to have the ability to cause at least 30%, 40%, 50% or 60% killing of the breast cancer cell line BT-474 in vitro in the presence of human PBMCs; at least 30%, 40%, 50%, 60% or 70% killing of the breast cancer cell line MDA-MB-453 in vitro in the presence of human PBMCs and at least 30%, 40%, 50%, 60%, 70%, 80% or 90% killing of the breast cancer cell line MDA-MB-231 in vitro in the presence of human PBMCs. Such levels of killing are preferred for the antibodies of the invention. Such levels of killing are significantly higher than those observed for the current best anti-EpCAM antibody undergoing clinical trials (i.e. MT201), see Example 4.

The antibodies of the invention are preferably also shown to be particularly potent in terms of the low concentration of antibody required to achieve such ADCC levels. Again, a suitable in vitro test is described in Example 4. Thus, the antibody concentration required for half maximal cell lysis ($EC_{50}$) of tumor cells, e.g. breast cancer cells, in vitro is preferably less than 30 ng/ml, 25 ng/ml, 20 ng/ml, 15 ng/ml, 10 ng/ml, 5 ng/ml, 2 ng/ml, 1 ng/ml, 0.5 ng/ml or 0.25 ng/ml or 0.20 ng/ml or 0.15 ng/ml. For example, the 3-17I antibody of the invention has been shown to have an $EC_{50}$ of as low as 0.08 ng/ml for MDA-MB-453 cells, 0.12 ng/ml for B7474 cells and 15 ng/ml for MDA-MB-231 cells, all of which are significantly lower than the $EC_{50}$ values measured in parallel experiments for MT201. Again, these results show a clear superiority of the preferred antibodies of the present invention over the MT201 prior art antibody.

The antibodies of the invention preferably have the ability to induce CDC of tumor cells in vitro, e.g. tumor cells which express EpCAM, e.g. breast cancer cells or gastric cancer cells, etc. A suitable in vitro test for CDC is described in Example 4. Thus, the antibodies of the invention may for example cause at least 70%, 80%, 90%, 95% or even up to 100% killing of tumor cells in vitro, e.g., in the presence of human serum. Examples of appropriate tumor cells which can be used in such tests or assays are provided in Example 4 but generally any tumor cell which expresses EpCAM can be used. For example, the 3-17I antibody of the invention has been shown to have the ability to cause at least 70%, 80%, 90% or 95% killing of the breast cancer cell line MT-3 in vitro in the presence of human serum, indeed approximately 100% killing was shown; and to cause at least at least 70%, 80%, 90% or 95% killing of the gastric cancer cell line KATO III in vitro in the presence of human serum, indeed again approximately 100% killing was shown. Such levels of killing are preferred for the antibodies of the invention and are comparable to those observed for the current best anti-EpCAM antibody undergoing clinical trials (i.e. MT201), see Example 4.

The antibodies of the invention are preferably also shown to be particularly potent in terms of the low concentration of antibody required to achieve such CDC levels. Again, a suitable in vitro test is described in Example 4. Thus, the antibody concentration required for half maximal cell lysis ($EC_{50}$) of tumor cells, e.g. tumor cells which express EpCAM, e.g. breast cancer cells or gastric cancer cells, etc., in vitro is preferably less than 60 ng/ml, 50 ng/ml, 40 ng/ml, 30 ng/ml, 25 ng/ml, 20 ng/ml, 15 ng/ml, 10 ng/ml, 5 ng/ml, 2 ng/ml, 1 ng/ml, 0.75 ng/ml, 0.5 ng/ml, 0.4 ng/ml or 0.3 ng/ml. For example, the 3-17I antibody of the invention has been shown to have an $EC_{50}$ of as low as 0.28 ng/ml for KATO III cells and 0.38 ng/ml for MT-3 cells, all of which are significantly lower than the $EC_{50}$ values measured in parallel experiments for MT201. Again, these results show a clear superiority of the preferred antibodies of the present invention over the MT201 prior art antibody.

Thus, the antibodies of the invention show improved ATCC and CDC activity over at least the prior art antibody MT201, which is recognized as being particularly effective in this regard. Such an effect demonstrates that the antibodies of the invention may be used to recruit the patients' immune system to combat tumor cells (i.e. can be useful therapeutically without the need for an additional active agent). The ability to induce ATCC to such a high level and with such a high potency is clearly an advantagous property.

Thus, preferred antibodies of the invention have the ability to induce ADCC and/or CDC. ADCC and/or CDC activity may be assayed in vivo or in vitro.

Thus, preferred antibodies of the invention display anti-tumor activity. Such anti-tumor activity may be assayed in vitro or in vivo.

The antibodies of the invention preferably have the ability to inhibit the growth of tumor cells, e.g. breast cancer cells. Said inhibition might be demonstrated in vitro or in vivo.

Preferably, the above described abilities and properties are observed at a measurable or significant level and more preferably at a statistically significant level, when compared to appropriate control levels. Appropriate significance levels are discussed elsewhere herein. More preferably, one or more of the above described abilities and properties are observed at a level which is measurably better, or more preferably significantly better, when compared to the abilities observed for prior art antibodies.

Some antibodies are capable of being internalized into the cells to which they become bound. Thus, in some embodiments of the invention the antibodies are capable of being internalized. This property is particularly advantageous for use in immunoconjugates as any other agent attached to the antibody molecule should be internalized with the antibody molecule. In other embodiments no signficant internalization is seen.

In the following descriptions of the compositions, immunoconjugates, pharmaceuticals, combinations, cocktails, kits, first and second medical uses and all methods in accordance with this invention, the terms "antibody" and "immunoconjugate", or an antigen-binding region or fragment thereof, unless otherwise specifically stated or made clear from the scientific terminology, refer to a range of anti-Ep-CAM antibodies as well as to the specific 3-17I, 7-F17, 12-C15, 16-G5, 17-C20 or 24-G6 antibodies.

The terms "antibody" and "immunoglobulin", as used herein, refer broadly to any immunological binding agent or molecule that comprises a human antigen binding domain, including polyclonal and monoclonal antibodies. Depending on the type of constant domain in the heavy chains, whole antibodies are assigned to one of five major classes: IgA, IgD, IgE, IgG, and IgM and the antibodies of the invention may be in any one of these classes. Several of these are further divided into subclasses or isotypes, such as IgG1, IgG2, IgG3, IgG4, and the like. The heavy-chain constant domains that correspond to the difference classes of immunoglobulins are termed $\alpha$, $\delta$, $\epsilon$, $\gamma$ and $\mu$, respectively. The subunit structures and three-dimensional configurations of different classes of immunoglobulins are well known.

Generally, where whole antibodies rather than antigen binding regions are used in the invention, IgG and/or IgM are preferred because they are the most common antibodies in the physiological situation and because they are most easily made in a laboratory setting. In some embodiments however IgA antibodies are preferred.

The "light chains" of mammalian antibodies are assigned to one of two clearly distinct types: kappa ($\kappa$) and lambda ($\lambda$), based on the amino acid sequences of their constant domains and some amino acids in the framework regions of their variable domains. There is essentially no preference to the use of $\kappa$ or $\lambda$ light chain constant regions in the antibodies of the present invention.

As will be understood by those in the art, the immunological binding reagents encompassed by the term "antibody" extend to all human antibodies and antigen binding fragments thereof, including whole antibodies, dimeric, trimeric and multimeric antibodies; bispecific antibodies; chimeric antibodies; recombinant and engineered antibodies, and fragments thereof.

The term "antibody" is thus used to refer to any antibody-like molecule that has an antigen binding region, and this term includes antibody fragments that comprise an antigen binding domain such as Fab', Fab, F(ab')$_2$, single domain antibodies (DABs), T and Abs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa (lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like.

The techniques for preparing and using various antibody-based constructs and fragments are well known in the art (see Kabat et al., 1991, specifically incorporated herein by reference). Diabodies, in particular, are further described in EP 404, 097 and WO 93/11161; whereas linear antibodies are further described in Zapata et al. (1995).

Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, Fv, dsFv, Fd, dAbs, T and Abs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

The antibodies or antibody fragments can be produced naturally or can be wholly or partially synthetically produced. Thus the antibody may be from any appropriate source, for example recombinant sources and/or produced in transgenic animals or transgenic plants, or in eggs using the IgY technology. Thus, the antibody molecules can be produced in vitro or in vivo.

Preferably, the antibody or antibody fragment comprises an antibody light chain variable region ($V_L$) that comprises three CDR domains and an antibody heavy chain variable region ($V_H$) that comprises three CDR domains. Said VL and VH generally form the antigen binding site.

An "Fv" fragment is the minimum antibody fragment that contains a complete antigen-recognition and binding site.

This region has a dimer of one heavy chain and one light chain variable domain in tight, non-covalent association. It is in this configuration that the three hypervariable regions (CDRs) of each variable domain interact to define an antigen-binding site on the surface of the $V_H$-$V_L$ dimer. Collectively, the six hypervariable regions (CDRs) confer antigen-binding specificity to the antibody.

However, it is well documented in the art that the presence of three CDRs from the light chain variable domain and three CDRs from the heavy chain variable domain of an antibody is not necessary for antigen binding. Thus, constructs smaller than the above classical antibody fragment are known to be effective.

For example, camelid antibodies (Hamers-Casterman et al., 1993; Arbabi Ghahroudi et al., 1997) have an extensive antigen binding repertoire but are devoid of light chains. Also, results with single domain antibodies comprising VH domains alone (Ward et al., 1989; Davies and Riechmann, 1995) or VL domains alone (van den Beucken et al., 2001) show that these domains can bind to antigen with acceptably high affinities. Thus, three CDRs can effectively bind antigen.

It is also known that a single CDR, or two CDRs, can effectively bind antigen. As a first example, a single CDR can be inserted into a heterologous protein and confer antigen binding ability on the heterologous protein, as exemplified by showing that a VH CDR3 region inserted into a heterologous protein, such as GFP, confers antigen binding ability on the heterologous protein (Kiss et al., 2006; Nicaise et al., 2004).

It is further known that two CDRs can effectively bind antigen, and even confer superior properties than possessed by the parent antibody. For example, it has been shown (Qiu et al., 2007) that two CDRs from a parent antibody (a VH CDR1 and a VL CDR3 region) retain the antigen recognition properties of the parent molecule but have a superior capacity to penetrate tumors. Joining these CDR domains with an appropriate linker sequence (e.g., from VH FR2) to orientate the CDRs in a manner resembling the native parent antibody produced even better antigen recognition. Therefore, it is known in the art that it is possible to construct antigen binding antibody mimetics comprising two CDR domains (preferably one from a VH domain and one from a VL domain, more preferably, with one of the two CDR domains being a CDR3 domain) orientated by means of an appropriate framework region to maintain the conformation found in the parent antibody.

Thus, although preferred antibodies of the invention might comprise six CDR regions (three from a light chain and three from a heavy chain), antibodies with fewer than six CDR regions and as few as one or two CDR regions are encompassed by the invention. In addition, antibodies with CDRs from only the heavy chain or light chain are also contemplated.

Preferred antibodies of the invention that bind to EpCAM comprise at least one heavy chain variable region that comprises three CDRs and at least one light chain variable region that comprises three CDRs, wherein said heavy chain variable region comprises:

(c) a VH CDR3 that has the amino acid sequence of SEQ ID NO:7 or a sequence substantially homologous thereto; or (a) a variable heavy (VH) CDR1 that has the amino acid sequence of SEQ ID NO:5 or a sequence substantially homologous thereto, (b) a VH CDR2 that has the amino acid sequence of SEQ ID NO:6 or a sequence substantially homologous thereto, and (c) a VH CDR3 that has the amino acid sequence of SEQ ID NO:7 or a sequence substantially homologous thereto.

Six antibody clones are exemplified herein: 3-17I, 7-F17, 12-C15, 16-G5, 17-C20 and 24-G6, all of which bind to EpCAM and all of which share the same heavy chain CDR domains (a), (b) and (c). Seven other antibody clones were also identified which had the same heavy chain CDR domains and which bound to EpCAM. Thus, these heavy chain CDR domains are believed to be important for EpCAM binding. As the CDR3 domains of antibodies are often particularly important for antigen specificity, the presence of such a VH CDR3 domain based on SEQ ID NO:7 is particularly preferred in the antibodies of the invention.

Preferred light chain CDR regions for use in conjunction with the specified heavy chain CDR regions are described elsewhere herein. However, other light chain variable regions that comprise three CDRs for use in conjunction with the heavy chain variable regions of the invention are also contemplated. Appropriate light chain variable regions which can be used in combination with the heavy chain variable regions of the invention and which give rise to an antibody which binds EpCAM can be readily identified by a person skilled in the art.

For example, a heavy chain variable region of the invention can be combined with a single light chain variable region or a repertoire of light chain variable regions and the resulting antibodies tested for binding to EpCAM.

If desired, similar methods could be used to identify alternative heavy chain variable regions for use in combination with preferred light chain variable regions of the invention.

In certain embodiments, the antibody or antibody fragment comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region, or a portion thereof. Furthermore, the antibody or antibody fragment can comprise all or a portion of a kappa light chain constant region or a lambda light chain constant region, or a portion thereof. All or part of such constant regions may be produced naturally or may be wholly or partially synthetic. Appropriate sequences for such constant regions are well known and documented in the art. When a full complement of constant regions from the heavy and light chains are included in the antibodies of the invention, such antibodies are typically referred to herein as "full length" antibodies or "whole" antibodies Antibodies containing an Fc region are preferred for certain uses, particularly therapeutic uses in vivo, where the Fc region mediates effector functions such as ADCC and CDC.

The term "substantially homologous" as used herein in connection with an amino acid or nucleic acid sequence includes sequences having at least 70% or 75%, preferably at least 80%, and even more preferably at least 85%, 90%, 95%, 96%, 97%, 98% or 99%, sequence identity to the amino acid or nucleic acid sequence disclosed. Substantially homologous sequences of the invention thus include single or multiple base or amino acid alterations (additions, substitutions, insertions or deletions) to the sequences of the invention. At the amino acid level preferred substantially homologous sequences contain up to 5, e.g. only 1, 2, 3, 4 or 5, preferably 1, 2 or 3, more preferably 1 or 2, altered amino acids, in one or more of the framework regions and/or one or more of the CDRs making up the sequences of the invention. Said alterations can be with conservative or non-conservative amino acids. Preferably said alterations are conservative amino acid substitutions. In embodiments of the invention where certain residues are defined as X, then, where substantially homologous sequences are referred to, the amino acid substitutions of the substantially homologous sequences may be in residues other than the X residues, e.g. in 1, 2 or 3 residues other than the X residues, or the substitutions may be in the X residues, e.g. in 1, 2, or 3 of the X residues.

The substantially homologous nucleic acid sequences also include nucleotide sequences that hybridize to the nucleic acid sequences disclosed (or their complementary sequences), e.g., hybridize to nucleotide sequences encoding one or more of the light chain or heavy chain CDRs of the invention, the light or heavy chain variable regions of the invention, or the antibodies of the invention (or hybridize to their complementary sequences), under at least moderately stringent hybridization conditions.

The term "substantially homologous" also includes modifications or chemical equivalents of the amino acid and nucleotide sequences of the present invention that perform substantially the same function as the proteins or nucleic acid molecules of the invention in substantially the same way. For example, any substantially homologous antibody (or the substantially homologous nucleic acid encoding it) should retain the ability to bind to EpCAM as described above. Preferably, any substantially homologous antibody should retain the functional capabilities of the antibody, e.g. as defined elsewhere herein, for example the ability to bind to at least human and monkey EpCAM. Preferably, any substantially homologous antibody should retain the ability to specifically bind to the same epitope of EpCAM as recognized by the antibody in question, for example, the same epitope recognized by the CDR domains of the invention or the VH and VL domains of the invention as described herein. Binding to the same epitope/antigen can be readily tested by methods well known and described in the art, e.g., using binding assays, e.g., a competition assay. Retention of other functional properties can also readily be tested by methods well known and described in the art.

Thus, a person skilled in the art will appreciate that binding assays can be used to test whether "substantially homologous" antibodies have the same binding specificities as the antibodies and antibody fragments of the invention, for example, binding assays such as ELISA assays or BIAcore assays can readily be used to establish whether such "substantially homologous" antibodies can bind to EpCAM. As outlined below, a competition binding assay can be used to test whether "substantially homologous" antibodies retain the ability to specifically bind to substantially the same epitope of EpCAM as recognized by the antibodies of the invention, or have the ability to compete with one or more of the various antibodies of the invention (e.g. 3-171). The method described below is only one example of a suitable competition assay. The skilled person will be aware of other suitable methods and variations.

An exemplary competition assay involves assessing the binding of various effective concentrations of an antibody of the invention to EpCAM in the presence of varying concentrations of a test antibody (e.g., a substantially homologous antibody). The amount of inhibition of binding induced by the test antibody can then be assessed. A test antibody that shows increased competition with an antibody of the invention at increasing concentrations (i.e., increasing concentrations of the test antibody result in a corresponding reduction in the amount of antibody of the invention binding to EpCAM) is evidence of binding to substantially the same epitope. Preferably, the test antibody significantly reduces the amount of antibody of the invention that binds to EpCAM. Preferably, the test antibody reduces the amount of antibody of the invention that binds to EpCAM by at least about 95%. ELISA and flow cytometry assays are appropriate for assessing inhibition of binding in such a competition assay but other suitable techniques would be well known to a person skilled in the art.

Substantially homologous sequences of proteins of the invention include, without limitation, conservative amino acid substitutions, or for example alterations that do not effect the VH, VL or CDR domains of the antibodies, e.g., include scFv antibodies where a different linker sequence is used or antibodies where tag sequences or other components are added that do not contribute to the binding of antigen, or alterations to convert one type or format of antibody molecule or fragment to another type or format of antibody molecule or fragment (e.g., conversion from Fab to scFv or vice versa), or the conversion of an antibody molecule to a particular class or subclass of antibody molecule (e.g., the conversion of an antibody molecule to IgG or a subclass thereof, e.g., IgG1 or IgG3).

A "conservative amino acid substitution", as used herein, is one in which the amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., glycine, cysteine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Homology may be assessed by any convenient method. However, for determining the degree of homology between sequences, computer programs that make multiple alignments of sequences are useful, for instance Clustal W (Thompson et al., 1994). If desired, the Clustal W algorithm can be used together with BLOSUM 62 scoring matrix (Henikoff and Henikoff, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (1970), as revised by Smith and Waterman (1981) so that the highest order match is obtained between the two sequences and the number of identical amino acids is determined between the two sequences. Other methods to calculate the percentage identity between two amino acid sequences are generally art recognized and include, for example, those described by Carillo and Lipton (1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984) are also useful for this purpose. Furthermore, the Dali server at the European Bioinformatics institute offers structure-based alignments of protein sequences (Holm, 1993; 1995; 1998).

By way of providing a reference point, sequences according to the present invention having 70%, 75%, 80%, 85%, 90%, 95%, 96%, 97%, 98% or 99% homology, sequence identity etc. may be determined using the ALIGN program with default parameters (for instance available on Internet at the GENESTREAM network server, IGH, Montpellier, France).

By "at least moderately stringent hybridization conditions" it is meant that conditions are selected that promote selective hybridization between two complementary nucleic acid molecules in solution. Hybridization may occur to all or a portion of a nucleic acid sequence molecule. The hybridizing portion is typically at least 15 (e.g., 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(%(G+C)−600/l), or similar equation). Accordingly, the parameters in the wash conditions that determine hybrid stability are sodium ion concentration and temperature. In order to identify molecules that are similar, but not identical, to a known nucleic acid molecule, a 1% mismatch may be assumed to result in about a 1° C. decrease in Tm. For example, if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. By way of further example, sequences that "hybridize" are those sequences binding (hybridizing) under non-stringent conditions (e.g., 6×SSC, 50% formamide at room temperature) and washed under conditions of low stringency (e.g., 2×SSC, room temperature, more preferably 2×SSC, 42° C.) or conditions of higher stringency (e.g., 2×SSC, 65° C.) (where SSC=0.15M NaCl, 0.015M sodium citrate, pH 7.2).

It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

Generally speaking, sequences that hybridize under conditions of high stringency are preferred, as are sequences which, but for the degeneracy of the code, would hybridize under high stringency conditions.

In other preferred embodiments, second generation antibodies are provided that have enhanced or superior properties in comparison to an original anti-EpCAM antibody, such as 3-17I, 7-F17, 12-C15, 16-G5,17-C20 or 24-G6. For example, the second generation antibodies may have a different binding affinity or superior kinetic constants (e.g. on-rate and/or off-rate), a superior cross reactivity profile, superior ability to target tumor cells, e.g. an improved ability to induce ADCC or CDC, or an improved treatment of tumors in vivo, or a higher production level.

Comparisons to identify effective second generation antibodies are readily conducted and quantified, e.g., using one or more of the various assays described in detail herein or in the art. Second generation antibodies that have an enhanced biological property or activity of at least about 2-fold, 5-fold, 10-fold, 20-fold, and preferably, at least about 50-fold, in comparison to the anti-EpCAM antibodies of the present invention, as exemplified by the 3-17I antibody (or the antibodies 7-F17, 12-C15, 16-G5, 17-C20 or 24-G6), are encompassed by the present invention.

The antibody, binding protein and nucleic acid molecules of the invention are generally "isolated" or "purified" molecules insofar as they are distinguished from any such components that may be present in situ within a human or animal body or a tissue sample derived from a human or animal body. The sequences may, however, correspond to or be substantially homologous to sequences as found in a human or animal body. Thus, the term "isolated" or "purified" as used herein in reference to nucleic acid molecules or sequences and proteins or polypeptides, e.g., antibodies, refers to such molecules when isolated from, purified from, or substantially free of their natural environment, e.g., isolated from or purified from the human or animal body (if indeed they occur naturally), or refers to such molecules when produced by a technical process, i.e., includes recombinant and synthetically produced molecules.

Thus, when used in connection with a nucleic acid molecule, such terms may refer to a nucleic acid substantially free of material with which it is naturally associated such as other nucleic acids/genes or polypeptides. These terms may also refer to a nucleic acid substantially free of cellular material or culture medium when produced by recombinant DNA techniques, or substantially free of chemical precursors, or other chemicals when chemically synthesized. An isolated or purified nucleic acid may also be substantially free of sequences that naturally flank the nucleic acid (i.e., sequences located at the 5' and 3' ends of the nucleic acid) from which the nucleic acid is derived or sequences that have been made to flank the nucleic acid (e.g., tag sequences or other sequence that have no therapeutic value) by, for example, genetic engineering.

Thus, when used in connection with a protein or polypeptide molecule such as light chain CDRs 1, 2 and 3, heavy chain CDRs 1, 2 and 3, light chain variable regions, heavy chain variable regions, and binding proteins or antibodies of the invention, including full length antibodies, the term "isolated" or "purified" typically refers to a protein substantially free of cellular material or other proteins from the source from which it is derived. In some embodiments, particularly where the protein is to be administered to humans or animals, such isolated or purified proteins are substantially free of culture medium when produced by recombinant techniques, or chemical precursors or other chemicals when chemically synthesized. Such isolated or purified proteins may also be free of flanking sequences such as those described above for the isolated nucleic acid molecules.

The term "nucleic acid sequence" or "nucleic acid molecule" as used herein refers to a sequence of nucleoside or nucleotide monomers composed of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid molecules may be double stranded or single stranded. The nucleic acid molecules may be wholly or partially synthetic or recombinant.

In preferred embodiments the antibodies of the invention are human antibodies, more preferably fully human antibodies. In this regard, human antibodies generally have at least three potential advantages for use in human therapy. First, the human immune system should not recognize the antibody as foreign. Second, the half-life in the human circulation will be similar to naturally occurring human antibodies, allowing smaller and less frequent doses to be given. Third, because the effector portion is human, it will interact better with the other parts of the human immune system, e.g., to destroy target cells more efficiently by complement-dependent cytotoxicity (CDC) or antibody-dependent cellular cytotoxicity (ADCC).

However, although human antibodies are generally recognized to display these advantages, it is known that the development of human antibodies that have high enough affinities and appropriate functional properties to make them candidates for successful human therapy is by no means straightforward. The art therefore still lacks anti-EpCAM for the safe and effective treatment of humans, and poses challenges to the development of such agents.

The term "human" as used herein in connection with antibody molecules and binding proteins first refers to antibodies and binding proteins having variable regions (e.g., $V_H$, $V_L$, CDR or FR regions) and, optionally, constant antibody regions, isolated or derived from a human repertoire or derived from or corresponding to sequences found in humans, e.g., in the human germline or somatic cells. The 3-17I antibody (and the 7-F17, 12-C15, 16-G5, 17-C20 or 24-G6 antibodies) is an example of such a human antibody molecule wherein the variable regions have been isolated from a human repertoire.

The "human" antibodies and binding proteins of the invention further include amino acid residues not encoded by human sequences, e.g., mutations introduced by random or site directed mutations in vitro, for example mutations introduced by in vitro cloning or PCR. Particular examples of such mutations are mutations that involve conservative substitutions or other mutations in a small number of residues of the antibody or binding protein, e.g., in up to 5, e.g. in 5, 4, 3, 2 or 1 of the residues of the antibody or binding protein, preferably e.g., in up to 5, e.g. in 5, 4, 3, 2 or 1 of the residues making up one or more of the CDRs of the antibody or binding protein. Certain examples of such "human" antibodies include antibodies and variable regions that have been subjected to standard modification techniques to reduce the amount of potentially immunogenic sites.

Thus, the "human" antibodies of the invention include sequences derived from and related to sequences found in humans, but which may not naturally exist within the human antibody germline repertoire in vivo. In addition, the human antibodies and binding proteins of the present invention include proteins comprising human consensus sequences identified from human sequences, or sequences substantially homologous to human sequences.

In addition, the human antibodies and binding proteins of the present invention are not limited to combinations of $V_H$, $V_L$, CDR or FR regions that are themselves found in combination in human antibody molecules. Thus, the human antibodies and binding proteins of the invention can include or correspond to combinations of such regions that do not necessarily exist naturally in humans.

In preferred embodiments, the human antibodies will be fully human antibodies. "Fully human" antibodies, as used herein, are antibodies comprising "human" variable region domains and/or CDRs, as defined above, without substantial non-human antibody sequences or without any non-human antibody sequences. For example, antibodies comprising human variable region domains and/or CDRs "without substantial non-human antibody sequences" are antibodies, domains and/or CDRs in which up to 5, e.g. only about 5, 4, 3, 2 or 1 amino acids are amino acids that are not encoded by human antibody sequences. Thus, "fully human" antibodies are distinguished from "humanized" antibodies, which are based on substantially non-human variable region domains, e.g., mouse variable region domains, in which certain amino acids have been changed to better correspond with the amino acids typically present in human antibodies.

The "fully human" antibodies of the invention may be human variable region domains and/or CDRs without any other substantial antibody sequences, such as being single chain antibodies. Alternatively, the "fully human" antibodies of the invention may be human variable region domains and/or CDRs integral with or operatively attached to one or more human antibody constant regions. Certain preferred fully human antibodies are IgG antibodies with the full complement of IgG constant regions.

In other embodiments, "human" antibodies of the invention will be part-human chimeric antibodies. "Part-human chimeric" antibodies, as used herein, are antibodies comprising "human" variable region domains and/or CDRs operatively attached to, or grafted onto, all or part of a constant region of a non-human species, such as rat or mouse. Such part-human chimeric antibodies may be used, for example, in pre-clinical studies, wherein the constant region will preferably be of the same species of animal used in the pre-clinical testing. These part-human chimeric antibodies may also be used, for example, in ex vivo diagnostics, wherein the constant region of the non-human species may provide additional options for antibody detection.

The term "fragment" as used herein refers to fragments of biological relevance, e.g., fragments that contribute to antigen binding, e.g., form part of the antigen binding site, and/or contribute to the inhibition or reduction in function of the EpCAM antigen. Certain preferred fragments comprise a heavy chain variable region ($V_H$ domain) and/or a light chain variable region ($V_L$ domain) of the antibodies of the invention. Other preferred fragments comprise one or more of the heavy chain CDRs of the antibodies of the invention (or of the $V_H$ domains of the invention), or one or more of the light chain CDRs of the antibodies of the invention (or of the $V_L$ domains of the invention). Certain preferred fragments are at least 5 amino acids in length and comprise at least one CDR region, preferably a CDR3 region, more preferably a heavy chain CDR3 region.

In embodiments where the antibodies of the invention comprise a fragment of any of the defined sequences (for example comprise a fragment of SEQ ID NOs:21, 36, 49, 62, 75 or 88), e.g., are antibodies comprising $V_H$ and/or $V_L$ domains of the invention, or are antibodies or binding proteins comprising one or more CDRs of the invention, then these regions/domains are generally separated within the antibody or binding protein so that each region/domain can perform its biological function and so that the contribution to antigen binding is retained. Thus, the $V_H$ and $V_L$ domains are preferably separated by appropriate scaffold sequences/linker sequences and the CDRs are preferably separated by appropriate framework regions such as those found in naturally occurring antibodies and/or effective engineered antibodies. Thus, the $V_H$, $V_L$ and individual CDR sequences of the invention are preferably provided within or incorporated into an appropriate framework or scaffold to enable antigen binding. Such framework sequences or regions may correspond to naturally occurring framework regions, FR1, FR2, FR3 and/or FR4, as appropriate to form an appropriate scaffold, or may correspond to consensus framework regions, for example identified by comparing various naturally occurring framework regions. Alternatively, non-antibody scaffolds or frameworks, e.g., T cell receptor frameworks can be used.

Appropriate sequences that can be used for framework regions are well known and documented in the art and any of these may be used. Preferred sequences for framework regions are one or more (i.e. one, two, three or four) of the framework regions making up the $V_H$ and/or $V_L$ domains of the invention, i.e., one or more of the framework regions disclosed in SEQ ID NOs:21, 36, 49, 62, 75 or 88, or in Tables 1 to 6, or framework regions substantially homologous thereto, and in particular framework regions that allow the maintenance of antigen specificity, for example framework regions that result in substantially the same or the same 3D structure of the antibody. In certain preferred embodiments, all four of the variable light chain (SEQ ID NOs:15, 16, 17 and 18) and/or variable heavy chain (SEQ ID NOs:11, 12, 13 and 14), as appropriate, FR regions of SEQ ID NO:21 (also shown in Table 1), or FR regions substantially homologous thereto, are found in the antibodies of the invention. Other preferred combinations of variable light chain framework regions are shown in Tables 2 to 6.

In addition, although preferred antibodies of the invention are made up of $V_H$, $V_L$ or CDRs of the invention, it should be noted that the antibodies of the invention also encompass one or more $V_H$, $V_L$ or CDRs of the invention in combination with other $V_H$, $V_L$ or CDRs not of the invention, provided that the EpCAM binding properties or anti-EpCAM properties of the antibodies of the invention as outlined herein are still present.

The term "heavy chain complementarity determining region" ("heavy chain CDR") as used herein refers to regions of hypervariability within the heavy chain variable region ($V_H$ domain) of an antibody molecule. The heavy chain variable region has three CDRs termed heavy chain CDR1, heavy chain CDR2 and heavy chain CDR3 from the amino terminus to carboxy terminus. The heavy chain variable region also has four framework regions (FR1, FR2, FR3 and FR4 from the amino terminus to carboxy terminus). These framework regions separate the CDRs.

The term "heavy chain variable region" ($V_H$ domain) as used herein refers to the variable region of a heavy chain of an antibody molecule.

The term "light chain complementarity determining region" ("light chain CDR") as used herein refers to regions of hypervariability within the light chain variable region ($V_L$ domain) of an antibody molecule. Light chain variable regions have three CDRs termed light chain CDR1, light chain CDR2 and light chain CDR3 from the amino terminus to the carboxy terminus. The light chain variable region also has four framework regions (FR1, FR2, FR3 and FR4 from the amino terminus to carboxy terminus). These framework regions separate the CDRs.

The term "light chain variable region" ($V_L$ domain) as used herein refers to the variable region of a light chain of an antibody molecule.

It should be noted that the Kabat nomenclature is followed herein, where necessary, in order to define the positioning of the CDRs (Kabat et al., 1991, specifically incorporated herein by reference).

A person skilled in the art will appreciate that the proteins and polypeptides of the invention, such as the light and heavy CDRs, the light and heavy chain variable regions, antibodies, antibody fragments, and immunoconjugates, may be prepared in any of several ways well known and described in the art, but are most preferably prepared using recombinant methods.

Nucleic acid fragments encoding the light and heavy chain variable regions of the antibodies of the invention can be derived or produced by any appropriate method, e.g., by cloning or synthesis. Such sequences could, for example, be prepared by cloning appropriate sequences from e.g., human germ line genes and then making any necessary modifications to the germ line sequences to obtain the sequences of the invention using methods well known and described in the art. An alternative and more efficient method would be to synthesize the appropriate light or heavy chain variable region sequence as overlapping primers, and use primer extension to obtain the full sequence. This full sequence could then be amplified via PCR with primers containing appropriate restriction sites for further cloning and manipulation, e.g., for cloning into an appropriate expression vector. Five to seven overlapping primers per variable region are normally be sufficient, thereby making this technique very efficient and precise.

Once nucleic acid fragments encoding the light and heavy chain variable regions of the antibodies of the invention have been obtained, these fragments can be further manipulated by standard recombinant DNA techniques, for example to convert the variable region fragments into full length antibody molecules with appropriate constant region domains, or into particular formats of antibody fragment discussed elsewhere herein, e.g., Fab fragments, scFv fragments, etc. Typically, or as part of this further manipulation procedure, the nucleic acid fragments encoding the antibody molecules of the invention are generally incorporated into an appropriate expression vector in order to facilitate production of the antibodies of the invention.

Possible expression vectors include but are not limited to cosmids, plasmids, or modified viruses (e.g., replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner that allows expression of the nucleic acid.

The invention therefore contemplates a recombinant expression vector containing a nucleic acid molecule of the invention, or a fragment thereof, and the necessary regulatory sequences for the transcription and translation of the protein sequence encoded by the nucleic acid molecule of the invention.

Suitable regulatory sequences may be derived from a variety of sources, including bacterial, fungal, viral, mammalian, or insect genes (for example, see the regulatory sequences described in Goeddel, 1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene that facilitates the selection of host cells transformed or transfected with a recombinant molecule of the invention. Examples of selectable marker genes are genes encoding a protein such as neomycin and hygromycin that confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes that encode a fusion moiety that provides increased expression of the recombinant protein; increased solubility of the recombinant protein; and aid in the purification of the target recombinant protein by acting as a ligand in affinity purification (for example appropriate "tags" to enable purification and/or identification may be present, e.g., His tags or myc tags). For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g., a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofection, electroporation or microinjection. Suitable methods for transforming and transfecting host cells can be found in Sambrook et al., 1989, and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, 1990. In addition, the proteins of the invention may be expressed in prokaryotic cells, such as *Escherichia coli* (Zhang et al., 2004).

Yeast and fungi host cells suitable for carrying out the present invention include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., 1987), pMFa (Kurjan and Herskowitz, 1982), pJRy88 (Schultz et al., 1987), and pYES2 (Invitrogen Corporation, San Diego, Calif.). Protocols for the transformation of yeast and fungi are well known to those of ordinary skill in the art (see Hinnen et al., 1978; Ito et al., 1983, and Cullen et al. 1987).

Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), NS-1 cells, NS0 (ATCC CRL-11177), HEK-293 (human kidney, ATCC number CRL-11268) and Per.C6® (Crucell, Leiden, Netherlands. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., 1987) and pMT2PC (Kaufman et al., 1987).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., 1987, which reviews the use of *Agrobacterium rhizogenes* vectors; see also Zambryski et al., 1984, which describes the use of expression vectors for plant cells, including, among others, PAPS2022, PAPS2023, and PAPS2034).

Insect cells suitable for carrying out the present invention include cells and cell lines from *Bombyx, Trichoplusia* or *Spodotera* species. Baculovirus vectors available for expression of proteins in cultured insect cells (SF 9 cells) include the pAc series (Smith et al., 1983) and the pVL series (Luckow and Summers 1989). Some baculovirus-insect cell expression systems suitable for expression of the recombinant proteins of the invention are described in PCT/US/02442.

Alternatively, the proteins of the invention may also be expressed in non-human transgenic animals such as, rats, rabbits, sheep and pigs (Hammer et al. 1985; Palmiter et al. 1983; Brinster et al. 1985; Palmiter and Brinster 1985, and U.S. Pat. No. 4,736,866).

The proteins of the invention may also be prepared by chemical synthesis using techniques well known in the chemistry of proteins such as solid phase synthesis (Merrifield (1964); Frische et al., 1996) or synthesis in homogenous solution (Houbenweyl, 1987).

N-terminal or C-terminal fusion proteins comprising the antibodies and proteins of the invention conjugated to other molecules, such as proteins, may be prepared by fusing through recombinant techniques. The resultant fusion proteins contain an antibody or protein of the invention fused to the selected protein or marker protein, or tag protein as described herein. The antibodies and proteins of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins that may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Irrespective of the manner of preparation of a first anti-EpCAM antibody nucleic acid segment, further suitable antibody nucleic acid segments may be readily prepared by standard molecular biological techniques. In order to confirm that any variant, mutant or second generation anti-EpCAM antibody nucleic acid segment is suitable for use in the present invention, the nucleic acid segment will be tested to confirm expression of an anti-EpCAM antibody in accordance with the present invention. Preferably, the variant, mutant or second generation nucleic acid segment will also be tested to confirm hybridization under standard, more preferably, standard stringent hybridization conditions. Exemplary suitable hybridization conditions include hybridization in about 7% sodium dodecyl sulfate (SDS), about 0.5 M NaPO$_4$, about 1 mM EDTA at about 50° C.; and washing with about 1% SDS at about 42° C.

As a variety of antibodies may be readily prepared, the treatment methods of the invention may be executed by providing to the animal or patient at least a first nucleic acid segment or molecule that expresses a therapeutically effective amount of at least a first anti-EpCAM antibody of the invention in the patient. The "nucleic acid segment or molecule that expresses an anti-EpCAM antibody" will generally be in the form of at least an expression construct or vector, and may be in the form of an expression construct or vector comprised within a virus or within a recombinant host cell. Preferred gene therapy vectors of the present invention will generally be viral vectors, such as comprised within a recombinant retrovirus, herpes simplex virus (HSV), adenovirus, adeno-associated virus (AAV), cytomegalovirus (CMV), and the like.

A yet further aspect provides an expression construct or expression vector comprising one or more of the nucleic acid segments or molecules of the invention. Preferably the expression constructs or vectors are recombinant. Preferably said constructs or vectors further comprise the necessary regulatory sequences for the transcription and translation of the protein sequence encoded by the nucleic acid molecule of the invention.

A yet further aspect provides a host cell or virus comprising one or more expression constructs or expression vectors of the invention. Also provided are host cells or viruses comprising one or more of the nucleic acid molecules of the invention. A host cell or virus expressing an antibody of the invention forms a yet further aspect.

A yet further aspect of the invention provides a method of producing an antibody of the present invention comprising a step of culturing the host cells of the invention. Preferred methods comprise the steps of (i) culturing a host cell comprising one or more of the recombinant expression vectors or one or more of the nucleic acid sequences of the invention under conditions suitable for the expression of the encoded antibody or protein; and optionally (ii) isolating or obtaining the antibody or protein from the host cell or from the growth medium/supernatant. Such methods of production may also comprise a step of purification of the antibody or protein product and/or formulating the antibody or product into a composition including at least one additional component, such as a pharmaceutically acceptable carrier or excipient.

In embodiments when the antibody or protein of the invention is made up of more than one polypeptide chain (e.g., certain fragments such as Fab fragments), then all the polypeptides are preferably expressed in the host cell, either from the same or a different expression vector, so that the complete proteins, e.g., binding proteins of the invention, can assemble in the host cell and be isolated or purified therefrom.

The antibodies of the invention may also be used to produce further antibodies that bind to EpCAM. Such uses involve for example the addition, deletion, substitution or insertion of one or more amino acids in the amino acid sequence of a parent antibody to form a new antibody, wherein said parent antibody is one of the antibodies of the invention as defined elsewhere herein, and testing the resulting new antibody to identify antibodies that bind to EpCAM. Such methods can be used to form multiple new antibodies that can all be tested for their ability to bind EpCAM. Preferably said addition, deletion, substitution or insertion of one or more amino acids takes place in one or more of the CDR domains.

Such modification or mutation to a parent antibody can be carried out in any appropriate manner using techniques well known and documented in the art, for example by carrying out methods of random or directed mutagenesis. If directed mutagenesis is to be used then one strategy to identify appropriate residues for mutagenesis utilizes the resolution of the crystal structure of the binding protein-antigen complex, e.g., the Ab-Ag complex, to identify the key residues involved in the antigen binding (Davies and Cohen, 1996). Subsequently, those residues can be mutated to enhance the interaction. Alternatively, one or more amino acid residues can simply be targeted for directed mutagenesis and the effect on binding to EpCAM assessed.

Random mutagenesis can be carried out in any appropriate way, e.g., by error-prone PCR, chain shuffling or mutator E. coli strains.

Thus, one or more of the $V_H$ domains of the invention can be combined with a single $V_L$ domain or a repertoire of $V_L$ domains from any appropriate source and the resulting new antibodies tested to identify antibodies specific for EpCAM. Conversely, one or more of the $V_L$ domains of the invention can be combined with a single $V_H$ domain or repertoire of $V_H$ domains from any appropriate source and the resulting new antibodies tested to identify antibodies that bind to EpCAM.

Similarly, one or more, or preferably all three CDRs of the $V_H$ and/or $V_L$ domains of the invention can be grafted into a single $V_H$ and/or $V_L$ domain or a repertoire of $V_H$ and/or $V_L$ domains, as appropriate, and the resulting new antibodies tested to identify antibodies that bind to EpCAM.

The targeted mutations of the CDRs, especially CDR3 of the light and/or heavy chains, have been shown to be an effective technique for increasing antibody affinity and are preferred. Preferably, blocks of 3 to 4 amino acids of the CDR3 or specific regions called "hot-spots" are targeted for mutagenesis.

"Hot spots" are the sequences where somatic hypermutation takes place in vivo (and below Neuberger and Milstein, 1995). The hotspot sequences can be defined as consensus nucleotide sequences in certain codons. The consensus sequence is the tetranucleotide, RGYW, in which R can be either A or G, Y can be C or T and W can be either A or T (Neuberger and Milstein, 1995). In addition, the serine residues encoded by the nucleotides AGY are predominantly present in the CDRs regions of the variable domain over those encoded by TCN corresponding to a potential hot-spot sequences (Wagner et al., 1995).

Thus, the nucleotide sequence of the CDRs of the heavy and light chains of each antibody of the invention can be scanned for the presence of the hot-spot sequences and AGY codons. The identified hot-spots of the CDR regions of the light and heavy chain can then optionally be compared to the germinal sequences of the heavy and light chains using the International ImMunoGen Tics database (IMGT, http://imgt.cines.fr/textes/vquest/) (Davies et al., 1990). A sequence, identical to the germ line, suggest that somatic mutation has not occurred; therefore random mutations can be introduced mimicking the somatic events occurring in vivo or alternatively, site directed mutagenesis can be carried out, e.g., at the hot spots and/or AGY codons. In contrast, a different sequence shows that some somatic mutations have already occurred. It will remain to be determined if the in vivo somatic mutation was optimal.

Preferred hot-spots for mutation are those that code for exposed amino acids and preferably those that encode amino acids that form part of the antigen binding sites. Other preferred hot-spots for mutation are those that code for non-conserved amino acids. The hot-spots that code for buried or conserved amino acids within the CDRs are preferably not mutagenized. These residues are usually critical for the overall structure and are unlikely to interact with the antigen since they are buried.

Methods of carrying out the above described manipulation of amino acids and protein domains are well known to a person skilled in the art. For example, said manipulations could conveniently be carried out by genetic engineering at the nucleic acid level wherein nucleic acid molecules encoding appropriate binding proteins and domains thereof are modified such that the amino acid sequence of the resulting expressed protein is in turn modified in the appropriate way.

The new antibodies produced by these methods will preferably have improved functional properties, e.g. a higher or enhanced affinity (or at least an equivalent affinity) for EpCAM as the parent antibodies, and can be treated and used in the same way as the antibodies of the invention as described elsewhere herein (e.g., for therapy, diagnosis, in compositions etc). Alternatively, or additionally, the new antibodies will have one or more other improved functional properties as described elsewhere herein.

New antibodies produced, obtained or obtainable by these methods form a yet further aspect of the invention.

Testing the ability of one or more antibodies to bind to EpCAM can be carried out by any appropriate method, which are well known and described in the art. EpCAM samples, for example recombinant EpCAM from various species, are commercially available (e.g. from R&D Systems Inc, Minneapolis, Minn., USA) or can readily be generated from the sequence information for EpCAM molecules available in the art (see the Examples) and these can readily be used to assay binding, for example by conventional methods such as ELISA, BIAcore, etc., in which for example EpCAM is attached to a solid support and the ability of antibodies to bind thereto is measured by standard techniques. Alternatively, binding to EpCAM can be assessed by Western blot. EpCAM samples comprising the extracellular domain of EpCAM are ideally used for these purposes.

Alternatively, cells which express high levels of EpCAM (e.g. gastric carcinoma lines such as Kato III, breast cancer cell lines such as MT-3, BT474, MDA-MB-453 and MDA-MB-231) or have been engineered to express high levels of EpCAM can be used to assess for antibodies which bind to EpCAM, e.g. using flow cytometry or IHC.

Appropriate ELISA, Western Blot and BIAcore assays are described in the Examples. In any assay, an ability of an antibody to bind to EpCAM, e.g. to EpCAM of a particular species, generally refers to the ability of an antibody to show measurable and preferably significant binding to EpCAM compared to an appropriate control, e.g. an antibody which does not bind to EpCAM. For an antibody to be considered as not binding to EpCAM, e.g. to EpCAM of a particular species, then generally such antibodies show insignificant or undetectable or unmeasurable binding to EpCAM, for example at a level which is not measurably or significantly higher or different than that of an appropriate control, e.g. an antibody which does not bind to EpCAM.

In any statistical analysis referred to herein, preferably the statistically significant difference over a relevant control has a probability value of <0.1, preferably <0.05, more preferably <0.01. Appropriate methods of determining statistical significance are well known and documented in the art and any of these may be used.

This invention further provides compositions comprising at least one antibody or antibody fragment of the invention, optionally including a diluent. Such compositions may be pharmaceutically acceptable compositions or compositions for use in laboratory studies. In terms of the pharmaceutical compositions, they may preferably be formulated for parenteral administration, such as for intravenous or even subcutaneous administration.

The present invention provides a number of methods and uses of the human antibodies and antibody fragments of the invention. Concerning all methods, the terms "a" and "an" are used to mean "at least one", "at least a first", "one or more" or "a plurality" of steps in the recited methods, except where specifically stated. This is particularly relevant to the administration steps in the treatment methods. Thus, not only may different doses be employed with the present invention, but different numbers of doses, e.g., injections, may be used, up to and including multiple injections. Combined therapeutics may be used, administered before, after or during administration of the anti-EpCAM therapeutic antibody.

Various useful in vitro methods and uses of the antibodies or immunoconjugates of the invention are provided that have important biological implications. First provided are methods of, and uses in, binding EpCAM, which generally comprise effectively contacting a composition comprising EpCAM (or suspected of comprising EpCAM) with at least a first anti-EpCAM antibody of the invention, or antigen-binding fragment thereof. The antibodies of the invention, or immunoconjugates thereof, can thus be used in binding assays. Suitably useful binding assays thus include those commonly employed in the art, such as in immunoblots, Western blots, dot blots, RIAs, ELISAs, immunohistochemistry, fluorescent activated cell sorting (FACS), immunoprecipitation, affinity chromatography, and the like.

Methods of, and uses in, detecting EpCAM are provided, which generally comprise contacting a composition suspected of containing EpCAM with at least a first antibody or immunoconjugate of the invention, or antigen-binding fragment thereof, under conditions effective to allow the formation of EpCAM/antibody complexes and detecting the complexes so formed. The detection methods and uses may be used in connection with biological samples, e.g., in diagnostics for tumors, and diagnostic kits based thereon are also provided.

The methods and uses of the present invention are particularly intended for use in animals and patients that have, or are at risk for developing, any disease or condition associated with EpCAM or in which EpCAM plays a biological role, e.g. diseases associated with the presence or overexpression of EpCAM or aberrant activity of EpCAM, e.g. where inhibition of EpCAM activity might be advantageous. Preferred examples are cancers or carcinomas, preferably one or more cancers or carcinomas selected from the group consisting of breast, colorectal, prostate, ovary, bladder, gallbladder, pancreas, lung, gastric tissue or organs (e.g. stomach, esophagus), liver (e.g. hepatocellular carcinoma), kidney (e.g. renal cell carcinoma), skin neoplasms, head and neck (e.g. glioma), lips, mouth, vagina and cervix. Any reference to "tumor(s)" herein also refers to "cancer(s)" or "carcinoma(s)". Metastatic cancers can also be treated, as can the reduction of metastases from a primary tumor. Especially, so-called minimal residual disease (MRD), which is left in post-surgery patients, is amenable for immunotherapy with anti-EpCAM antibodies.

Patients which have tumors which show detectable levels, preferably high detectable levels of EpCAM expression are likely to be particularly appropriate for therapy with the anti-EpCAM antibodies of the invention. In addition, patients with tumors which do not express very high levels of Her-2 and are thus not ideal candidates for Herceptin therapy might be particularly appropriate for such anti-EpCAM therapy. Tumors can be tested for expression levels by appropriate methods well known in the art.

The present invention thus further provides methods of, and uses in, treating a disease as defined above, comprising administering to an animal or patient with such a disease, a therapeutically effective amount of an anti-EpCAM antibody of the invention, or an antigen-binding fragment or immunoconjugate of such an anti-EpCAM antibody.

A yet further aspect of the invention provides the use of the antibodies of the invention or an antigen-binding fragment or immunoconjugate of such an antibody in the manufacture of a composition or medicament for use in therapy, imaging or diagnosis.

A yet further aspect provides the antibodies of the invention or an antigen-binding fragment or immunoconjugate of such an antibody for use in therapy, diagnosis or imaging.

In addition, the invention provides compositions comprising the antibodies of the invention or an antigen-binding fragment or immunoconjugate of such an antibody with one or more pharmaceutically acceptable excipient, carrier, diluent, buffer or stabilizer.

The in vivo methods as described herein are generally carried out in a mammal. Any mammal may be treated, for example humans and any livestock, domestic or laboratory animal. Specific examples include mice, rats, pigs, cats, dogs, sheep, rabbits, cows and monkeys. Preferably, however, the mammal is a human.

Thus, the term "animal" or "patient" as used herein includes any mammal, for example humans and any livestock, domestic or laboratory animal. Specific examples include mice, rats, pigs, cats, dogs, sheep, rabbits, cows and monkeys. Preferably, however, the animal or patient is a human subject.

This invention links both anti-cancer methods using unconjugated or naked antibodies and fragments thereof, and cancer targeting methods using immunoconjugates in which an antibody of the invention or antigen-binding fragment thereof, is operatively attached to a therapeutic agent or diagnostic agent. Unless otherwise specifically stated or made clear in scientific terms, the terms "antibody and fragment thereof", as used herein, therefore mean an "unconjugated or naked" antibody or fragment, which is not attached to another agent, particularly a therapeutic or diagnostic agent. These definitions do not exclude modifications of the antibody, such as, by way of example only, modifications to improve the biological half life, affinity, avidity or other properties of the antibody, or combinations of the antibody with other effectors.

The anti-cancer treatment methods and uses of the invention also encompass the use of both unconjugated or naked antibodies and immunoconjugates. In the immunoconjugate-based anti-cancer treatment methods, an antibody of the invention, or antigen-binding fragment thereof, is preferably operatively attached to a second anti-cancer agent (the anti-EpCAM antibody itself, being the first anti-cancer agent). The attached anti-cancer agents may be those that have a direct or indirect anti-cancer effect.

The foregoing treatment methods and uses will generally involve the administration of the pharmaceutically effective composition to the animal or patient systemically, such as by transdermal, intramuscular, intravenous injection and the like. However, any route of administration that allows the therapeutic agent to localize to the tumor site or sites, will be acceptable. Therefore, other suitable routes of delivery include oral, nasal or respiratory and topical.

"Administration", as used herein, means provision or delivery of anti-EpCAM antibody therapeutics in an amount(s) and for a period of time(s) effective to exert therapeutic, e.g. anti-tumor effects. The passive administration of proteinaceous therapeutics is generally preferred, in part, for its simplicity and reproducibility.

However, the term "administration" is herein used to refer to any and all means by which anti-EpCAM antibodies of the invention are delivered or otherwise provided to the tumor. "Administration" therefore includes the provision of cells that produce the anti-EpCAM antibody of the invention in a manner effective to result in delivery to the tumor. In such embodiments, it may be desirable to formulate or package the cells in a selectively permeable membrane, structure or implantable device, generally one that can be removed to cease therapy. Exogenous anti-EpCAM antibody of the invention will still generally be preferred, as this represents a non-invasive method that allows the dose to be closely monitored and controlled.

The therapeutic methods and uses of the invention also extend to the provision of nucleic acids that encode an anti-EpCAM antibody of the invention in a manner effective to result in their expression in the vicinity of the tumor or their localization to the tumor. Any gene therapy technique may be employed, such as naked DNA delivery, recombinant genes and vectors, cell-based delivery, including ex vivo manipulation of patients' cells, and the like.

The anti-EpCAM antibodies of the invention can also be used to deliver other therapeutic or diagnostic agents to tumors. In such embodiments, the other therapeutic or diagnostic agents are generally operatively attached to the anti-EpCAM antibodies of the invention.

The terms "therapy" or "treatment" as used herein include prophylactic therapy, which may result in the prevention of disease. The terms "therapy" and "treatment" include combating or cure of disease but also include the controlling, reduction or alleviation of disease or one or more of the symptoms associated therewith. The antibodies of the invention may also be used in prognostic applications, e.g. for diseases in which EpCAM levels are altered. Thus, the antibodies of the present invention can be used to prognose cancer.

The "therapeutically effective amounts" for use in the invention are amounts of anti-EpCAM antibody of the invention, or immunoconjugates thereof, effective to specifically kill at least a portion of tumor cells; to specifically induce apoptosis in at least a portion of tumor cells; to specifically induce necrosis in at least a portion of a tumor; and/or to induce tumor regression or remission upon administration to animals or patients. Such effects are preferably achieved while exhibiting little or no binding to, or little or no killing of cells in normal, healthy tissues; and exerting negligible or manageable adverse side effects on normal, healthy tissues of the animal or patient.

The terms "preferentially" and "specifically", as used herein in the context of killing or inducing apoptosis or of inducing necrosis of tumor cells or of inducing tumor regression or remission, thus mean that the anti-EpCAM antibody of the invention or immunoconjugates thereof, function to achieve tumor destruction and/or tumor necrosis that is substantially confined to the tumor site, and does not substantially extend to causing destruction and/or tissue necrosis in normal, healthy tissues of the animal or subject. The structure and function of healthy cells and tissues is therefore maintained substantially unimpaired by the practice of the invention.

Anti-EpCAM antibodies of the invention or therapeutic conjugates are preferably linked to one or more radiotherapeutic agents, chemotherapeutic agents, anti-angiogenic agents, apoptosis-inducing agents, anti-tubulin drugs, anti-cellular or cytotoxic agents, steroids, cytokines, chemokines, ATPase inhibitors, other antibodies (e.g. as bispecific antibodies or diabodies) or coagulants (coagulation factors).

The invention thus provides a range of conjugated antibodies and fragments thereof in which the anti-EpCAM antibody is operatively attached to at least one other therapeutic or diagnostic agent. The term "immunoconjugate" is broadly used to define the operative association of the antibody with another effective agent and is not intended to refer solely to any type of operative association, and is particularly not limited to chemical "conjugation". Recombinant fusion proteins are particularly contemplated. So long as the delivery or targeting agent is able to bind to the target and the therapeutic or diagnostic agent is sufficiently functional upon delivery, the mode of attachment will be suitable.

Attachment of agents via the carbohydrate moieties on antibodies is also contemplated. Glycosylation, both O-linked and N-linked, naturally occurs in antibodies. Recombinant antibodies can be modified to recreate or create additional glycosylation sites if desired, which is simply achieved by engineering the appropriate amino acid sequences (such as Asn-X-Ser, Asn-X-Thr, Ser, or Thr where X is not Pro) into the primary sequence of the antibody.

Currently preferred agents for use in anti-EpCAM antibody or therapeutic conjugates of the invention and related methods and uses are those that complement or enhance the effects of the antibody and/or those selected for a particular tumor type or patient. "Therapeutic agents that complement or enhance the effects of the antibody" include radiotherapeutic agents, chemotherapeutic agents, anti-angiogenic agents, apoptosis-inducing agents, anti-tubulin drugs, anti-cellular or cytotoxic agents, steroids, coagulants, cytokines, chemokines, ATPase inhibitors, other antibodies, (e.g. as bispecific antibodies or diabodies), any one or more of which are preferred for use herewith.

Currently preferred anti-angiogenic agents include angiostatin, endostatin, any one of the angiopoietins, vasculostatin, canstatin and maspin.

"Anti-tubulin drug(s)", as used herein, means any agent, drug, prodrug or combination thereof that inhibits cell mitosis, preferably by directly or indirectly inhibiting tubulin activities necessary for cell mitosis, preferably tubulin polymerization or depolymerization. Currently preferred anti-tubulin drugs include colchicine, taxol, vinblastine, vincristine, vindescine and one or more of the combretastatins.

The attachment or association of the preferred agents with anti-EpCAM antibodies of the invention gives "immunoconjugates", wherein such immunoconjugates often have enhanced and even synergistic anti-tumor properties.

Antibody-drug conjugates (ADC) e.g. with auristatins, calicheamicin maytansinoids or alkylating agents are also appropriate for use in the present invention.

The use of anti-cellular and cytotoxic agents results in anti-EpCAM antibody "immunotoxins" of the invention, whereas the use of coagulation factors results in anti-EpCAM antibody "coaguligands" of the invention.

The use of at least two therapeutic agents is also contemplated, such as combinations of one or more radiotherapeutic agents, chemotherapeutic agents, anti-angiogenic agents, apoptosis-inducing agents, anti-tubulin drugs, anti-cellular and cytotoxic agents, steroids, cytokines, chemokines, ATPase inhibitors, other antibodies, (e.g. as bispecific antibodies or diabodies) and coagulation factors.

In certain applications, the anti-EpCAM antibody therapeutics of the invention will be operatively attached to cytotoxic, cytostatic or otherwise anti-cellular agents that have the ability to kill or suppress the growth or cell division of cells. Suitable anti-cellular agents include chemotherapeutic agents, as well as cytotoxins and cytostatic agents. Cytostatic agents are generally those that disturb the natural cell cycle of a target cell, preferably so that the cell is taken out of the cell cycle.

Exemplary chemotherapeutic agents include: hormones, such as steroids; cytokines; anti-metabolites, such as cytosine arabinoside, fluorouracil, methotrexate or aminopterin; anthracyclines; mitomycin C; vinca alkaloids; antibiotics; demecolcine; etoposide; mithramycin; and anti-tumor alkylating agents, such as chlorambucil or melphalan. Certain preferred anti-cellular agents are DNA synthesis inhibitors, such as daunorubicin, doxorubicin/adriamycin, and the like. Overall, taxol/paclitaxel, docetaxel, cisplatin, gemcitabine, a combretastatin and doxorubicin/adriamycin are currently preferred anti-cancer agents.

Of the cytokines and chemokines, currently preferred agents are IL-2, IL-12, TNF-α, interferon-α (IFN-α), IFN-β, IFN-γ, GM-CSF and LEC (liver-expressed chemokine). V-type ATPase inhibitors are also currently preferred, such as salicylihalamide, concanamycin or bafilomycin, as are protein synthesis inhibitors, such as psymberin, pederin, irciniastatin A.

In certain therapeutic applications, toxin moieties will be preferred, due to the much greater ability of most toxins to deliver a cell killing effect, as compared to other potential agents. Therefore, certain preferred anti-cellular agents for anti-EpCAM antibody constructs of the invention are plant-, fungus- or bacteria-derived toxins. Exemplary toxins include epipodophyllotoxins; bacterial endotoxin or the lipid A moiety of bacterial endotoxin; ribosome inactivating proteins, such as saporin or gelonin; a-sarcin; aspergillin; restrictocin; ribonucleases, such as placental ribonuclease; diphtheria toxin and pseudomonas exotoxin. Currently preferred examples are ricin, gelonin, abrin, diphtheria, pseudomonas and pertussis toxins.

Certain preferred toxins are the A chain toxins, such as ricin A chain. The most preferred toxin moiety is often ricin A chain that has been treated to modify or remove carbohydrate residues, so called "deglycosylated A chain" (dgA). Deglycosylated ricin A chain is preferred because of its extreme potency, longer half-life, and because it is economically feasible to manufacture it a clinical grade and scale. Recombinant and/or truncated ricin A chain may also be used.

The anti-EpCAM antibody therapeutics of the invention may comprise a component that is capable of promoting coagulation, i.e., a coagulant. Here, the targeting antibody may be directly or indirectly, e.g., via another antibody, linked to a factor that directly or indirectly stimulates coagulation.

Preferred coagulation factors for such uses are Tissue Factor (TF) and TF derivatives, such as truncated TF (tTF), dimeric, trimeric, polymeric/multimeric TF, and mutant TF deficient in the ability to activate Factor VII. Other suitable coagulation factors include vitamin K-dependent coagulants, such as Factor II/IIa, Factor VII/VIIa, Factor IX/IXa and Factor X/Xa; vitamin K-dependent coagulation factors that lack the GIa modification; Russell's viper venom Factor X activator; platelet-activating compounds, such as thromboxane $A_2$ and thromboxane $A_2$ synthase; and inhibitors of fibrinolysis, such as $\alpha$2-antiplasmin. Overall, truncated Tissue Factor (tTF) is currently preferred.

The preparation of immunoconjugates and immunotoxins is generally well known in the art (see, e.g., U.S. Pat. No. 4,340,535). Each of the following patents are further incorporated herein by reference for the purposes of even further supplementing the present teachings regarding immunotoxin generation, purification and use: U.S. Pat. Nos. 6,004,554; 5,855,866; 5,965,132; 5,776,427; 5,863,538; 5,660,827 and 6,051,230.

A variety of chemotherapeutic and other pharmacological agents can also be successfully conjugated to anti-EpCAM antibody therapeutics of the invention. Exemplary antineoplastic agents that have been conjugated to antibodies include doxorubicin, daunomycin, methotrexate and vinblastine. Moreover, the attachment of other agents such as neocarzinostatin, macromycin, trenimon and $\alpha$-amanitin has been described (see U.S. Pat. Nos. 5,660,827; 5,855,866; and 5,965,132; each incorporated herein.)

The preparation of coaguligands is also easily practiced. The operable association of one or more coagulation factors with an anti-EpCAM antibody of the invention may be a direct linkage, such as those described above for the immunotoxins. Alternatively, the operative association may be an indirect attachment, such as where the antibody is operatively attached to a second binding region, preferably an antibody or antigen binding region of an antibody, which binds to the coagulation factor. The coagulation factor should be attached to the anti-EpCAM antibody of the invention at a site distinct from its functional coagulating site, particularly where a covalent linkage is used to join the molecules.

Bispecific or trispecific antibodies may also be employed in the methods of the invention. In such antibodies one arm binds to EpCAM and is an antibody of the present invention. Some preferred examples of specifities for the other arm(s) of the bispecific or trispecific antibodies are anti-CD3, —CD16, —CD28, —NKG2D, NKp30, NKp44, NKp46 or anti-VEGF to block tumor vascularization. Methods for preparing bispecific antibodies are well known and described in the art.

In the preparation of immunoconjugates, immunotoxins and coaguligands, recombinant expression may be employed. The nucleic acid sequences encoding the chosen anti-EpCAM antibody of the invention, and therapeutic agent, toxin or coagulant, are attached in-frame in an expression vector. Recombinant expression thus results in translation of the nucleic acid to yield the desired immunoconjugate. Chemical cross-linkers and avidin:biotin bridges may also join the therapeutic agents to the anti-EpCAM antibody of the invention.

The compositions and methods of the present invention may be used in combination with other therapeutics and diagnostics. In terms of biological agents, preferably diagnostic or therapeutic agents, for use "in combination" with an anti-EpCAM antibody in accordance with the present invention, the term "in combination" is succinctly used to cover a range of embodiments. The "in combination" terminology, unless otherwise specifically stated or made clear from the scientific terminology, thus applies to various formats of combined compositions, pharmaceuticals, cocktails, kits, methods, and first and second medical uses.

The "combined" embodiments of the invention thus include, for example, where the anti-EpCAM of the invention is a naked antibody and is used in combination with an agent or therapeutic agent that is not operatively attached thereto. In such cases, the agent or therapeutic agent may be used in a non-targeted or targeted form. In "non-targeted form", the agent, particularly therapeutic agents, will generally be used according to their standard use in the art. In "targeted form", the agent will generally be operatively attached to a distinct antibody or targeting region that delivers the agent or therapeutic agent to the angiogenic disease site or tumor. The use of such targeted forms of biological agents, both diagnostics and therapeutics, is also quite standard in the art.

In other "combined" embodiments of the invention, the anti-EpCAM antibody of the invention is an immunoconjugate wherein the antibody is itself operatively associated or combined with the agent or therapeutic agent. The operative attachment includes all forms of direct and indirect attachment as described herein and known in the art.

The "combined" uses, particularly in terms of an anti-EpCAM antibody of the invention in combination with therapeutic agents, also include combined compositions, pharmaceuticals, cocktails, kits, methods, and first and second medical uses wherein the therapeutic agent is in the form of a prodrug. In such embodiments, the activating component able to convert the prodrug to the functional form of the drug may again be operatively associated with the anti-EpCAM antibodies of the present invention.

In certain preferred embodiments, the therapeutic compositions, combinations, pharmaceuticals, cocktails, kits, methods, and first and second medical uses will be "prodrug combinations". As will be understood by those of ordinary skill in the art, the term "prodrug combination", unless otherwise stated, means that the antibody of the invention is operatively attached to a component capable of converting the prodrug to the active drug, not that the antibody is attached to the prodrug itself. However, there is no requirement that the prodrug embodiments of the invention need to be used as prodrug combinations. Accordingly, prodrugs may be used in any manner that they are used in the art, including in ADEPT and other forms.

Thus, where combined compositions, pharmaceuticals, cocktails, kits, methods, and first and second medical uses are described, preferably in terms of diagnostic agents, and more preferably therapeutic agents, the combinations include anti-EpCAM antibodies that are naked antibodies and immunoconjugates, and wherein practice of the in vivo embodiments of the invention involves the prior, simultaneous or subsequent administration of the naked antibodies or immunoconjugate and the biological, diagnostic or therapeutic agent; so long as, in some conjugated or unconjugated form, the overall provision of some form of the antibody and some form of the biological, diagnostic or therapeutic agent is achieved.

The foregoing and other explanations of the effects of the present invention on tumors are made for simplicity to explain the combined mode of operation, type of attached agent(s) and such like. This descriptive approach should not be interpreted as either an understatement or an oversimplification of the beneficial properties of the anti-EpCAM antibodies of the invention. It will therefore be understood that such antibodies themselves have anti-tumor properties and that immunoconjugates of such antibodies will maintain these properties and combine them with the properties of the attached agent; and further, that the combined effect of the antibody and any attached agent will typically be enhanced and/or magnified.

The invention therefore provides compositions, pharmaceutical compositions, therapeutic kits and medicinal cocktails comprising, optionally in at least a first composition or container, a therapeutically effective amount of at least a first anti-EpCAM antibody of the invention, or an antigen-binding fragment or immunoconjugate of such an anti-EpCAM antibody; and a therapeutically effective amount of at least a second biological agent, component or system.

The "at least a second biological agent, component or system" will often be a therapeutic or diagnostic agent, component or system, but it need not be. For example, the at least a second biological agent, component or system may comprise components for modification of the antibody and/or for attaching other agents to the antibody. Certain preferred second biological agents, components or systems are prodrugs or components for making and using prodrugs, including components for making the prodrug itself and components for adapting the antibodies of the invention to function in such prodrug or ADEPT embodiments.

Where therapeutic or diagnostic agents are included as the at least a second biological agent, component or system, such therapeutics and/or diagnostics will typically be those for use in connection with cancer treatment or diagnosis.

Thus, in certain embodiments "at least a second anti-cancer agent" will be included in the therapeutic kit or cocktail. The term "at least a second anti-cancer agent" is chosen in reference to the anti-EpCAM antibody of the invention being the first anti-cancer agent. The antibodies of the invention may thus be combined with chemotherapeutic agents, radiotherapeutic agents, cytokines, anti-angiogenic agents, apoptosis-inducing agents or anti-cancer immunotoxins or coaguligands, some examples of which are discussed elsewhere herein.

Other exemplary anti-cancer agent include, e.g., neomycin, podophyllotoxin(s), TNF-$\alpha$, $\alpha_v\beta_3$ antagonists, calcium ionophores, calcium-flux inducing agents, and any derivative or prodrug thereof. Currently preferred anti-tubulin drugs include colchicine, taxol, vinblastine, vincristine, vindescine, a combretastatin or a derivative or prodrug thereof.

In terms of compositions, kits and/or medicaments of the invention, the combined effective amounts of the therapeutic agents may be comprised within a single container or container means, or comprised within distinct containers or container means. The cocktails will generally be admixed together for combined use. Agents formulated for intravenous administration will often be preferred. Imaging components may also be included. The kits may also comprise instructions for using the at least a first antibody and the one or more other biological agents included.

Speaking generally, the at least a second anti-cancer agent (or any other second agent) may be administered to the animal or patient substantially simultaneously with the anti-EpCAM antibody of the invention; such as from a single pharmaceutical composition or from two pharmaceutical compositions administered closely together.

Alternatively, the at least a second anti-cancer agent (or any other second agent) may be administered to the animal or patient at a time sequential to the administration of the anti-EpCAM antibody of the invention. "At a time sequential", as used herein, means "staggered", such that the at least a second anti-cancer agent is administered to the animal or patient at a time distinct to the administration of the anti-EpCAM antibody of the invention. Generally, the two agents are administered at times effectively spaced apart to allow the two agents to exert their respective therapeutic effects, i.e., they are administered at "biologically effective time intervals". The at least a second anti-cancer agent (or other second agent) may be administered to the animal or patient at a biologically effective time prior to the anti-EpCAM antibody of the invention, or at a biologically effective time subsequent to that therapeutic.

Accordingly, the present invention provides methods for treating an animal or patient with a tumor, comprising:
(a) subjecting the animal or patient to a first treatment that substantially reduces the tumor burden; and
(b) subsequently administering at least a first anti-EpCAM antibody of the invention, or antigen-binding fragment thereof, or immunoconjugate thereof; optionally wherein the antibody or fragment is operatively associated with a second threrapeutic agent.

Preferred first treatments include surgical resection and chemotherapeutic intervention.

In certain other embodiments, the antibodies and immunoconjugates of the invention may be combined with one or more diagnostic agents, typically diagnostic agents for use in connection with the diagnosis of cancer. A range of diagnostic compositions, kits and methods are thus included within the invention.

Yet further aspects are methods of diagnosis or imaging of a subject comprising the administration of an appropriate amount of an antibody or other protein of the invention as defined herein to the subject and detecting the presence and/or amount and/or the location of the antibody or other protein of the invention in the subject.

Appropriate diseases to be imaged or diagnosed in accordance with the above described uses and methods include any disease and preferably any cancer as described elsewhere herein.

In one embodiment, the invention provides a method of diagnosing disease, e.g. cancer in an animal comprising the step of:
(a) contacting a test sample taken from said animal with an antibody of the invention or an immunoconjugate thereof.

In a further embodiment, the invention provides a method of diagnosing disease, e.g. cancer in an animal comprising the steps of:
(a) contacting a test sample taken from said animal with an antibody of the invention or an immunoconjugate thereof;
(b) measuring or detecting the presence and/or amount and/or location of antibody-antigen complex in the test sample; and, optionally
(c) comparing the presence and/or amount of antibody-antigen complex in the test sample to a control.

In the above methods, said contacting step is carried out under conditions that permit the formation of an antibody-antigen complex. Appropriate conditions can readily be determined by a person skilled in the art.

In the above methods any appropriate test sample may be used, for example biopsy cells, tissues or organs suspected of being affected by disease or histological sections.

In certain of the above methods, the presence of any amount of antibody-antigen complex in the test sample would be indicative of the presence of disease. Preferably, for a positive diagnosis to be made, the amount of antibody-antigen complex in the test sample is greater or increased than, preferably significantly greater or increased than, the amount found in an appropriate control sample. More preferably, the significantly greater or increased levels are statistically significant, preferably with a probability value of <0.05. Appropriate methods of determining statistical significance are well known and documented in the art and any of these may be used.

Appropriate control samples could be readily chosen by a person skilled in the art, for example, in the case of diagnosis of a particular disease, an appropriate control would be a sample from a subject that did not have that disease. Appropriate control "values" could also be readily determined without running a control "sample" in every test, e.g., by reference to the range for normal subjects known in the art.

For use in the diagnostic or imaging applications, the antibodies of the invention may be labeled with a detectable marker such as a radio-opaque or radioisotope, such as $^3$H, $^{14}$C, $^{32}$P, $^{35}$S, $^{123}$I, $^{125}$I, $^{131}$I; a radioactive emitter (e.g., α, β or λ emitters); a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion; or a chemical moiety such as biotin which may be detected by binding to a specific cognate detectable moiety, e.g., labelled avidin/streptavidin. Methods of attaching a label to a binding protein, such as an antibody or antibody fragment, are known in the art. Such detectable markers allow the presence, amount or location of binding protein-antigen complexes in the test sample to be examined.

Preferred detectable markers for in vivo use include an X-ray detectable compound, such as bismuth (III), gold (III), lanthanum (III) or lead (II); a radioactive ion, such as copper$^{67}$, gallium$^{67}$, gallium$^{68}$, indium$^{111}$, indium$^{113}$, iodine$^{123}$, iodine$^{125}$, iodine$^{131}$, mercury$^{197}$, mercury$^{203}$, rhenium$^{186}$, rhenium$^{188}$, rubidium$^{97}$, rubidium$^{103}$, technetium$^{99m}$ or yttrium$^{90}$; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

The invention also includes diagnostic or imaging agents comprising the antibodies of the invention attached to a label that produces a detectable signal, directly or indirectly. Appropriate labels are described elsewhere herein.

Cancer treatment may also be carried out by:
(a) forming an image of a tumor by administering to an animal or patient having a tumor a diagnostic amount of at least a first detectably-labeled anti-EpCAM antibody of the invention, comprising a diagnostic agent operatively attached to the anti-EpCAM antibody of the invention, thereby forming a detectable image of the tumor; and
(b) subsequently administering to the same animal or patient a therapeutically optimized amount of at least a first naked anti-EpCAM antibody of the invention or therapeutic agent-antibody construct using such an antibody, thereby causing an anti-tumor effect.

The invention further includes kits comprising one or more of the antibodies, immunoconjugates or compositions of the invention or one or more of the nucleic acid molecules encoding the antibodies of the invention, or one or more recombinant expression vectors comprising the nucleic acid sequences of the invention, or one or more host cells or viruses comprising the recombinant expression vectors or nucleic acid sequences of the invention. Preferably said kits are for use in the methods and uses as described herein, e.g., the therapeutic, diagnostic or imaging methods as described herein, or are for use in the in vitro assays or methods as described herein. The antibody in such kits may preferably be an antibody conjugate as described elsewhere herein, e.g., may be conjugated to a detectable moiety or may be an immumoconjugate. Preferably said kits comprise instructions for use of the kit components, for example in diagnosis. Preferably said kits are for diagnosing or treating diseases as described elsewhere herein, e.g. cancer and optionally comprise instructions for use of the kit components to diagnose or treat such diseases.

The antibodies of the invention as defined herein may also be used as molecular tools for in vitro or in vivo applications and assays. As the antibodies have an antigen binding site, these can function as members of specific binding pairs and these molecules can be used in any assay where the particular binding pair member is required.

Thus, yet further aspects of the invention provide a reagent that comprises an antibody of the invention as defined herein and the use of such antibodies as molecular tools, for example in in vitro or in vivo assays.

TABLE 1

| SEQ ID NO: | Description | Sequence |
|---|---|---|
| 3-171 scFv | | |
| 1 | VH domain (nt) | CAGGTCCAGCTGGTGCAGTCTGGGGCTGAGGTGAA GAAGCCTGGGTCCTCGGTGAAGGTCTCCTGCAAGG CTTCTGGAGGCACCTTCAGCAGCTATGCTATCAGC TGGGTGCGACAGGCCCCTGGACAAGGGCTTGAGTG GATGGGAGGGATCATCCCTATCTTTGGTACAGCAA ACTACGCACAGAAGTTCCAGGGCAGAGTCACGATT ACCGCGGACGAATCCACGAGCACAGCCTACATGGA GCTGAGCAGCCTGAGATCTGAGGACACGGCCGTGT ATTACTGTGCGAGAGGCCTTCTATGGAACTACTGG GGCCAGGGAACCCTGGTCACCGTCTCCTCA See FIG. 1 |
| 2 | VL domain (nt) | GAAATTGTAATGACACAGTCTCCAGCCACCCTGTC TGTGTCTCCAGGGGAAAGAGCCACCCTCTCCTGCA GGGCCAGTCAGAGTGTTAGCAGCAACTTAGCCTGG TACCAGCAGAAACCTGGCCAGGCTCCCAGGCTCAT CATCTATGGTGCATCCACCACGGCCTCTGGTATCC CAGCCAGGTTCAGTGCCAGTGGGTCTGGGACAGAC TTCACTCTCACCATCAGCAGCCTGCAGTCTGAAGA TTTTGCAGTTTATTACTGTCAGCAGTATAATAACT GGGCCTCCGCGTACACTTTTGGCCAGGGGACCAAG CTGGAGATCAAA See FIG. 1 |
| 3 | VH domain (aa) | QVQLVQSGAEVKKPGSSVKVSCKASGGTFSSYAIS WVRQAPGQGLEWMGGIIPIFGTANYAQKFQGRVTI TADESTSTAYMELSSLRSEDTAVYYCARGLLWNYW GQGTLVTVSS See FIG. 1 |
| 4 | VL domain (aa) | EIVMTQSPATLSVSPGERATLSCRASQSVSSNLAW YQQKPGQAPRLIIYGASTTASGIPARFSASGSGTD FTLTISSLQSEDFAVYYCQQYNNWPPAYTFGQGTK LEIK See FIG. 1 |
| 5 | Heavy CDR1 | SYAIS |
| 6 | Heavy CDR2 | GIIPIFGTANYAQKFQG |
| 7 | Heavy CDR3 | GLLWNY |
| 8 | Light CDR1 | RASQSVSSNLA |
| 9 | Light CDR2 | GASTTAS |
| 10 | Light CDR3 | QQYNNWPPAYT |
| 11 | Heavy FR1 | QVQLVQSGAEVKKPGSSVKVSCKASGGTFS |
| 12 | Heavy FR2 | WVRQAPGQGLEWMG |
| 13 | Heavy FR3 | RVTITADESTSTAYMELSSLRSEDTAVYYCAR |
| 14 | Heavy FR4 | WGQGTLVTVSS |
| 15 | Light FR1 | EIVMTQSPATLSVSPGERATLSC |
| 16 | Light FR2 | WYQQKPGQAPRLIIY |
| 17 | Light FR3 | GIPARFSASGSGTDFTLTISSLQSEDFAVYYC |

TABLE 1-continued

| SEQ ID NO: | Description | Sequence |
|---|---|---|
| 18 | Light FR4 | FGQGTKLEIK |
| 19 | Linker | KLSGSASAPKLEEGEFSEARV |
| 20 | Whole scFv clone (nt) | CAGGTCCAGCTGGTGCAGTCTGGGGCTGAGGTGAA GAAGCCTGGGTCCTCGGTGAAGGTCTCCTGCAAGG CTTCTGGAGGCACCTTCAGCAGCTATGCTATCAGC TGGGTGCGACAGGCCCCTGGACAAGGGCTTGAGTG GATGGGAGGGATCATCCCTATCTTTGGTACAGCAA ACTACGCACAGAAGTTCCAGGGCAGAGTCACGATT ACCGCGGACGAATCCACGAGCACAGCCTACATGGA GCTGAGCAGCCTGAGATCTGAGGACACGGCCGTGT ATTACTGTGCGAGAGGCCTTCTATGGAACTACTGG GGCCAGGGAACCCTGGTCACCGTCTCCTCAAAGCT TTCAGGGAGTGCATCCGCCCAAACTTGAAGAAG GTGAATTTTCAGAAGCACGCGTAGAAATTGTAATG ACACAGTCTCCAGCCACCCTGTCTGTGTCTCCAGG GGAAAGAGCCACCCTCTCCTGCAGGGCCAGTCAGA GTGTTAGCAGCAACTTAGCCTGGTACCAGCAGAAA CCTGGCCAGGCTCCCAGGCTCATCATCTATGGTGC ATCCACCACGGCCTCTGGTATCCCAGCCAGGTTCA GTGCCAGTGGGTCTGGGACAGACTTCACTCTCACC ATCAGCAGCCTGCAGTCTGAAGATTTTGCAGTTTA TTACTGTCAGCAGTATAATAACTGGCCTCCGGCGT ACACTTTTGGCCAGGGGACCAAGCTGGAGATCAAA See FIG. 1 |
| 21 | Whole scFv clone (aa) | QVQLVQSGAEVKKPGSSVKVSCKASGGTFSSYAIS WVRQAPGQGLEWMGGIIPIFGTANYAQKFQGRVTI TADESTSTAYMELSSLRSEDTAVYYCARGLLWNYW GQGTLVTVSSKLSGSASAPKLEEGEFSEARVEIVM TQSPATLSVSPGERATLSCRASQSVSSNLAWYQQK PGQAPRLIIYGASTTASGIPARFSASGSGTDFTLT ISSLQSEDFAVYYCQQYNNWPPAYTFGQGTKLEIK See FIG. 1 |

3-171 Full length IgG

| 22 | IgG heavy chain (nt) | CAGGTCCAGCTGGTGCAGTCTGGGGCTGAGGTGAA GAAGCCTGGGTCCTCGGTGAAGGTCTCCTGCAAGG CTTCTGGAGGCACCTTCAGCAGCTATGCTATCAGC TGGGTGCGACAGGCCCCTGGACAAGGGCTTGAGTG GATGGGAGGGATCATCCCTATCTTTGGTACAGCAA ACTACGCACAGAAGTTCCAGGGCAGAGTCACGATT ACCGCGGACGAATCCACGAGCACAGCCTACATGGA GCTGAGCAGCCTGAGATCTGAGGACACGGCCGTGT ATTACTGTGCGAGAGGCCTTCTATGGAACTACTGG GGCCAGGGAACCCTGGTCACCGTCTCCTCAGCCTC CACCAAGGGCCCATCGGTCTTCCCCCTGGCACCCT CCTCCAAGAGCACCTCTGGGGGCACAGCGGCCCTG GGCTGCCTGGTCAAGGACTACTTCCCCGAACCGGT GACGGTGTCGTGGAACTCAGGCGCCCTGACCAGCG GCGTGCACACCTTCCCGGCTGTCCTACAGTCCTCA GGACTCTACTCCCTCAGCAGCGTGGTGACCGTGCC CTCCAGCAGCTTGGGCACCCAGACCTACATCTGCA ACGTGAATCACAAGCCCAGCAACACCAAGGTGGAC AAGAAAGTTGAGCCCAAATCTTGTGACAAAACTCA CACATGCCCACCGTGCCCAGCACCTGAACTCCTGG GGGGACCGTCAGTCTTCCTCTTCCCCCCAAAACCC AAGGACACCCTCATGATCTCCCGGACCCCTGAGGT CACATGCGTGGTGGTGGACGTGAGCCACGAAGACC CTGAGGTCAAGTTCAACTGGTACGTGGACGGCGTG GAGGTGCATAATGCCAAGACAAAGCCGCGGGAGGA GCAGTACAACAGCACGTACCGTGTGGTCAGCGTCC TCACCGTCCTGCACCAGGACTGGCTGAATGGCAAG GAGTACAAGTGCAAGGTCTCCAACAAAGCCCTCCC AGCCCCCATCGAGAAAACCATCTCCAAAGCCAAAG GGCAGCCCCGAGAACCACAGGTGTACACCCTGCCC CCATCCCGGGATGAGCTGACCAAGAACCAGGTCAG CCTGACCTGCCTGGTCAAAGGCTTCTATCCCAGC ACATCGCCGTGGAGTGGGAGAGCAATGGGCAGCCG GAGAACAACTACAAGACCACGCCTCCCGTGCTGGA CTCCGACGGCTCCTTCTTCCTCTACAGCAAGCTCA CCGTGGACAAGAGCAGGTGGCAGCAGGGGAACGTC TTCTCATGCTCCGTGATGCATGAGGCTCTGCACAA CCACTACACGCAGAAGAGCCTCTCCCTGTCTCCGG GTAAA |
| 23 | IgG light chain (nt) | GAAATTGTAATGACACAGTCTCCAGCCACCCTGTC TGTGTCTCCAGGGGAAAGAGCCACCCTCTCCTGCA GGGCCAGTCAGAGTGTTAGCAGCAACTTAGCCTGG TACCACAGAAACCTGGCCAGGCTCCCAGGCTCAT CATCTATGGTGCATCCACCACGGCCTCTGGTATCC CAGCCAGGTTCAGTGCCAGTGGGTCTGGGACAGAC TTCACTCTCACCATCAGCAGCCTGCAGTCTGAAGA TTTTGCAGTTTATTACTGTCAGCAGTATAATAACT GGCCTCCGGCGTACACTTTTGGCCAGGGGACCAAG CTGGAGATCAAACGAACTGTGGCTGCACCATCTGT CTTCATCTTCCCGCCATCTGATGAGCAGTTGAAAT CTGGAACTGCCTCTGTTGTGTGCCTGCTGAATAAC TTCTATCCCAGAGAGGCCAAAGTACAGTGGAAGGT GGATAACGCCCTCCAATCGGGTAACTCCCAGGAGA GTGTCACAGAGCAGGACAGCAAGGACAGCACCTAC AGCCTCAGCAGCACCCTGACGCTGAGCAAAGCAGA CTACGAGAAACACAAAGTCTACGCCTGCGAAGTCA CCCATCAGGGCCTGAGCTCGCCCGTCACAAAGAGC TTCAACAGGGGAGAGTGT |
| 24 | IgG heavy chain (aa) | QVQLVQSGAEVKKPGSSVKVSCKASGGTFSSYAIS WVRQAPGQGLEWMGGIIPIFGTANYAQKFQGRVTI TADESTSTAYMELSSLRSEDTAVYYCARGLLWNYW GQGTLVTVSSASTKGPSVFPLAPSSKSTSGGTAAL GCLVKDYFPEPVTVSWNSGALTSGVHTFPAVLQSS GLYSLSSVVTVPSSSLGTQTYICNVNHKPSNTKVD KKVEPKSCDKTHTCPPCPAPELLGGPSVFLFPPKP KDTLMISRTPEVTCVVVDVSHEDPEVKFNWYVDGV EVHNAKTKPREEQYNSTYRVVSVLTVLHQDWLNGK EYKCKVSNKALPAPIEKTISKAKGQPREPQVYTLP PSRDELTKNQVSLTCLVKGFYPSDIAVEWESNGQP ENNYKTTPPVLDSDGSFFLYSKLTVDKSRWQQGNV FSCSVMHEALHNHYTQKSLSLSPGK |
| 25 | IgG light chain (aa) | EIVMTQSPATLSVSPGERATLSCRASQSVSSNLAV VYQQKPGQAPRLIIYGASTTASGIPARFSASGSGT DFTLTISSLQSEDFAVYYCQQYNNWPPAYTFGQGT KLEIKRTVAAPSVFIFPPSDEQLKSGTASVVCLLN NFYPREAKVQWKVDNALQSGNSQESVTEQDSKDST YSLSSTLTLSKADYEKHKVYACEVTHQGLSSPVTK SFNRGEC |

TABLE 2

| SEQ ID NO: | Description | Sequence |
|---|---|---|

7-F17 scFv

| 26 | VL domain (nt) | GAAACGACACTCACGCAGTCTCCAGCCACCC TGTCTGTGTCTCCAGGGGAAAGAGCCACCCT CTCCTGCAGGGCCAGTCAGAGTGTTAGCAGC AACTTAGCCTGGTACCAGCAGAAACCTGGCC AGGCTCCCAGGCTCCTCATCTATGGTGCATC CACCAGGGCCACTGGTATCCCAGCCAGGTTC AGTGGCAGTGGGTCTGGGACAGAGTTCACTC TCACCATCAGCAGCCTGCAGTCTGAAGATTT TGCAGTTTATTACTGTCAGCAGTATAATAAC TGGCCTCCGGGGTTCACTTTCGGCCCTGGGA CCAAAGTGGATATCAAA |
| 27 | VL domain (aa) | ETTLTQSPATLSVSPGERATLSCRASQSVSS KNLAWYQQPGQAPRLLIYGASTRATGIPARF SGSGSGTEFTLTISSLQSEDFAVYYCQQYNN WPPGFTFGPGTKVDIK |

TABLE 2-continued

| SEQ ID NO: | Description | Sequence |
|---|---|---|
| 8 or 28 | Light CDR1 | RASQSVSSNLA |
| 29 | Light CDR2 | GASTRAT |
| 30 | Light CDR3 | QQYNNWPPGFT |
| 31 | Light FR1 | ETTLTQSPATLSVSPGERATLSC |
| 32 | Light FR2 | WYQQKPGQAPRLLIY |
| 33 | Light FR3 | GIPARFSGSGSGTEFTLTISSLQSEDFAVYYC |
| 34 | Light FR4 | FGPGTKVDIK |
| 35 | Whole scFv clone (nt) | CAGGTCCAGCTGGTGCAGTCTGGGGCTGAGGTGAAGAAGCCTGGGTCCTCGGTGAAGGTCTCCTGCAAGGCTTCTGGAGGCACCTTCAGCAGCTATGCTATCAGCTGGGTGCGACAGGCCCCTGGACAAGGGCTTGAGTGGATGGGAGGGATCATCCCTATCTTTGGTACAGCAAACTACGCACAGAAGTTCCAGGGCAGAGTCACGATTACCGCGGACGAATCCACGAGCACAGCCTACATGGAGCTGAGCAGCCTGAGATCTGAGGACACGGCCGTGTATTACTGTGCGAGAGGCCTTCTATGGAACTACTGGGGCCAGGGAACCCTGGTCACCGTCTCCTCAAAGCTTTCAGGGAGTGCATCCGCCCCAAAACTTGAAGAAGGTGAATTTTCAGAAGCACGCGTAGAAACGACACTCACGCAGTCTCCAGCCACCCTGTCTGTGTCTCCAGGGGAAAGAGCCACCCTCTCCTGCAGGGCCAGTCAGAGTGTTAGCAGCAACTTAGCCTGGTACCAGCAGAAACCTGGCCAGGCTCCCAGGCTCCTCATCTATGGTGCATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTACTGTCAGCAGTATAATAACTGGCCTCCGGGGTTCACTTTCGGCCCTGGGACCAAAGTGGATATCAAA |
| 36 | Whole scFv clone (aa) | QVQLVQSGAEVKKPGSSVKVSCKASGGTFSSYAISVVVRQAPGQGLEWMGGIIPIFGTANYAQKFQGRVTITADESTSTAYMELSSLRSEDTAVYYCARGLLWNYWGQGTLVTVSSKLSGSASAPKLEEGEFSEARVETTLTQSPATLSVSPGERATLSCRASQSVSSNLAVVYQQKPGQAPRLLIYGASTRATGIPARFSGSGSGTEFTLTISSLQSEDFAVYYCQQYNNWPPGFTFGPGTKVDIK |

The heavy chain sequences (nucleotide and amino acid) of antibody 7-F17 (VH domain, Heavy CDR1, Heavy CDR2, Heavy CDR3, Heavy FR1, Heavy FR2, Heavy FR3 and Heavy FR4) and the linker sequence are identical to the sequences set out in Table 1.

TABLE 3

| SEQ ID NO: | Description | Sequence |
|---|---|---|
| 12-C15 scFv | | |
| 39 | VL domain (nt) | GAAACGACACTCACGCAGTCTCCAGCCACCCTGTCTTTGTCTCCAGGGGAAAGAGCCACCCTCTCCTGCAGGGCCAGTCAGAGTGTTAGCAGCAACTTAGCCTGGTACCAGCAGAAACCTGGCCAGGCTCCCAGGCTCCTCATCTATGGTGCATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTACTGTCAGCACTATAATGACTGGCCTCCCACGTGGACGTTCGGCCAAGGGACCAAGCTGGAGATCAAA |
| 40 | VL domain (aa) | ETTLTQSPATLSLSPGERATLSCRASQSVSSNLAVVYQQKPGQAPRLLIYGASTRATGIPARFSGSGSGTEFTLTISSLQSEDFAVYYCQHYNDWPPTWTFGQGTKLEIK |
| 8, 28 or 41 | Light CDR1 | RASQSVSSNLA |
| 29 or 42 | Light CDR2 | GASTRAT |
| 43 | Light CD R3 | QHYNDWPPTWT |
| 44 | Light FR1 | ETTLTQSPATLSLSPGERATLSC |
| 32 or 45 | Light FR2 | WYQQKPGQAPRLLIY |
| 33 or 46 | Light FR3 | GIPARFSGSGSGTEFTLTISSLQSEDFAVYYC |
| 18 or 47 | Light FR4 | FGQGTKLEIK |
| 48 | Whole scFv clone (nt) | CAGGTCCAGCTGGTGCAGTCTGGGGCTGAGGTGAAGAAGCCTGGGTCCTCGGTGAAGGTCTCCTGCAAGGCTTCTGGAGGCACCTTCAGCAGCTATGCTATCAGCTGGGTGCGACAGGCCCCTGGACAAGGGCTTGAGTGGATGGGAGGGATCATCCCTATCTTTGGTACAGCAAACTACGCACAGAAGTTCCAGGGCAGAGTCACGATTACCGCGGACGAATCCACGAGCACAGCCTACATGGAGCTGAGCAGCCTGAGATCTGAGGACACGGCCGTGTATTACTGTGCGAGAGGCCTTCTATGGAACTACTGGGGCCAGGGAACCCTGGTCACCGTCTCCTCAAAGCTTTCAGGGAGTGCATCCGCCCCAAAACTTGAAGAAGGTGAATTTTCAGAAGCACGCGTAGAAACGACACTCACGCAGTCTCCAGCCACCCTGTCTTTGTCTCCAGGGGAAAGAGCCACCCTCTCCTGCAGGGCCAGTCAGAGTGTTAGCAGCAACTTAGCCTGGTACCAGCAGAAACCTGGCCAGGCTCCCAGGCTCCTCATCTATGGTGCATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTACTGTCAGCACTATAATGACTGGCCTCCCACGTGGACGTTCGGCCAAGGGACCAAGCTGGAGATCAAA |
| 49 | Whole scFv clone (aa) | QVQLVQSGAEVKKPGSSVKVSCKASGGTFSSYAISVVVRQAPGQGLEWMGGIIPIFGTANYAQKFQGRVTITADESTSTAYMELSSLRSEDTAVYYCARGLLWNYWGQGTLVTVSSKLSGSASAPKLEEGEFSEARVETTLTQSPATLSLSPGERATLSCRASQSVSSNLAVVYQQKPGQAPRLLIYGASTRATGIPARFSGSGSGTEFTLTISSLQSEDFAVYYCQHYNDWPPTWTFGQGTKLEIK |
| 12-C15 Full length IgG | | |
| 50 | IgG light chain (nt) | GAAACGACACTCACGCAGTCTCCAGCCACCCTGTCTTTGTCTCCAGGGGAAAGAGCCACCCTCTCCTGCAGGGCCAGTCAGAGTGTTAGCAGCAACTTAGCCTGGTACCAGCAGAAACCTGGCCAGGCTCCCAGGCTCCTCATCTATGGTGCATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTACTGTCAGCACTATAATGACTGGCCTCCCACGTGGACGTTCGGCCAAGGGACCAAGCTGGAGATCAAACGAACTGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAAC |

TABLE 3-continued

| SEQ ID NO: | Description | Sequence |
|---|---|---|
| | | TCCCAGGAGAGTGTCACAGAGCAGGACAGC AAGGACAGCACCTACAGCCTCAGCAGCACC CTGACGCTGAGCAAAGCAGACTACGAGAAA CACAAAGTCTACGCCTGCGAAGTCACCCAT CAGGGCCTGAGCTCGCCCGTCACAAAGAGC TTCAACAGGGGAGAGTGT |
| 51 | IgG light chain (aa) | ETTLTQSPATLSLSPGERATLSCRASQSVS SNLAWYQQKPGQAPRLLIYGASTRATGIPA RFSGSGSGTEFTLTISSLQSEDFAVYYCQH YNDWPPTWTFGQGTKLEIKRTVAAPSVFIF PPSDEQLKSGTASVVCLLNNFYPREAKVQW KVDNALQSGNSQESVTEQDSKDSTYSLSST LTLSKADYEKHKVYACEVTHQGLSSPVTKS FNRGEC |

The heavy chain sequences (nucleotide and amino acid) of antibody 12-C15 (VH domain, Heavy CDR1, Heavy CDR2, Heavy CDR3, Heavy FR1, Heavy FR2, Heavy FR3, Heavy FR4 and IgG heavy chain) and the linker sequence are identical to the sequences set out in Table 1.

TABLE 4

| SEQ ID NO: | Description | Sequence |
|---|---|---|
| 16-G5 scFv | | |
| 52 | VL domain (nt) | GATATTGTGATGACTCAGACTCCAGCCACC CTGTCTGTGTCTCCAGGGGAAAGAGCCACC CTCTCCTGCAGGGCCAGTCAGAGTGTTAGC AGCAACTTAGCCTGGTACCAGCAGAAACCT GGCCAGGCTCCCAGGCTCCTCATCTATGGT GCATCCACCAGGGCCACTGGTATCCCAGCC AGGTTCAGTGGCAGTGGGTCTGGGACAGAG TTCACTCTCACCATCAGCAGCCTGCAGTCT GAAGATTTTGCAGTTTATTACTGTCAGCAG TATAATAACTGGCCTCCGTCGTGGACGTTC GGCCAAGGGACCAAGGTGGAGATCAAA |
| 53 | VL domain (aa) | DIVMTQTPATLSVSPGERATLSCRASQSVS SNLAVVYQQKPGQAPRLLIYGASTRATGIP ARFSGSGSGTEFTLTISSLQSEDFAVYYCQ QYNNWPPSWTFGQGTKVEIK |
| 8, 28, 41 or 54 | Light CDR1 | RASQSVSSNLA |
| 29, 42 or 55 | Light CDR2 | GASTRAT |
| 56 | Light CDR3 | QQYNNWPPSWT |
| 57 | Light FR1 | DIVMTQTPATLSVSPGERATLSC |
| 32, 45 or 58 | Light FR2 | WYQQKPGQAPRLLIY |
| 33, 46 or 59 | Light FR3 | GIPARFSGSGSGTEFTLTISSLQSEDFA VYYC |
| 60 | Light FR4 | FGQGTKVEIK |
| 61 | Whole scFv clone (nt) | CAGGTCCAGCTGGTGCAGTCTGGGGCTGAG GTGAAGAAGCCTGGGTCCTCGGTGAAGGTC TCCTGCAAGGCTTCTGGAGGCACCTTCAGC AGCTATGCTATCAGCTGGGTGCGACAGGCC CCTGGACAAGGGCTTGAGTGGATGGGAGGG ATCATCCCTATCTTTGGTACAGCAAACTAC GCACAGAAGTTCCAGGGCAGAGTCACGATT ACCGCGGACGAATCCACGAGCACAGCCTAC ATGGAGCTGAGCAGCCTGAGATCTGAGGAC |

TABLE 4-continued

| SEQ ID NO: | Description | Sequence |
|---|---|---|
| | | ACGGCCGTGTATTACTGTGCGAGAGGCCTT CTATGGAACTACTGGGGCCAGGGAACCCTG GTCACCGTCTCCTCAAAGCTTTCAGGGAGT GCATCCGCCCCAAAACTTGAAGAAGGTGAA TTTTCAGAAGCACGCGTAGATATTGTGATG ACTCAGACTCCAGCCACCCTGTCTGTGTCT CCAGGGGAAAGAGCCACCCTCTCCTGCAGG GCCAGTCAGAGTGTTAGCAGCAACTTAGCC TGGTACCAGCAGAAACCTGGCCAGGCTCCC AGGCTCCTCATCTATGGTGCATCCACCAGG GCCACTGGTATCCCAGCCAGGTTCAGTGGC AGTGGGTCTGGGACAGAGTTCACTCTCACC ATCAGCAGCCTGCAGTCTGAAGATTTTGCA GTTTATTACTGTCAGCAGTATAATAACTGG CCTCCGTCGTGGACGTTCGGCCAAGGGACC AAGGTGGAGATCAAA |
| 62 | Whole scFv Clone (aa) | QVQLVQSGAEVKKPGSSVKVSCKASGGTFS SYAISVVRQAPGQGLEWMGGIIPIFGTAN YAQKFQGRVTITADESTSTAYMELSSLRSE DTAVYYCARGLLWNYWGQGTLVTVSSKLSG SASAPKLEEGEFSEARVDIVMTQTPATLSV SPGERATLSCRASQSVSSNLAVVYQQKPGQ APRLLIYGASTRATGIPARFSGSGSGTEFT LTISSLQSEDFAVYYCQQYNNWPPSWTFGQ GTKVEIK |
| 16-G5 Full length IgG | | |
| 63 | IgG light chain (nt) | GATATTGTGATGACTCAGACTCCAGCCACC CTGTCTGTGTCTCCAGGGGAAAGAGCCACC CTCTCCTGCAGGGCCAGTCAGAGTGTTAGC AGCAACTTAGCCTGGTACCAGCAGAAACCT GGCCAGGCTCCCAGGCTCCTCATCTATGGT GCATCCACCAGGGCCACTGGTATCCCAGCC AGGTTCAGTGGCAGTGGGTCTGGGACAGAG TTCACTCTCACCATCAGCAGCCTGCAGTCT GAAGATTTTGCAGTTTATTACTGTCAGCAG TATAATAACTGGCCTCCGTCGTGGACGTTC GGCCAAGGGACCAAGGTGGAAATCAAACGA ACTGTGGCTGCACCATCTGTCTTCATCTTC CCGCCATCTGATGAGCAGTTGAAATCTGGA ACTGCCTCTGTTGTGTGCCTGCTGAATAAC TTCTATCCCAGAGAGGCCAAAGTACAGTGG AAGGTGGATAACGCCCTCCAATGGGTAAC TCCCAGGAGAGTGTCACAGAGCAGGACAGC AAGGACAGCACCTACAGCCTCAGCAGCACC CTGACGCTGAGCAAAGCAGACTACGAGAAA CACAAAGTCTACGCCTGCGAAGTCACCCAT CAGGGCCTGAGCTCGCCCGTCACAAAGAGC TTCAACAGGGGAGAGTGT |
| 64 | IgG light chain (aa) | DIVMTQTPATLSVSPGERATLSCRASQSVS SNLAWYQQKPGQAPRLLIYGASTRATGIPA RFSGSGSGTEFTLTISSLQSEDFAVYYCQQ YNNWPPSWTFGQGTKVEIKRTVAAPSVFIF PPSDEQLKSGTASVVCLLNNFYPREAKVQW KVDNALQSGNSQESVTEQDSKDSTYSLSST LTLSKADYEKHKVYACEVTHQGLSSPVTKS FNRGEC |

The heavy chain sequences (nucleotide and amino acid) of antibody 16-G5 (VH domain, Heavy CDR1, Heavy CDR2, Heavy CDR3, Heavy FR1, Heavy FR2, Heavy FR3, Heavy FR4 and IgG heavy chain) and the linker sequence are identical to the sequences set out in Table 1.

TABLE 5

| SEQ ID NO: | Description | Sequence |
|---|---|---|
| 17-C20 scFv | | |
| 65 | VL domain (nt) | GAAACGACACTCACGCAGTCTCCAGCCACC CTGTCTGTGTCTCCAGGGGAAAGAGCCACC CTCTCCTGCAGGGCCAGTCAGAGTGTTAGC AGCAACTTAGCCTGGTACCAGCAGAAACCT GGCCAGGCTCCCAGGCTCCTCATCTATGGT GCATCCACCAGGGCCACTGGTATCCCAGCC AGGTTCAGTGGCAGTGGGTCTGGGACAGAG TTCACTCTCACCATCAGCAGCCTGCAGTCT GAAGATTTTGCAGTTTATTACTGTCAGCAG TATAATAACTGGCCTCCGATGTACACTTTT GGCCAGGGGACCAAGGTGGAGATCAAA |
| 66 | VL domain (aa) | ETTLTQSPATLSVSPGERATLSCRASQSVS SNLAWYQQKPGQAPRLLIYGASTRATGIP ARFSGSGSGTEFTLTISSLQSEDFAVYYCQ QYNNWPPMYTFGQGTKVEIK |
| 8, 28, 41, 54 or 67 | Light CDR1 | RASQSVSSNLA |
| 29, 42, 55 or 68 | Light CDR2 | GASTRAT |
| 69 | Light CDR3 | QQYNNWPPMYT |
| 31 or 70 | Light FR1 | ETTLTQSPATLSVSPGERATLSC |
| 32, 45, 58 or 71 | Light FR2 | WYQQKPGQAPRLLIY |
| 33, 46, 59 or 72 | Light FR3 | GIPARFSGSGSGTEFTLTISSLQSEDFAVY YC |
| 60 or 73 | Light FR4 | FGQGTKVEIK |
| 74 | Whole scFv clone (nt) | CAGGTCCAGCTGGTGCAGTCTGGGGCTGAGG TGAAGAAGCCTGGGTCCTCGGTGAAGGTCTC CTGCAAGGCTTCTGGAGGCACCTTCAGCAGC TATGCTATCAGCTGGGTGCGACAGGCCCCTG GACAAGGGCTTGAGTGGATGGGAGGGATCAT CCCTATCTTTGGTACAGCAAACTACGCACAG AAGTTCCAGGGCAGAGTCACGATTACCGCGG ACGAATCCACGAGCACAGCCTACATGGAGCT GAGCAGCCTGAGATCTGAGGACACGGCCGTG TATTACTGTGCGAGAGGCCTTCTATGGAACT ACTGGGGCCAGGGAACCCTGGTCACCGTCTC CTCAAAGCTTTCAGGGAGTGCATCCGCCCCA AAACTTGAAGAAGGTGAATTTTCAGAAGCAC GCGTAGAAACGACACTCACGCAGTCTCCAGC CACCCTGTCTGTGTCTCCAGGGGAAAGAGCC ACCCTCTCCTGCAGGGCCAGTCAGAGTGTTA GCAGCAACTTAGCCTGGTACCAGCAGAAACC TGGCCAGGCTCCCAGGCTCCTCATCTATGGT GCATCCACCAGGGCCACTGGTATCCCAGCCA GGTTCAGTGGCAGTGGGTCTGGGACAGAGTT CACTCTCACCATCAGCAGCCTGCAGTCTGAA GATTTTGCAGTTTATTACTGTCAGCAGTATA ATAACTGGCCTCCGATGTACACTTTTGGCCA GGGGACCAAGGTGGAGATCAAA |
| 75 | Whole scFv clone (aa) | QVQLVQSGAEVKKPGSSVKVSCKASGGTFSS YAISWVRQAPGQGLEWMGGIIPIFGTANYA QKFQGRVTITADESTSTAYMELSSLRSEDTA VYYCARGLLWNYWGQGTLVTVSSKLSGSASA PKLEEGEFSEARVETTLTQSPATLSVSPGER ATLSCRASQSVSSNLAVYQQKPGQAPRLLI YGASTRATGIPARFSGSGSGTEFTLTISSLQ SEDFAVYYCQQYNNWPPMYTFGQGTKVEIK |

TABLE 5 -continued

| SEQ ID NO: | Description | Sequence |
|---|---|---|
| 17-C20 Full length IgG | | |
| 76 | IgG light chain (nt) | GAAACGACACTCACGCAGTCTCCAGCCACC TGTCTGTGTCTCCAGGGGAAAGAGCCACCCT CTCCTGCAGGGCCAGTCAGAGTGTTAGCAGC AACTTAGCCTGGTACCAGCAGAAACCTGGCC AGGCTCCCAGGCTCCTCATCTATGGTGCATC CACCAGGGCCACTGGTATCCCAGCCAGGTTC AGTGGCAGTGGGTCTGGGACAGAGTTCACTC TCACCATCAGCAGCCTGCAGTCTGAAGATTT TGCAGTTTATTACTGTCAGCAGTATAATAAC TGGCCTCCGATGTACACTTTTGGCCAGGGGA CCAAGGTGGAAATCAAACGAACTGTGGCTGC ACCATCTGTCTTCATCTTCCCGCCATCTGAT GAGCAGTTGAAATCTGGAACTGCCTCTGTTG TGTGCCTGCTGAATAACTTCTATCCCAGAGA GGCCAAAGTACAGTGGAAGGTGGATAACGCC CTCCAATCGGGTAACTCCCAGGAGAGTGTCA CAGAGCAGGACAGCAAGGACAGCACCTACAG CCTCAGCAGCACCCTGACGCTGAGCAAAGCA GACTACGAGAAACACAAAGTCTACGCCTGCG AAGTCACCCATCAGGGCCTGAGCTCGCCCGT CACAAAGAGCTTCAACAGGGGAGAGTGT |
| 77 | IgG light chain (aa) | ETTLTQSPATLSVSPGERATLSCRASQSVSS NLAWYQQKPGQAPRLLIYGASTRATGIPARF SGSGSGTEFTLTISSLQSEDFAVYYCQQYNN WPPMYTFGQGTKVEIKRTVAAPSVFIFPPSD EQLKSGTASVVCLLNNFYPREAKVQWKVDNA LQSGNSQESVTEQDSKDSTYSLSSTLTLSKA DYEKHKVYACEVTHQGLSSPVTKSFNRGEC |

The heavy chain sequences (nucleotide and amino acid) of antibody 17-C20 (VH domain, Heavy CDR1, Heavy CDR2, Heavy CDR3, Heavy FR1, Heavy FR2, Heavy FR3, Heavy FR4 and IgG heavy chain) and the linker sequence are identical to the sequences set out in Table 1.

TABLE 6

| SEQ ID NO: | Description | Sequence |
|---|---|---|
| 24-G6 scFv | | |
| 78 | VL domain (nt) | GAAACGACACTCACGCAGTCTCCAGCCACC CTGTCTGTGTCTCCAGGGGAAAGAGCCACC CTCTCCTGCAGGGCCAGTCAGAGTGTTAGC AGCAACTTAGCCTGGTACCAGCAGAAACCT GGCCAGGCTCCCAGGCTCCTCATCTATGGT GCATCCACCAGGGCCACTGGTATCCCAGCC AGGTTCAGTGGCAGTGGGTCTGGGACAGAG TTCACTCTCACCATCAGCAGCCTGCAGTCT GAAGATTTTGCAGTTTATTACTGTCAGAAG TATAATAACTGGCCTCCGGCCTTCACTTTC GGCCCTGGGACCAAAGTGGATATCAAA |
| 79 | VL domain (aa) | ETTLTQSPATLSVSPGERATLSCRASQSVS SNLAVVYQQKPGQAPRLLIYGASTRATGIP ARFSGSGSGTEFTLTISSLQSEDFAVYYCQ KYNNWPPAFTFGPGTKVDIK |
| 8, 28, 41, 54, 67 or 80 | Light CDR1 | RASQSVSSNLA |
| 29, 42, 55, 68 or 81 | Light CDR2 | GASTRAT |

TABLE 6-continued

| SEQ ID NO: | Description | Sequence |
|---|---|---|
| 82 | Light CDR3 | QKYNNWPPAFT |
| 31, 70 or 83 | Light FR1 | ETTLTQSPATLSVSPGERATLSC |
| 32, 45, 58, 71 or 84 | Light FR2 | WYQQKPGQAPRLLIY |
| 33, 46, 59, 72 or 85 | Light FR3 | GIPARFSGSGSGTEFTLTISSLQSEDFAVYYC |
| 34 or 86 | Light FR4 | FGPGTKVDIK |
| 87 | Whole scFv clone (nt) | CAGGTCCAGCTGGTGCAGTCTGGGGCTGAGG TGAAGAAGCCTGGGTCCTCGGTGAAGGTCTC CTGCAAGGCTTCTGGAGGCACCTTCAGCAGC TATGCTATCAGCTGGGTGCGACAGGCCCCTG GACAAGGGCTTGAGTGGATGGGAGGGATCAT CCCTATCTTTGGTACAGCAAACTACGCACAG AAGTTCCAGGGCAGAGTCACGATTACCGCGG ACGAATCCACGAGCACAGCCTACATGGAGCT GAGCAGCCTGAGATCTGAGGACACGGCCGTG TATTACTGTGCGAGAGGCCTTCTATGGAACT ACTGGGGCCAGGGAACCCTGGTCACCGTCTC CTCAAAGCTTTCAGGGAGTGCATCCGCCCA AAACTTGAAGAAGGTGAATTTTCAGAAGCAC GCGTAGAAACGACACTCACGCAGTCTCCAGC CACCCTGTCTGTGTCTCCAGGGGAAAGAGCC ACCCTCTCCTGCAGGGCCAGTCAGAGTGTTA GCAGCAACTTAGCCTGGTACCAGCAGAAACC TGGCCAGGCTCCCAGGCTCCTCATCTATGGT GCATCCACCAGGGCCACTGGTATCCCAGCCA GGTTCAGTGGCAGTGGGTCTGGGACAGAGTT CACTCTCACCATCAGCAGCCTGCAGTCTGAA GATTTTGCAGTTTATTACTGTCAGAAGTATA ATAACTGGCCTCCGGCCTTCACTTTCGGCCC TGGGACCAAAGTGGATATCAAA |
| 88 | Whole scFv clone (aa) | QVQLVQSGAEVKKPGSSVKVSCKASGGTFSS YAISVVVRQAPGQGLEWMGGIIPIFGTANYA QKFQGRVTITADESTSTAYMELSSLRSEDTA VYYCARGLLWNYWGQGTLVTVSSKLSGSASA PKLEEGEFSEARVETTLTQSPATLSVSPGER ATLSCRASQSVSSNLAVVYQQKPGQAPRLLI YGASTRATGIPARFSGSGSGTEFTLTISSLQ SEDFAVYYCQKYNNWPPAFTFGPGTKVDIK |

The heavy chain sequences (nucleotide and amino acid) of antibody 24-G6 (VH domain, Heavy CDR1, Heavy CDR2, Heavy CDR3, Heavy FR1, Heavy FR2, Heavy FR3 and Heavy FR4) and the linker sequence are identical to the sequences set out in Table 1.

TABLE 7

| SEQ ID NO: | DESCRIPTION | SEQUENCE |
|---|---|---|
| 37 | VL CDR2 | G A S T $X_5$ A $X_7$ |
| 38 | VL CDR2 | G A S T R/T A T/S |
| 89 | VL CDR3 | Q $X_2$ Y N $X_5$ W P P $X_9$ $X_{10}$ T |
| 90 | VL CDR3 | Q Q/H/K Y N N/D W P P G/T/S/M/A F/W/Y T |

The invention will now be described in more detail in the following non-limited examples with reference to the Figures in which:

FIG. 1 shows the nucleotide and amino acid sequences of the heavy (VH) and light (VL) chain variable region of an scFv form of clone 3-17I. The ScFv genes were cloned via Nco/NotI site into pHOG21 plasmid vector (3.7 Kb). The restriction sites used for initial gene cloning (NcoI, HindIII, MluI and NotI) are underlined. The linker sequence between VH and VL is shown in italics.

FIG. 2 shows flow cytometric analysis of 3-17I IgG, MOC31 IgG and MT201 IgG binding to the naturally EpCAM+Kato III cell line. Anti-green fluorescent protein (GFP) antibody is used as a negative control. MFI=Median Fluorescence Intensity.

FIGS. 3A, 3B and 3C show Western blot binding analysis of 3-17I IgG (FIG. 3A), MT201 IgG (FIG. 3B) and MOC31 IgG (FIG. 3C) binding to human (Hu) and Cynomolgus (Cy) EpCAM-Fc variants under non-reducing and reducing conditions. M=Molecular weight markers.

FIGS. 4A, 4B and 4C show ELISA binding analysis of 3-17I IgG (FIG. 4A), MT201 IgG (FIG. 4B) and MOC31 IgG (FIG. 4C) to human and cynomolgus EpCAM-Fc variants. MAXI-Sorb plates were coated with human and cynomolgus EpCAM-Fc at a concentration of 1 µg/ml. The antibody was added in 2-fold dilutions from 133 nM to 32 fM.

Figures 8A, 8B:
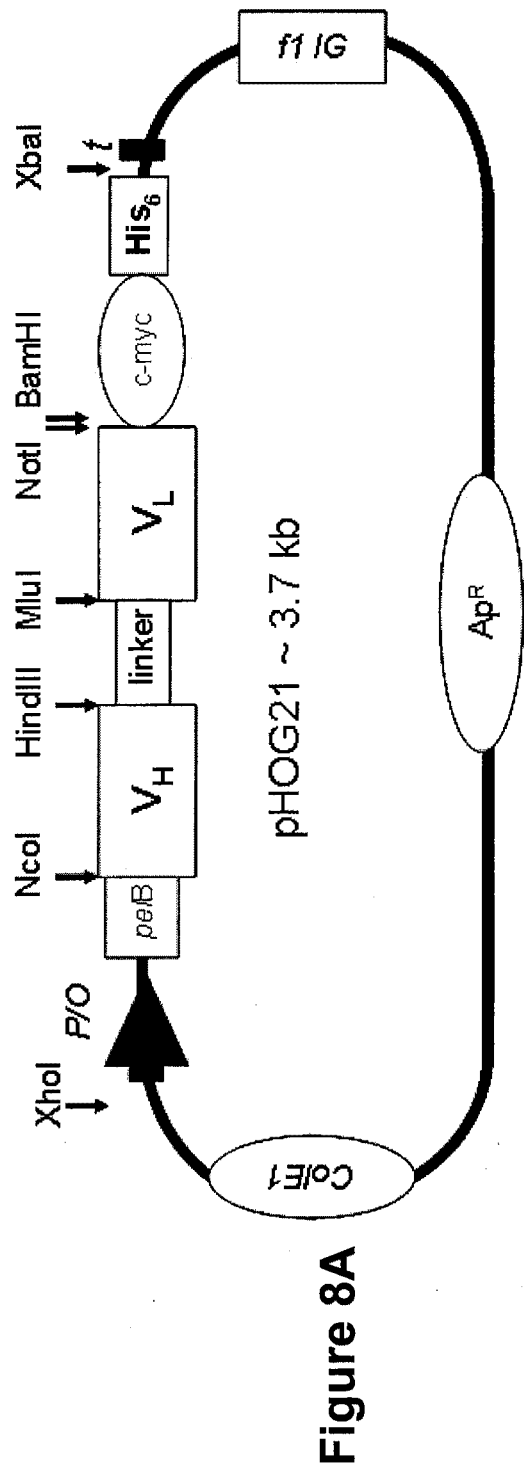

FIGS. 8A and 8B show the scFv expression vector. FIG. 8A shows the scFv expression vector pHOG21. ApR, Ampicillin resistance gene; ColE1, origin of DNA replication; fIIG, intergenic region of phage f1; c-myc, sequence encoding the epitope recognized by the monoclonal antibody 9E10; $His_6$, sequence encoding six histidine residues; pelB, sequence encoding signal peptide of bacterial pectate lyase; P/O, wild type Iac promoter operator. FIG. 8B shows the nucleotide and amino acid sequences of the C-terminal coding region.

Figure 9:
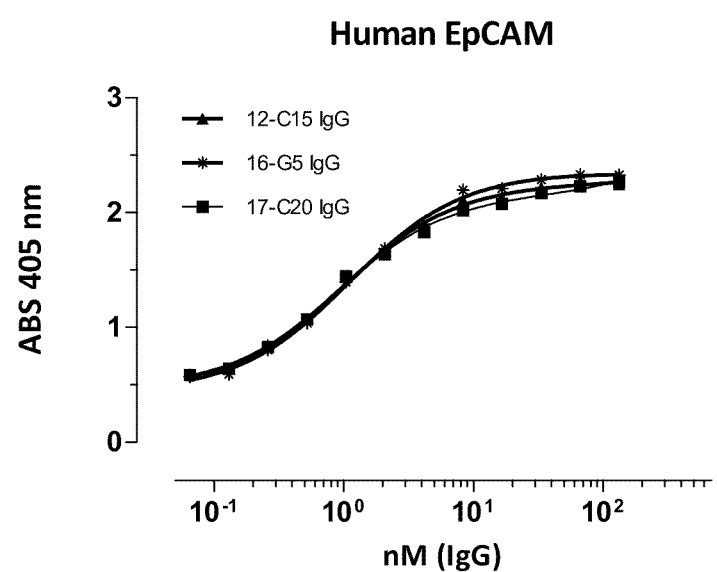

FIG. 9 shows ELISA binding analysis of 12-C15 IgG, 16-G5 IgG and 17-C20 IgG to human EpCAM-Fc. MAXI-Sorb plates were coated with human EpCAM-Fc at a concentration of 1 µg/ml. The antibody was added in 2-fold dilutions from 133 nM to 65 µM.

Figure 10A:
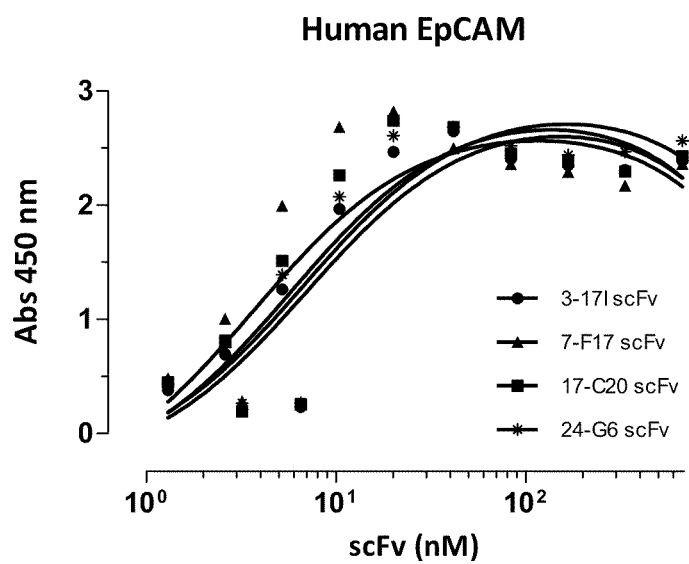
Figure 10B:
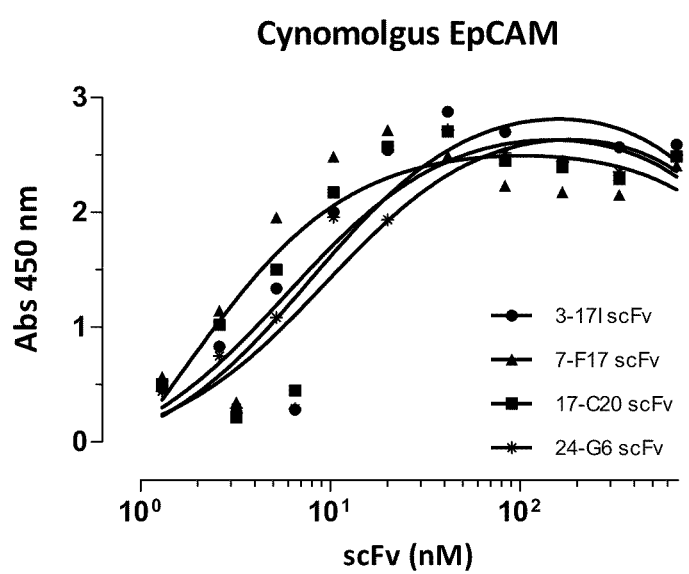

FIGS. 10A and 10B show ELISA binding analysis of 3-17I scFv, 7-F17 scFv, 17-C20 scFv and 24-G6 scFv to human EpCAM-Fc (FIG. 10A) and to cynomolgus EpCAM-Fc (FIG. 10B). MAXI-Sorb plates were coated with human or cynomolgus EpCAM-Fc at a concentration of 5 µg/ml. The antibody was added in 2-fold dilutions from 667 nM to 3.2 nM.

EXAMPLE 1

Novel Antibody

Given the need for further tumor specific antibodies which can be used as cancer therapeutics, a human antibody has been identified which specifically recognizes colon cancer cell lines such as HT29. The antibody can specifically bind to EpCAM. A single chain form of the antibody was cloned in the pHOG21 plasmid (FIG. 8) which contains a c-myc and 6×His tag epitopes. TG1 bacteria were transformed and the scFv was expressed upon IPTG induction. The binding of the purified scFv was confirmed by flow cytometry using an Easycyte flow cytometer.

Sequencing

The nucleotide sequences of the heavy and light chain of the antibody producing clone were sequenced. The antibody is designated as 3-17I (scFv). The nucleotide sequence and amino acid sequence of the light and heavy chain of 3-17I (scFv) are shown in FIG. 1 and Table 1. The CDR regions of the light and heavy chains of 3-171 are shown in Table 1.

The IgG form of this antibody has also been made. The IgG form is of the IgG1 isotype and it comprises two heavy chains and two light chains. Each heavy chain comprises a VH domain of SEQ ID NO: 3 and an IgG1 constant region. Each light chain comprises a VL domain of SEQ ID NO: 4 and a kappa light constant region. The components of the IgG form of the antibody were cloned into vectors based on a vector published by Lars Norderhaug et al, JIM 204 (1997) 77-87 and using the method described in this citation. The vector contains a standard CMV promoter. An IgG leader sequence (mgwsciilflvatatgvhs) was introduced into each vector. The VH and VL domains were cloned into separate vectors containing genomic copies (introns+exons) of the human IgG1 and Kappa genes, respectively into BsmI and BSiWI sites which had been introduced by PCR. The IgG1 vector contains a hygromycin resistance gene, whereas the Kappa vector contains a neomycin resistance gene. HEK293/T cells were transiently transfected and after 5-6 days, the IgG was purified via Protein-A followed by size exclusion to isolate the monomeric IgG fraction.

The amino acid sequences of the complete heavy and light chains of the 3-17I IgG antibody are shown below.

```
3-17I IgG Heavy chain (amino acid sequence)
                                  (SEQ ID NO: 24)
QVQLVQSGAEVKKPGSSVKVSCICASGGTFSSYAISWVRQAPGQGLEW

MGGIIPIFGTANYAQKFQGRVTITADESTSTAYMELSSLRSEDTAVYY

CARGLLWNYWGQGTLVTVSSASTKGPSVFPLAPSSKSTSGGTAAL

GCLVKDYFPEPVTVSWNSGALTSGVHTFPAVLQSSGLYSL

SSVVTVPSSSLGTQTYICNVNHKPSNTKVDKKVEPKSCDKT

HTCPPCPAPELLGGPSVFLFPPKPKDTLMISRTPEVTCVV

VDVSHEDPEVKFNWYVDGVEVHNAKTKPREEQYNSTYRVV

SVLTVLHQDWLNGKEYKCKVSNKALPAPIEKTISKAKGQPREPQV

YTLPPSRDELTKNQVSLTCLVKGFYPSDIAVEWESNGQPE

NNYKTTPPVLDSDGSFFLYSKLTVDKSRWQQGNVFSCSVM

HEALHNHYTQKSLSLSPGK
```

Constant regions are in bold italics

```
3-17I IgG Light chain (amino acid sequence)
                                  (SEQ ID NO: 25)
EIVMTQSPATLSVSPGERATLSCRASQSVSSNLAWYQQKPGQAPRLIT

YGASTTASGIPARFSASGSGTDFTLTISSLQSEDFAVYYCQQYNNWPP

AYTFGQGTKLEIKRTVAAPSVFIFPPSDEQLKSGTASVVCL

LNNFYPREAKVQWKVDNALQSGNSQESVTEQDSKDSTYSL

SSTLTLSKADYEKHKVYACEVTHQGLSSPVTKSFNRGEC
```

Constant regions are in bold italics.

Twelve related antibodies which bind to EpCAM and which have an identical heavy chain sequence to 3-17I but a different light chain sequence were also identified. The sequences of five of these related antibodies (7-F17, 12-C15, 16-G5,17-C20 and 24-G6) are set out in Tables 2-6.

EXAMPLE 2

Binding of 3-17I IgG to Kato III Cells

Flow cytometric analysis was performed to analyze binding of the 3-17I IgG to EpCAM-positive cells. As positive controls, anti-EpCAM chimeric (mouse variable/human constant domains) and fully human antibodies, MOC31 and MT201, respectively, were used.

The amino acid sequences of the complete heavy and light chains of the MT201 IgG and MOC31 IgG antibodies used are shown below. The constant regions are in bold italics.

```
MT201 IgG Heavy Chain (amino acid sequence)
EVQLLESGGGVVQPGRSLRLSCAASGFTFSSYGMHWVRQAPGKGLEWVA

VISYDGSNKYYADSVKGRFTISRDNSKNTLYLQMNSLRAEDTAVYYCAK

DMGWGSGWRPYYYYGMDVWGQGTTVTVSSASTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKKVEPKS

CDKTHTCPPCPAPELLGGPSVFLFPPKPKDTLMISRTPEVTCVV

VDVSHEDPEVKFNWYVDGVEVHNAKTKPREEQYNSTYRVVSVLTV

LHQDWLNGKEYKCKVSNKALPAPEKTISKAKGQPREPQVYTLPP

SRDELTKNQVSLTCLVKGFYPSDIAVEWESNGQPENNYKT

TPPVLDSDGSFFLYSKLTVDKSRWQQGNVFSCSVMHEALHNHYTQ

KSLSLSPGK

MT201 IgG Light Chain (amino acid sequence)
ELQMTQSPSSLSASVGDRVTITCRTSQSISSYLNWYQQKPGQPPKLLIYW

ASTRESGVPDRFSGSGSGTDFTLTISSLQPEDSATYYCQQSYDIPYTFGQ

GTKLEIKRTVAAPSVFIFPPSDEQIKSGTASVVCLLNNFYP

REAKVQWKVDNALQSENSQESVTEQDSKDSTYSLSSTLTL

SKADYEKHKVYACEVTHQGLSSPVTKSFNRGEC
```

These sequences were deduced from the amino acid sequences for MT201, which is also referred to as HD69, as given in WO98/46645 and Raum et al., Cancer Immunol Immunother (2001) 50: 141-150.

```
MOC31 IgG Heavy Chain (amino acid sequence)
QVKLQQSGPELKKPGETVKISCKASGYTFTNYGMNWVKQAPGKGLKWMG

WINTYTGESTYADDFKGRFAFSLETSASAAYLQINNLKNEDTATYFCAR

FAIKGDYWGQGTTVTVSSASTKGPSVFPLAPSSKSTSGGTAALGCLVK

DYFPEPVTVSWNSGAITSGVHTFPAVLQSSGLYSLSS
```

-continued

VVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNW

YVDGVEVHNAKTKPREEQYNSTYRVVSVLTVLHQDWLNGKEYKC

KVSNKALPAPIEKTISKAKGQPREPQVYTLPPSRDELTKNQVSLT

CLVKGFYPSDIAVEWESNGQPENNYKTTPPVLDYSKLTVDKFSCS

VMHEALHNHYTQKSLSLSPGK

```
MOC31 IgG Light Chain (amino acid sequence)
DIVLTQSPFSNPVTLGTSASISCRSTKSLLHSNGITYLYWYLQKPGQSP
```

QLLIYQMSNLASGVPDRFSSSGSGTDFTLRISRVEAEDVGVYYCAQNLE

IPRTFGGGTKLEIKRTVAAPSVFIFPPSDEQLKSGTASVVCLLN

NFYPREAKVQWKVDNALQSGNSQESVTEQDSKDSTYSLSSTLTL

SKADYEKHIKVYACEVTHQGLSSPVTKSFNRGEC

These sequences were deduced from the MOC31 amino acid sequence as given in Beiboer et al., Journal of Molecular Biology, volume 296, Issue 3, 25 Feb. 2000, Pages 833-849.

Figure 2:
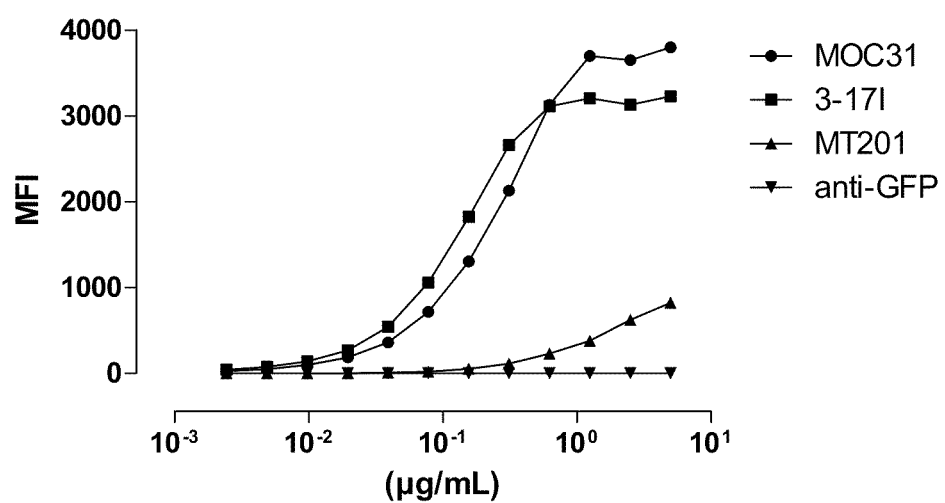

The anti-green fluorescent protein (GFP) antibody was used as a negative control. For flow cytometry, Kato III cells (ATCC number (gastric carcinoma, ATCC number HTB-103)) were grown under standard conditions, harvested from the culture flasks, washed 2 times with PBS, re-suspended in PBS with 0.2% BSA and 0.09% NaN$_3$ and finally distributed at 1×10$^5$ cells per well into V-shaped 96-well plates (Greiner Bio-One, Frickenhausen, Germany). Cells were centrifuged at 400×g for 5 min and then incubated at 4° C. for 45 min with 50 μL of each different antibody dilution (all dilutions made in PBS with 0.2% BSA and 0.09% NaN$_3$). After washing in PBS with 0.2% BSA and 0.09% NaN$_3$, the cells were stained with 10 μg/mL of RPE-conjugated goat anti-human IgG (AbDSerotec, Düsseldorf, Germany) for 30 min at 4° C. The stained cells were washed, re-suspended in 200 μL PBS with 0.2% BSA and 0.09% NaN$_3$ and transferred to a U-shaped 96-well plate (Corning, Schiphol-Rijk, The Netherlands) for analysis on EasyCyte flow cytometer (Guava Technologies, Hayward, Calif., USA). The results shown in FIG. 2 clearly demonstrate that the antibody 3-17I specifically interacts with the naturally EpCAM$^+$Kato III cell line with an affinity comparable to that of MOC31. In contrast, the antibody MT201 demonstrated significantly weaker binding to the EpCAM-positive Kato III cells.

EXAMPLE 3

Binding characteristics of 3-17I IgG

To determine the ability of 3-17I to bind to EpCAM, Western blot analysis, ELISA and BIAcore assays were performed.

Western Blot Analysis

To analyze the binding specificity and cross-reactivity of antibodies 3-17I, MT201 and MOC31 to human and cynomolgus EpCAM, sodium dodecyl sulfate polyacrylamide gel electrophoresis (SDS-PAGE) and Western blot analysis were performed under reducing and non-reducing conditions. All the antibodies were in IgG format and were produced in transiently transfected HEK-293 cells. The antibodies were then purified on Protein A Sepharose (GE Healthcare, Uppsala, Sweden) followed by fractionation on two serial coupled size exclusion columns, Superdex 200 and Superdex 75. The resultant IgG preparations appeared to be monomeric with >95% purity. The recombinant human and cynomolgus EpCAM antigens were also produced in HEK-293 cells and purified in one step on a Protein A Sepharose column. The determined purity of the antigen preparation was above 90%. Both EpCAM constructs consist of the extracellular domains of EpCAM fused to a human Fc region from IgG1.

The human EpCAM sequence was derived from NCBI database NP-002345 and the Cynomolgus from CS611076. The amino acid sequences of the human EpCAM/Fc fusion and the Cynomolgus EpCAM/Fc fusion are shown below:

```
Amino acid sequence-Human EpCAM/Fc fusion
MAPPQVLAFGLLLAAATATFAAAQEECVCENYKLAVNCFVNNNRQCQCTSVGAQNTVICSKLAA
-------Signal peptide---|-------- Start Human EPCAM sequence
KCLVMKAEMNGSKLGRRAKPEGALQNNDGLYDPDCDESGLFKAKQCNGTSTCWCVNTAGVRRTD
KDTEITCSERVRTYWIIIELKHKAREKPYDSKSLRTALQKEITTRYQLDPKFITSILYENNVIT
IDLVQNSSQKTQNDVDIADVAYYFEKDVKGESLFHSKKMDLTVNGEQLDLDPGQTLIYYVDEKA
                                                Human EPCAM sequence---
PEFSMQGLKAAADKTHTCPPCPAPELLGGPSVFLFPPKPKDTLMISRTPEVTCVVVDVSHEDPE
----End--|--|-------- Start Human IgG1 Fc sequence
VKFNWYVDGVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK
           End Human IgG1 Fc sequence---|
Amino acid sequence-Cynomolgus EpCAM/Fc fusion
MAPPQVLAFGLLLAAATATFAAAQKECVCENYKLAVNCFLNDNGQCQCTSIGAQNTVLCSKLAA
-----Signal peptide----|--------- Start Cy EPCAM sequence
KCLVMKAEMNGSKLGRRAKPEGALQNNDGLYDPDCDESGLFKAKQCNGTSTCWCVNTAGVRRTD
KDTEITCSERVRTYWIIIELKHKAREKPYDVQSLRTALEEAIKTRYQLDPKFITNILYEDNVIT
IDLVQNSSQKTQNDVDIADVAYYFEKDVKGESLFHSKKMDLRVNGEQLDLDPGQTLIYYVDEKA
PEFSMQGLKAAADKTHTCPPCPAPELLGGPSVFLFPPKPKDTLMISRTPEVTCVVVDVSHEDP
----End---|--|--------- Start Human IgG1 Fc sequence
EVKFNWYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK
           End Human IgG1 Fc sequence---|
```

Figure 3A:
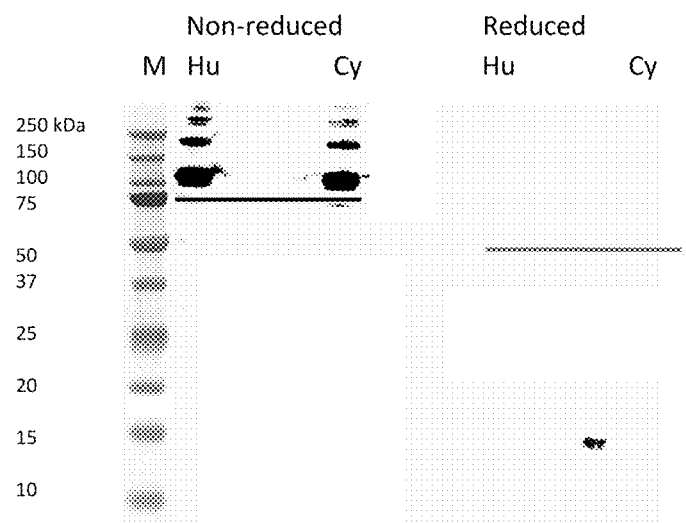
Figure 3B:
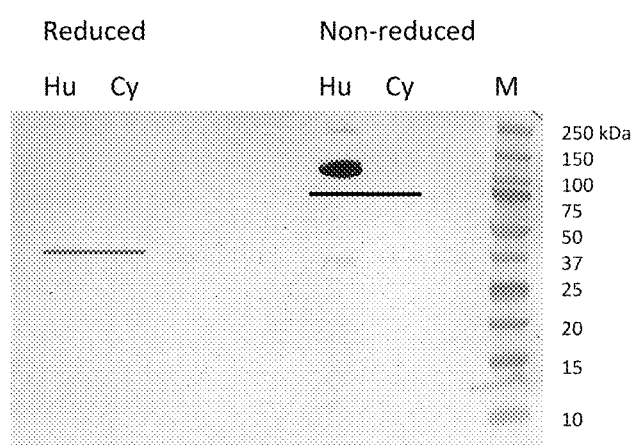
Figure 3C:
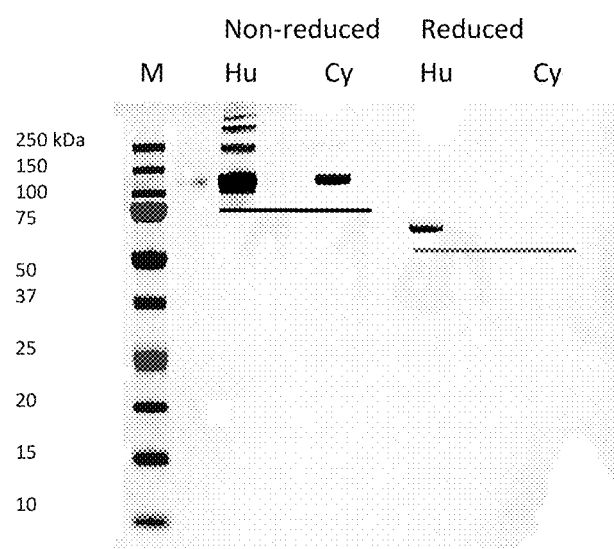

The samples of the recombinant human and cynomolgus EpCAM-Fc antigens were either reduced or non-reduced before loading on SDS-PAA gels (1 μg/well). The samples were run in duplicate. After electroblotting, the membranes were blocked with 5% skimmed milk powder (Merck product no 1.15363.0500) in PBS (block solution) for 1 hr. The membrane was then incubated with the IgGs 3-17I (FIG. 3A), MT201 (FIG. 3B) or MOC 31 (FIG. 3C) at a concentration of 1 μg/ml diluted in block solution. To detect the membrane bound IgG, the filter was incubated for 1 hr with a goat anti-human kappa-HRP antibody (Southern Biotech, cat no 2060-05) diluted 1:5000 in block solution.

Between all incubations the membrane was washed with PBS-T (PBS supplemented with 0.05% Tween-20; Medicago #09-9410-100) 3 times for 5 min. All incubations were performed at room temperature for 1 hr if not otherwise indicated.

The Western blots were developed using DAB (Thermo Scientific #1856090) substrate diluted according to the recommendations of the manufacturer.

For control, an SDS-PAA gel was stained with Coomassie Instant Blue (Expedeon #ISB01 L), to verify the loaded amounts of the EpCAM variants. The successful transfer to the membrane was verified by detecting the EpCAM-Fc on the membrane with a goat anti-human IgG-HRP conjugate (Southern Biotech cat no 2040-05) and DAB staining (data not shown). The expected sizes for EpCAM-Fc were approximately 110 kDa and 55 kDa under non-reducing and reducing conditions, respectively.

Western blot analysis demonstrated that antibody 3-17I bound equally well to both human and cynomolgus EpCAM under non-reducing conditions. In contrast, no binding of 3-17I IgG was observed to any reduced EpCAM antigen. The antibody MOC31 demonstrated different antigen-binding patterns. Unlike 3-17I IgG, it bound human EpCAM both under non-reducing and reducing conditions. It also recognized the cynomolgus antigen but only under non-reducing conditions. In addition, the weaker band intensity of the cynomolgus antigen staining indicated weaker binding to cynomolgus EpCAM than to the human antigen. The antibody MT201 IgG only demonstrated binding to the human EpCAM under non-reducing conditions. No binding of this antibody to the cynomolgus antigen was detected.

These results suggest that both MOC31 and MT201 bind to different epitopes on human EpCAM than 3-17I. This evidence is particularly strong when comparing 3-171 and MOC-31.

ELISA and Cross Reactivity

To determine the specificity and affinity of 3-17I, MT201 and MOC31 to human and cynomolgus EpCAM, a set of ELISA experiments was performed. All antibodies in IgG1 format as well as the human and cynomolgus EpCAM antigens were produced and purified as previously indicated (see Examples 1 and 2 and earlier in Example 3).

The specificity of antibody clones 12-C15 IgG, 16-G5 IgG and 17-C20 IgG for human EpCAM were determined in ELISA experiments. The specificity and affinity of antibody clones 7-F17, 17-C20 and 24-G6 in scFv format for human and cynomolgus EpCAM were determined in ELISA experiments.

For ELISA of antibodies in IgG format, the MAXI-sorb plate was coated with 1 µg/ml (100 µl per well) of human or cynomolgus EpCAM-Fc in PBS overnight at 4° C. The plates were blocked with 3% BSA in PBS for 2 hrs. The IgGs to be tested were added in 2-fold dilutions from 133 nM to 32 fM and incubated for 1 hr at room temperature. For detection of bound IgG, a goat anti-human kappa-HRP antibody (Southern Biotech, cat no 2060-05) was added in 1:5000 dilution in block solution and incubated for 1 hr at room temperature.

For ELISA of antibodies in scFv format, the MAXI-sorb plate was coated with 5 µg/ml (100 µl per well) of human or cynomolgus EpCAM-Fc in PBS overnight at 4° C. The plates were blocked with 4% skimmed milk (Merck product no 1.15363.0500) in PBS for 2 hrs. The scFvs to be tested were added in 2-fold dilutions from 667 nM to 3.2 nM and incubated with 0.125 µg mouse anti-cMyc IgG (clone 9E10 Diatec) for 1 hr at room temperature. For detection of bound scFv, a rabbit anti-mouse-HRP antibody (Dako, cat no P0260) was added in 1:3000 dilution in block solution and incubated for 1 hr at room temperature.

Between all incubations the plates were washed with PBS-T (0.05% Tween-20, Medicago #09-9410-100) three times. All incubations were performed at room temperature for one hour unless otherwise indicated.

The ELISA of antibodies in IgG format was developed using a 1-step ABTS Kit (Thermo Scientific prod #37615) and a 25 min incubation time. The absorbance was measured on a SLT SPECTRA plate reader. The software Prism (GraphPad, San Diego, Calif.) was used to estimate the affinities using a non-linear fit of one-site model on the retrieved ELISA data.

The ELISA of antibodies in scFv format was developed using a TMB substrate kit (Thermo Scientific, prod #34021) and a 10 min incubation time. The reaction was stopped by adding H2S04. The absorbance was measured on a SLT SPECTRA plate reader. The software Prism (GraphPad, San Diego, Calif.) was used to estimate the affinities using a non-linear fit of one-site model on the retrieved ELISA data.

Figure 4A:
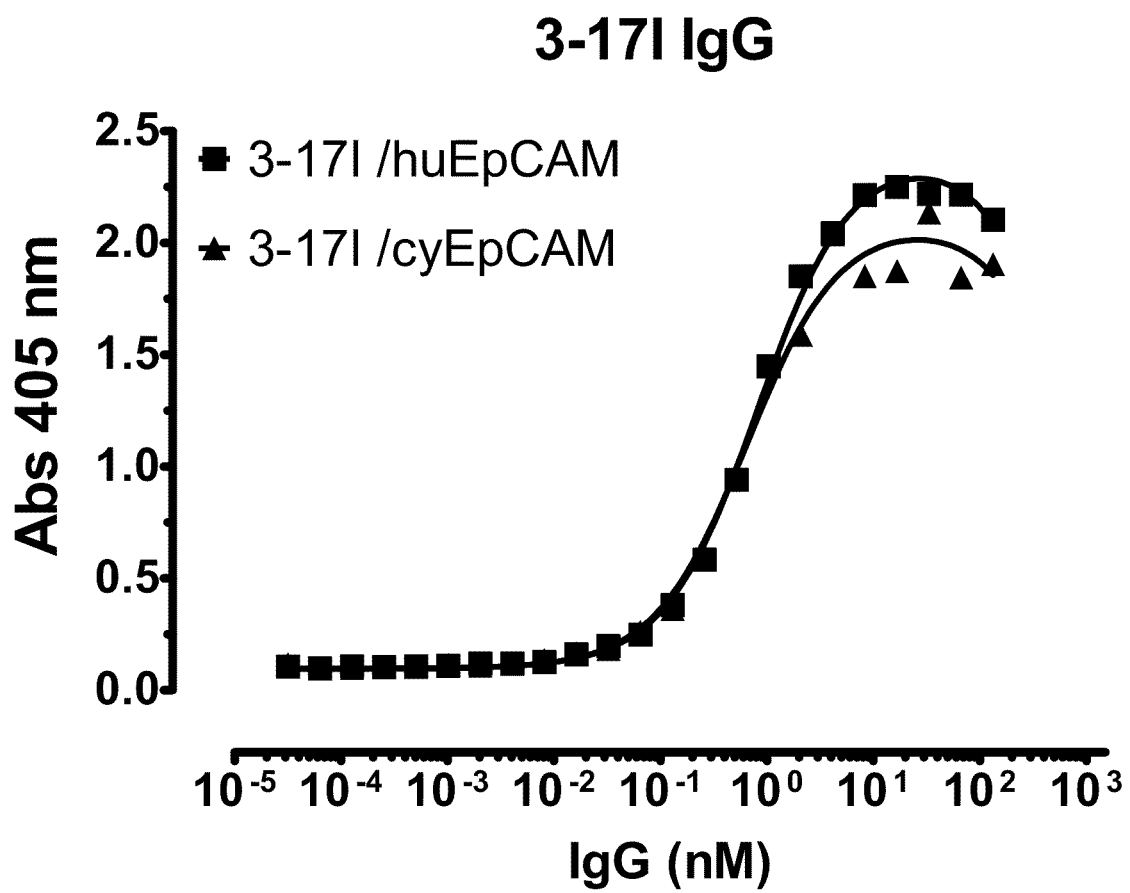
Figure 4B:
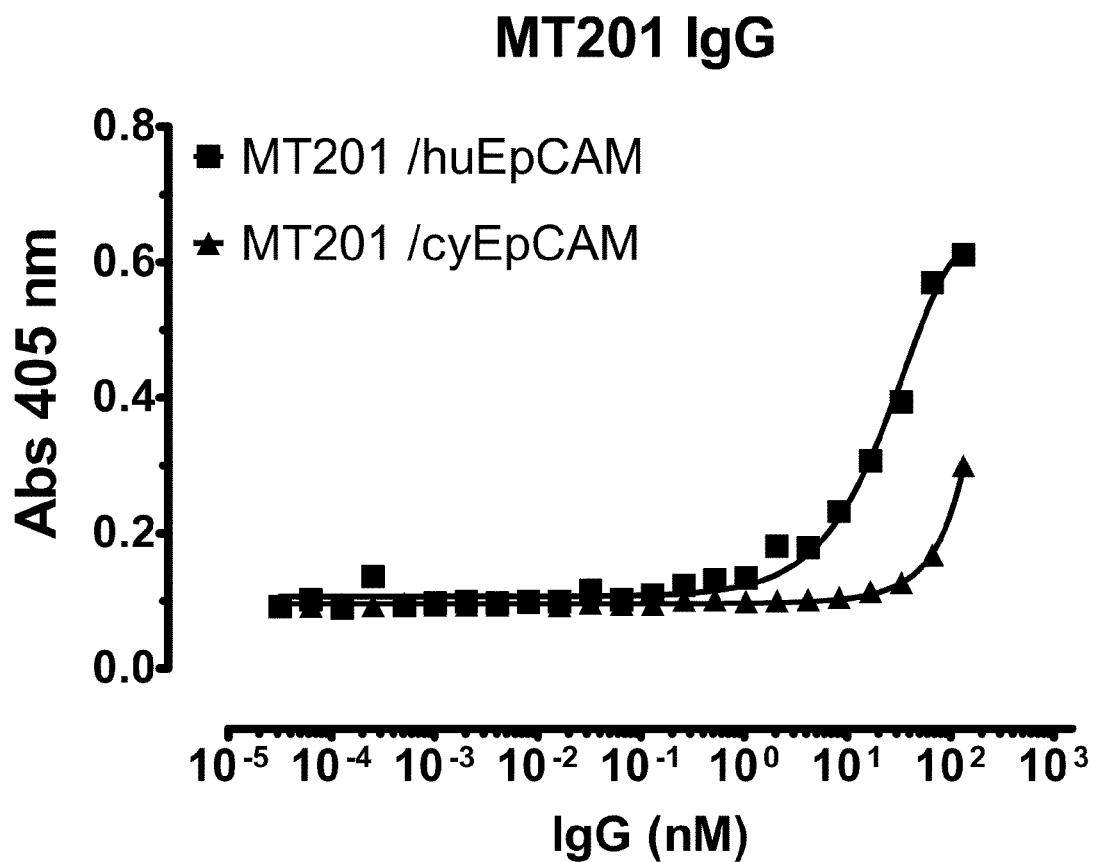
Figure 4C:
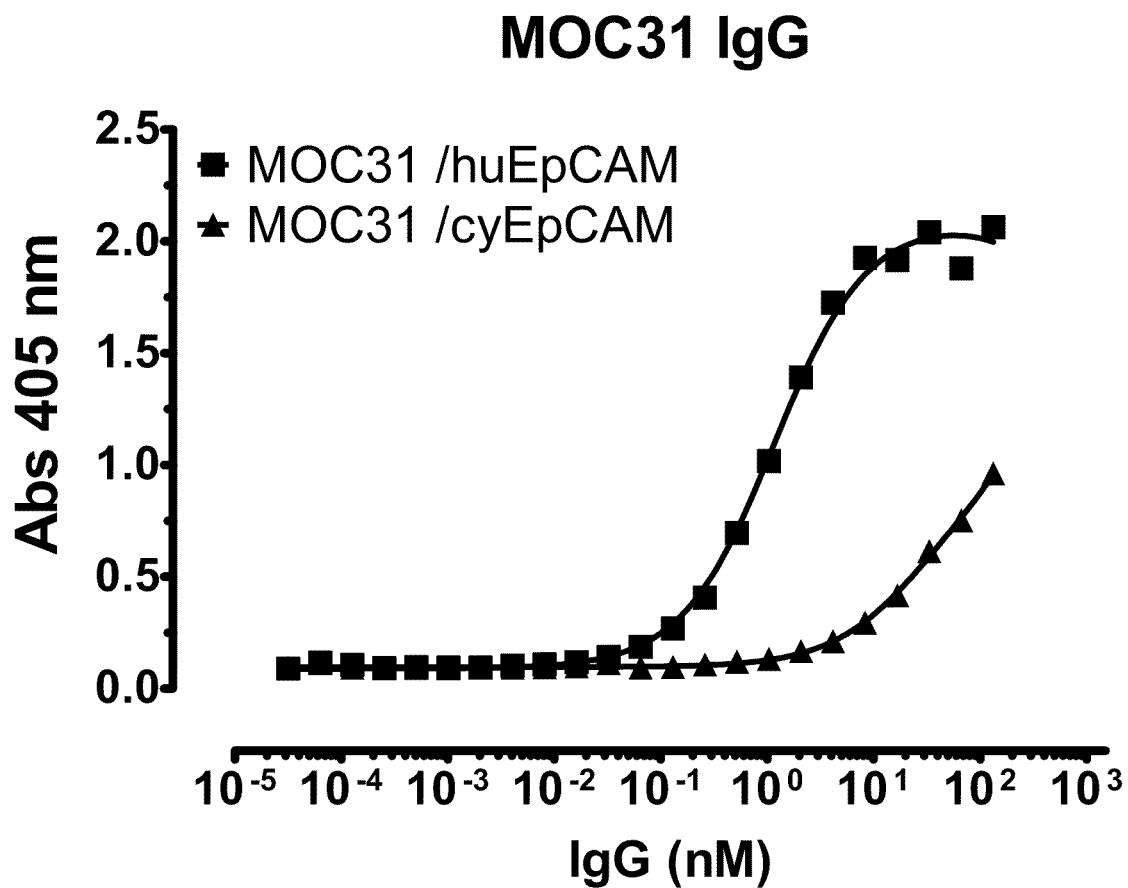

Conclusion:

The ELISA data demonstrated comparably good binding of 3-17I IgG to both human and cynomolgus EpCAM (FIG. 4A). In contrast, MOC31 antibody showed a significant difference in binding patterns to human and cynomolgus antigens (FIG. 4C), thus indicating a significantly lower affinity to cynomolgus EpCAM. Interestingly, the antibody MT201 showed only relatively weak binding to human EpCAM and no binding of this antibody to the cynomolgus antigen was detected (FIG. 4B).

The IgG format of antibody clones 12-C15, 16-G5 and 17-C20 also bound to human EpCAM (FIG. 9). The scFv format of antibody clones 7-F17, 17-C20 and 24-G6 bound to human and cynomolgus EpCAM and displayed affinities for both human and cynomolgus EpCAM which were comparable to the affinity of the scFv format of 3-17I for both human and cynomolgus EpCAM (FIGS. 10A and 10B).

Affinities

Figure 5A:
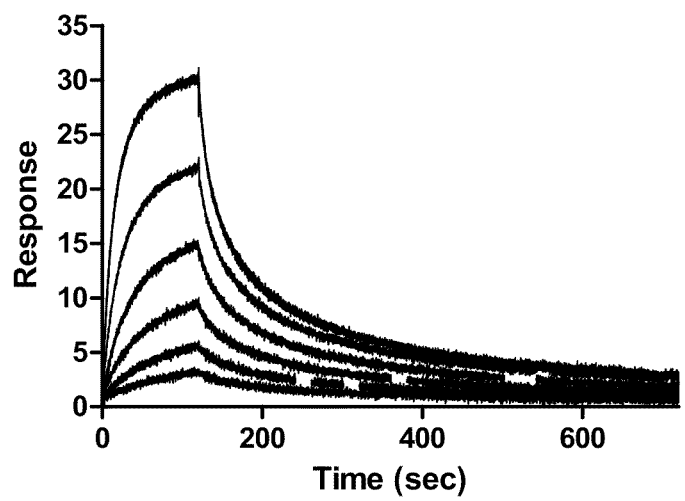
FIGS. 5A and 5B show BIAcore analysis of 3-17I IgG binding to recombinant human EpCAM antigen (FIG. 5A) or to recombinant cynomolgus EpCAM antigen (FIG. 5B). The shown binding curves correspond to 3-17I IgG concentrations of 7.8, 3.9, 2.0, 0.98, 0.49 and 0.24 nM.
Figure 5B:
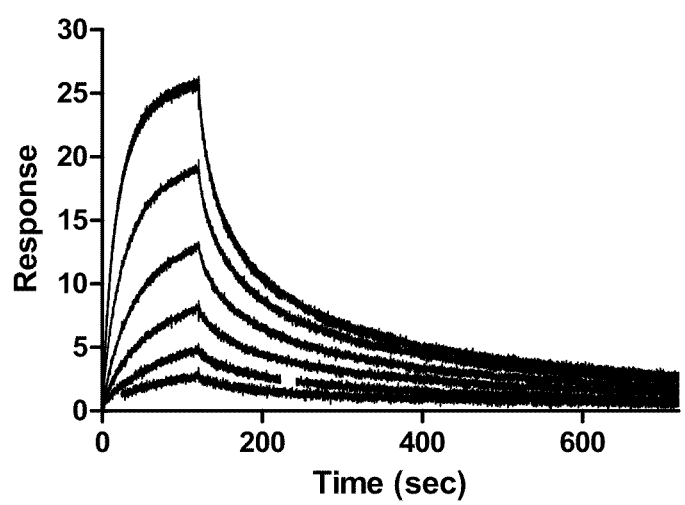

Binding of 3-17I to human and cynomolgus monkey EpCAM was analyzed using surface plasmon resonance (SPR) on a BIAcore T100 (BIAcore, Inc, Piscataway, N.J.). The extracellular domains of human or cynomolgus monkey EpCAM fused to human Fc (IgG1), were coupled to a CM5 chip (BIAcore, Inc, Piscataway, N.J.) at density of 100 RU. The SPR studies were performed using standard techniques at 37° C. with a flow rate of 50 µl/min. The data were analyzed using the 1:1 Langmuir binding model of the BIAcore software. The results from the kinetic analysis demonstrated that 3-17I IgG bound both human and cynomolgus EpCAM with almost the same on-rates ($k_{on}$) and off-rates ($k_{off}$) values thus providing the equilibrium constants ($K_D$) close to 1 nM (see FIG. 5A and FIG. 5B and Table 8).

TABLE 8

Kinetic analysis of 3-17I IgG binding to human and cynomolgus EpCAM in BIAcore.

|  | $k_{on}$ (1/Ms) | koff (1/s) | $K_D$ (M) |
| --- | --- | --- | --- |
| EpCAM, Human | $3.0 \times 10^7$ | 0.030 | $1.0 \times 10^{-9}$ |
| EpCAM, cynomolgus | $2.5 \times 10^7$ | 0.023 | $9.3 \times 10^{-10}$ |

Thus, the binding affinity of the 3-17I IgG antibody of the invention as measured by BIAcore analysis is approximately 1 nM for binding to both human and monkey EpCAM. The binding affinity of MOC31 IgG for human EpCAM as measured by BIAcore is described in the art as being similar, i.e.

$K_D$=3 nM (Roovers et al., 1998, Brit. J. Cancer, 78:1407-1416). It can however be seen from the ELISA data above, that the binding affinity of MOC31 IgG for monkey EpCAM is significantly lower than that of 3-17I. The binding affinity of MT201 IgG for human EpCAM as measured by BIAcore is described in the art as being much lower, i.e. $K_D$=175 nM (Naundorf et al., 2002, Int. J. Cancer, 100:101-110).

EXAMPLE 4

3-17I IgG Mediates ADCC and CDC

Functional assays were carried out in order to determine the ability of 3-17I IgG to mediate target cell killing via ADCC and/or CDC. Results from these studies show that 3-17I IgG does mediate ADCC and CDC. In addition, these data clearly show the superiority of 3-17I IgG over MT201 IgG in inducing both ADCC and CDC.

ADCC (Antibody-Dependent Cellular Cytotoxicity)

The ability of 3-17I IgG to induce ADCC was analyzed using three different breast cancer cell lines MDA-MB-231, MDA-453 and BT-474 which cover a range of more than 100-fold difference in surface density of EpCAM (Prang et al., 2005). MT201 IgG was used as a positive control antibody as it was reported by Prang et al to induce ADCC on all these cell lines. The MDA-MB-453 (breast mammary gland, ATCC number HTB-131), MDA-MB-231 (breast mammary gland, ATCC number HTB-26) and BT-474 (breast mammary gland, ATCC number HTB-20) cell lines were obtained from the American Type Culture Collection (ATCC, Rockville, Md.).

The MDA-MB-453 and BT-474 cells were maintained in RPMI-1640 culture medium and the MDA-MB-231 cells were maintained in Leibovitz's culture medium. All media were supplemented with 10% fetal calf serum (FCS), Penicillin and Streptomycin. All cell media and supplements were obtained from PAA (Pasching, Austria). The target cells, cultivated under regular conditions, were harvested by Trypsin-EDTA, sedimented by centrifugation and resuspended twice in RPMI-1640 culture medium. 1 ml containing $2.5 \times 10^6$ cells was mixed with calcein-AM (Invitrogen, Carlsbad, Calif.) to a final concentration of 10 µM and then incubated at 37° C. for 30 min on a vertical rotating wheel (7 rpm). The cells were washed three times in RPMI-1640 with 10% FCS and the cell density was adjusted to $3 \times 10^5$ per ml.

The peripheral blood mononuclear cells (PBMC) were prepared from blood of a single healthy volunteer by Ficoll-Hypaque gradient centrifugation. The isolated PBMC were washed in RPMI-1640 with 10% FCS and resuspended at $6 \times 10^6$ cells per ml. 50 µl of each target and effector cell suspension were added to the same wells in a 96-well microtiter plate providing a ratio of effector (E) to target (T) cells (E:T) of 20:1.

The antibody dilutions were added in a volume of 20 µl in quadruplicates for each concentration. The microtiter plate was then incubated for 4 hrs at 37° C., and 20 µl 0.9% TritonX-100 was added to some of the wells after 3 hrs 45 minutes to achieve complete lysis of the target cells. 100 µl of the supernatant of each sample was then transferred to a black microtiter plate and the fluorescence (excitation: 488 nm, emission: 518 nm) was analyzed in a TECAN M200 plate reader. The fluorescence intensity in the samples with no antibodies was subtracted from the intensity of all other samples. The percentage of lysis in samples with antibodies was estimated on the basis of fluorescence intensity in the samples with 100% cell lysis after treatment with TritonX-100. The dose-response curves were generated by nonlinear regression analysis using a three-parameter fit model of software Prism (GraphPad, San Diego, Calif., USA).

Figure 6A:
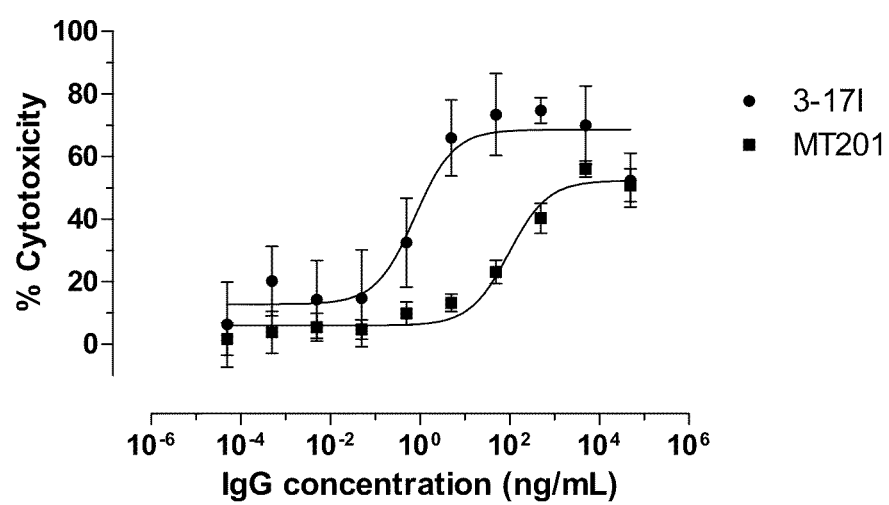
FIGS. 6A, 6B and 6C show that 3-17I IgG induces ADCC in MDA-MB-453 (FIG. 6A), MDA-MB-231 (FIG. 6B) and BT-474 (FIG. 6C) cells in the presence of human PBMCs. Furthermore, these data demonstrate that 3-171 g possesses superior ADCC activity over the positive control antibody, MT201 IgG.
Figure 6B:
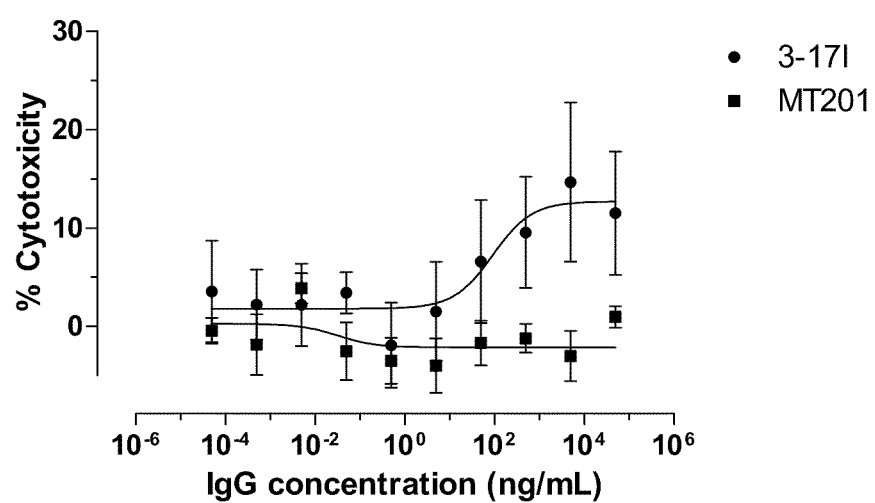
Figure 6C:
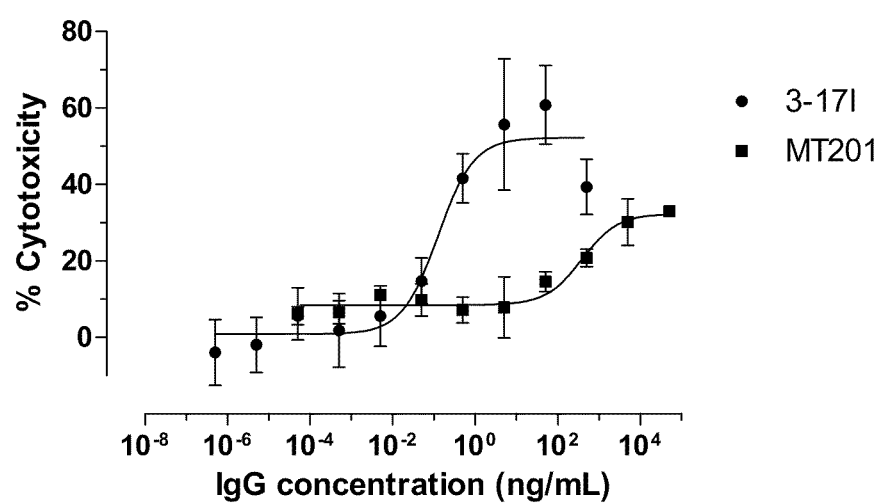

The results shown in FIGS. 6A, 6B and 6C clearly demonstrate that 3-17I IgG induces ADCC in all the three cell lines MDA-MB-453 (FIG. 6A), MDA-MB-231 (FIG. 6B) and BT-474 (FIG. 6C) in the presence of human PBMCs. $EC_{50}$ values were estimated to be 0.08 ng/ml, 15 ng/ml and 0.12 ng/ml for these cell lines, respectively. The achieved maximum killing was 75%, 92% and 61%, respectively. The control, antibody MT201, demonstrated much inferior ADCC activity with $EC_{50}$ values of 7 ng/ml and 382 ng/ml and maximum killing of 56% and 33% for the cell lines MDA-MB-453 and BT-474, respectively. No killing of MDA-MB-231 cells with lowest level of EpCAM expression was observed for antibody MT201. These data clearly show the superiority of 3-17I IgG over MT201 IgG in inducing ADCC.

CDC (Complement-Dependent Cytotoxicity)

The ability of 3-17I IgG to induce complement dependent cytotoxicity (CDC) was analyzed using two cell lines KATO III and MT-3. Three related antibody clones, 12-C15 IgG, 16-G5 IgG and 17-C20 IgG were also tested for their ability to induce CDC using the KATO III cell line. MT201 IgG was used as a positive control antibody as it was reported by Prang et al (2005) to induce CDC on these cell lines. KATO III (gastric carcinoma, ATCC number HTB-103) and MT-3 (breast carcinoma, DSMZ number ACC 403) cell lines were obtained from the American Type Culture Collection (ATCC, Rockville, Md.) and DSMZ (Braunschweig, Germany), respectively. The KATO III and MT-3 cells were maintained in RPMI-1640 culture medium with the addition of fetal calf serum (FCS) at 20% and 10%, respectively. All media were supplemented with Penicillin and Streptomycin. All cell media and supplements were obtained from PAA (Pasching, Austria).

The target cells cultivated under regular conditions were sedimented by centrifugation and resuspended twice in RPMI-1640 culture medium. 5 ml containing $12.5 \times 10^6$ cells were mixed with calcein-AM (Invitrogen, Carlsbad, Calif.) to a final concentration of 10 µM and then incubated at 37° C. for 30 min on a vertical rotating wheel (7 rpm). The cells were washed three times in RPMI-1640 with 10% heat inactivated fetal calf serum (hiFCS) and the cell density was adjusted to $4 \times 10^6$/ml. 25 µl of target cell suspension was mixed with 25 µl human serum and 50 µl antibody dilutions in RPMI-1640 with 10% hiFCS. For experiments using the 3-17I IgG antibody, the final antibody concentrations in the wells ranged from 0.8 ng/ml to 50 µg/ml. For experiments using antibody clones 12-C15 IgG, 16-G5 IgG and 17-C20 IgG, the final antibody concentration in the wells ranged from 0.19 µg/ml to 1.5 µg/ml. The assays were performed in quadruplicate. 20 µl of 0.9% TritonX-100 was added to some wells to achieve complete lysis of the target cells and the plate was then incubated for one hour at 37° C. 100 µl of RPMI-1640 with 10% hiFCS was added to the wells to increase the volume and the cells were then sedimented by centrifugation. 100 µl of the supernatant was transferred to a black microtiter plate and the fluorescence (excitation: 488 nm, emission: 518 nm) was analyzed using TECAN M200 plate reader. The fluorescence intensity in the samples with no antibodies was subtracted from the intensity of all other samples. The percentage of lysis in samples with antibodies was estimated on the basis of fluorescence intensity in the samples with 100% cell lysis after treatment with TritonX-100. The dose-response curves were generated by nonlinear regression analysis using a three-parameter fit model of software Prism (GraphPad, San Diego, Calif., USA).

Figure 7A:
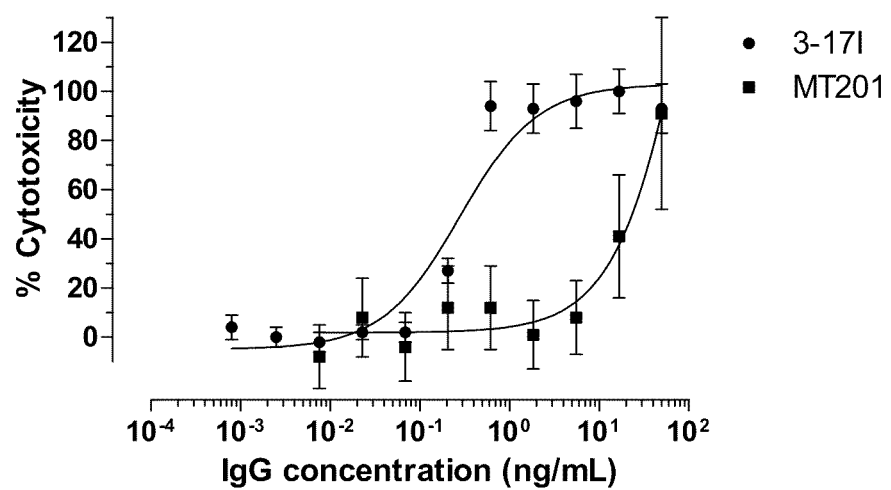
FIGS. 7A and 7B show that 3-17I IgG induces CDC in the cell lines KATO III (FIG. 7A) and MT-3 (FIG. 7B) in the presence of human serum. Furthermore, these data clearly demonstrate the superiority of 3-17I IgG over positive control antibody, MT201 IgG, in inducing CDC.
Figure 7B:
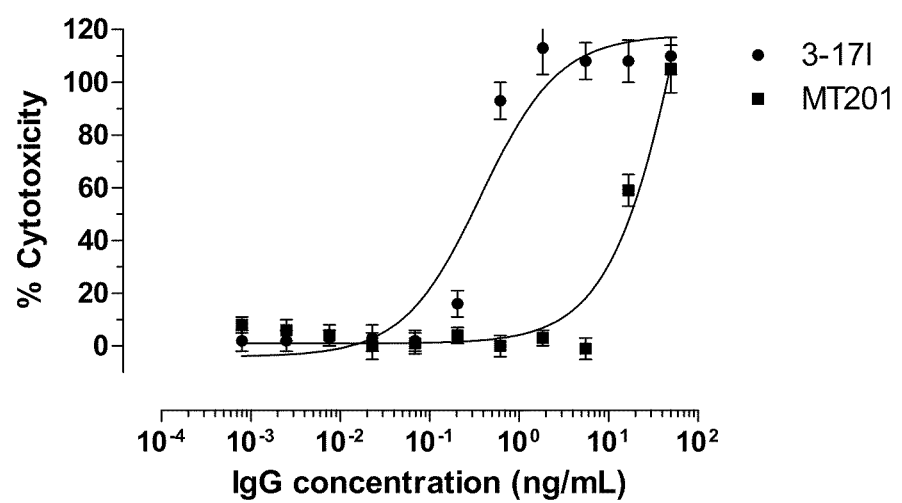

The results shown in FIGS. 7A and 7B clearly demonstrate that 3-17I IgG induces CDC in the cell lines KATO III (FIG. 7A) and MT-3 (FIG. 7B) in the presence of human serum. CDC activity was also demonstrated for antibody clones 12-C15 IgG, 16-G5 IgG and 17-C20 IgG in the KATOIII cell line.

Although both antibodies 3-17I IgG and MT201 were able to induce 100% lysis of target cells by complement, the killing effect was achieved at significantly different antibody concentrations. While the $EC_{50}$ values for 3-17I IgG were estimated to be 0.28 ng/ml and 0.38 ng/ml for KATO III and MT-3 cells, respectively, the control antibody, MT201, showed CDC at 250-fold higher concentrations with $EC_{50}$ values of 76 ng/ml and 89 ng/ml for the same two cell lines, respectively. These data clearly show the superiority of 3-17I IgG over MT201 IgG in inducing CDC.

References

The following references, to the extent that they provide exemplary procedural or other details supplementary to those set forth herein, are specifically incorporated herein by reference.

Altschul, Madden, Schaffer, Zhang, Zhang, Miller, Lipman, "Gapped BLAST and PSI-BLAST: a new generation of protein database search programs", *Nucleic Acids Res.,* 25:3389-3402, 1997.

Arbabi-Ghahroudi, Desmyter, Wyns, Hamers, Muyldermans, "Selection and identification of single domain antibody fragments from camel heavy-chain antibodies", *FEBS Lett.,* 414:521-526, 1997.

Baeverle and Gires, BJC, 96: 417-423, 2007.

Baldari, Murray, Ghiara, Cesareni, Galeotti, "A Novel Leader Peptide Which Allows Efficient Secretion of a Fragment of Human Interleukin 1 Beta in *Saccharomyces Cerevisiae*", *EMBO J.,* 6:229-234, 1987

Beckman, Weiner and Davis, "Antibody Constructs in Cancer Therapy", *Cancer,* 109(2):170-179, 2006.

Brinster, Chen, Trumbauer, Yagle, Palmiter, "Factors Affecting the Efficiency of Introducing Foreign DNA into Mice by Microinjecting Eggs", *Proc. Natl. Acad. Sci. USA,* 82(13):4438-4442, 1985.

Carillo and Lipton, "The Multiple Sequence Alignment Problem in Biology", *SIAM J. Applied Math.,* 48:1073, 1988.

Cullen, Gray, Wilson, Hayenga, Lamsa, Rey, Norton, Berka, "Controlled Expression and Secretion of Bovine Chymosin in *Aspergillus Nidulans*", *BioTechnology,* 5:369, 1987.

Davies and Cohen, "Interactions of protein antigens with antibodies," *Proc Natl. Acad. Sci. U.S.A.* 93:7-12, 1996.

Davies, Padlan, Sheriff, "Antibody-antigen complexes," *Annu. Rev. Biochem.* 59:439-473, 1990.

Davies and Riechmann, "Antibody VH domains as small recognition units", *Biotechnology (NY),* 13:475-479, 1995.

Devereux, Haeberli, Smithies, "A Comprehensive Set of Sequence Analysis Programs for the VAX", Nucleic Acids Res., 12:387, 1984.

Di Paolo et al., "A recombinant immunotoxin derived from a humanized epithelial cell adhesion molecule-specific single-chain antibody fragment has potent and selective antitumor activity", Clin Cancer Res 9: 2837-48, 2003.

Frische, Meldal, Werdelin, Mouritsen, Jensen, Galli-Stampino, Bock, "Multiple Column Synthesis of a Library of T-Cell Stimulating Tn-Antigenic Glycopeptide Analogues for the Molecular Characterization of T-Cell-Glycan Specificity", *J. Pept. Sci.,* 2(4): 212-22, 1996.

Goeddel, "Gene Expression Technology: Methods in Enzymology 185, *Academic Press, San Diego, Calif.,* 1990.

Hamers-Casterman and Atarhouch, "Naturally Occurring antibodies Devoid of Light Chains", *Nature,* 363(6428): 446-448, 1993.

Hammer, Pursel, Rexroad, Wall, Bolt, Ebert, Palmiter, Brinster, "Production of Transgenic Rabbits, Sheep and Pigs by Microinjection", *Nature,* 315:680-683, 1985.

Henikoff and Henikoff, "Amino acid Substitution Matrices from Protein Blocks", *Proc. Natl. Acad. Sci. USA,* 89:10915-10919, 1992.

Hinnen, Hicks, Fink, "Transformation of Yeast", *Proc. Natl. Acad. Sci. USA,* 75:1929, 1978.

Holliger and Hudson, "Engineered Antibody Fragments and the Rise of Single Domains", *Nature Biotechnology,* 23(9): 1126-1136, 2005.

Holm, "Dali: a Network Tool for Protein Structure Comparison", *Trends in Biochemical Sciences,* 20:478-480, 1995.

Holm, "Protein Structure Comparison by Alignment of Distance Matrices", *J. Mol. Biol.,* 233:123-38, 1993

Holm, "Touring Protein Fold Space With Dali/FSSP", *Nucleic Acid Res.,* 26:316-9, 1998.

Ito, Fukuda, Murata, Kimura, "Transformation of Intact Yeast Cells Treated with Alkali Cations", *J. Bacteriol.,* 153:163-168, 1983.

Kabat, Wu, Perry, Gottesman, Foeller, "Sequences of Proteins of Immunological Interest", 5th Ed. *Public Health Service, National Institutes of Health, Bethesda, Md.,* 647-669, 1991.

Kaufman, Murtha, Davies, "Translational Efficiency of Polycistronic Mrnas and Their Utilization to Express Heterologous Genes in Mammalian Cells", *EMBO J.,* 6:187-195, 1987.

Kiss, Fisher, Pesavento, Dai, Valero, Ovecka, Nolan, Phipps, Velappan, Chasteen, Martinez, Waldo, Pavlik, Bradbury, "Antibody binding loop insertions as diversity elements", *Nucleic Acids Research,* 34(19):e132, 2006.

Kurjan and Herskowitz, "Structure of a Yeast Pheromone Gene (MFa): a Putative α-Factor Precursor Contains Four Tandem Copies of mature α-Factor", *Cell,* 30:933-943, 1982.

Le Gall, Reusch, Little and Kipriyanov, "Effect of Linker Sequences Between the Antibody Variable Domains on the Formation, Stability and Biological Activity of a Bispecific Tandem Diabody", *Protein Engineering, Design & Selection,* 17(4):357-366, 2004.

Luckow and Summers, "High Level Expression of Nonfused Foreign Genes with *Autographa Californica* Nuclear Polyhedrosis Virus Expression Vectors", *Virology,* 170:31-39, 1989.

Marhaba et al., "CD44 and EpCAM: cancer-initiating cell markers", Curr Mol Med 8: 784-804, 2008.

Merrifield, "Solid Phase Peptide Synthesis 1. Synthesis of a Tetrapeptide", *J. Am. Chem. Assoc.,* 85:2149-2154, 1964.

Munz et al., "The carcinoma-associated antigen EpCAM upregulates c-myc and induces cell proliferation", Oncogene 23: 5748-58, 2004.

Myers and Miller, "Optical Alignments in Linear Space", *CABIOS,* 4:11-17, 1988.

Needleman and Wunsch, "A General Method Applicable to the Search For Similarities in the Amino Acid Sequence of Two Proteins", *J. Mol. Biol.,* 48:443, 1970.

Neuberger and Milstein, "Somatic hypermutation," *Curr. Opin. Immunol.,* 7:248-254, 1995.

Nicaise, Valerio-Lepiniec, Minard, Desmadril, "Affinity transfer by CDR grafting on a nonimmunoglobulin scaffold", *Protein Sci.,* 13: 1882-1891, 2004.

O'Brien et al., "A human colon cancer cell capable of initiating tumour growth in immunodeficient mice", Nature 445: 106-10, 2007.

Palmiter and Brinster, "Transgenic Mice", *Cell*, 41:343-345, 1985.

Palmiter, Norstedt, Gelinas, Hammer, Brinster, "Metallothionein-Human GH Fusion Genes Stimulate Growth of Mice", *Science*, 222:809-814, 1983.

Pearson and Lipman, "Improved tools for biological sequence analysis", *Proc. Natl. Acad. Sci. USA*, 85:2444-2448, 1988.

Pearson, "Rapid and sensitive sequence comparison with FASTP and FASTA", *Methods in Enzymology*, 183:63-98, 1990.

Prang, Preithner, Brischwein, Göster, Wöppel, Müller, Steiger, Peters, Baeuerle, da Silva, "Cellular and complement-dependent cytotoxicity of Ep-CAM-specific monoclonal antibody MT201 against breast cancer cell lines", Br J Cancer, 92(2):342-349, 2005.

Qiu, Wang, Cai, Wang, Yue, "Small antibody mimetics comprising two complementarity-determining regions and a framework region for tumor targeting, *Nature Biotechnology*, 25(8): 921-929, 2007.

Reff and Heard, "A Review of Modifications to Recombinant Antibodies: Attempt to Increase Efficacy in Oncology Applications", *Critical Reviews in Oncology Hematology*, 40:25-35, 2001.

Reiter, Ulrich Brinkmann, Lee and Pastan, "Engineering Antibody Fv Fragements for Cancer Detection and Therapy: Disulfide-Stabilized Fv Fragments", *Nature Biotechnology*, 14:1239-1245, 1996.

Schultz, Tanner, Hofmann, Emini, Condra, Jones, Kieff, Ellis, "Expression and Secretion in Yeast of a 400-Kda Envelope Glycoprotein Derived from Epstein-Barr Virus", *Gene*, 54:113-123, 1987.

Seed, "an LFA-3 Cdna Encodes a Phospholipid-Linked Membrane Protein Homologous to its Receptor CD2", *Nature*, 329:840, 1987.

Sinkar, White, Gordon, "Molecular Biology of Ri-Plasmid a Review", *J. Biosci(Bangalore)*, 11:47-58, 1987.

Smith and Waterman, "Comparison of Biosequences", *Adv. Appl. Math.*, 2:482, 1981.

Smith, Summers, Fraser, "Production of Human Beta Interferon in Insect Cells Infected With Baculovirus Expression Vector", *Mol. Cell. Biol.*, 3:2156-2165, 1983.

Spizzo et al., "High Ep-CAM expression is associated with poor prognosis in node-positive breast cancer", Breast Cancer Res Treat 86: 207-13, 2004.

Spizzo et al., "Overexpression of epithelial cell adhesion molecule (Ep-CAM) is an independent prognostic marker for reduced survival of patients with epithelial ovarian cancer", Gynecol Oncol 103: 483-8, 2006.

Thompson, Higgins, Gibson, "CLUSTAL W: Improving the sensitivity of progressive multiple sequence alignment through sequence weighting, position-specific gap penalties and weight matrix choice", *Nucleic Acids Res.*, 22:4673-4680, 1994.

van den Beucken, Neer, Sablon, Desmet, Celis, Hoogenboom, Hufton, "Building novel binding ligands to B7.1 and B7.2 based on human antibody single variable light chain domains", *J. Mol. Biol.*, 310:591-601, 2001.

Varga et al., "Overexpression of epithelial cell adhesion molecule antigen in gallbladder carcinoma is an independent marker for poor survival", Clin Cancer Res 10: 3131-6, 2004.

Wagner, Milstein, Neuberger, "Codon bias targets mutation," Nature, 376:732, 1995.

Ward, Güssow, Griffiths, Jones, Winter, "Binding Activities of a Repertoire of Single Immunoglobulin Variable Domains Secreted from *Escherichia Coli*", Nature, 341 (6242):544-546, 1989.

Went et al., "Frequent high-level expression of the immunotherapeutic target Ep-CAM in colon, stomach, prostate and lung cancers", Br J Cancer 94: 128-35, 2006.

Young, MacKenzie, Narang, Oomen and Baenziger, "Thermal Stabilization of a Single-Chain Fv Antibody Fragment by Introduction of a Disulphide Bond", *FEBS Letters*, 16396(377):135-139, 1995.

Zambryski, Herrera-Estreila, DeBlock, Van Montagu, Schell "Genetic Engineering, Principles and Methods", *Hollaender and Setlow (eds.)*, Vol. VI, pp. 253-278, Plenum Press, New York, 1984.

Zapata, Ridgway, Mordenti, Osaka, Wong, Bennett, Carter, "Engineering Linear F(Ab')$_2$ Fragments For Efficient Production in *Escherichia Coli* and Enhanced Antiproliferative Activity", *Protein Eng.*, 8(10):1057-1062, 1995.

Zhang, Gildersleeve, Yang, Xu, Loo, Uryu, Wong, Schultz, "A New Strategy for the Synthesis of Glycoproteins", *Science*, 303(5656): 371-373, 2004.

The invention claimed is:

1. An antibody that binds to EpCAM and that comprises at least one heavy chain variable region that comprises three CDRs and at least one light chain variable region that comprises three CDRs, wherein said heavy chain variable region comprises:
   (a) a variable heavy (VH) CDR1 that has the amino acid sequence of SEQ ID NO:5,
   (b) a VH CDR2 that has the amino acid sequence of SEQ ID NO:6, and
   (c) a VH CDR3 that has the amino acid sequence of SEQ ID NO:7.

2. The antibody of claim 1, wherein one or more of said light chain variable region CDRs are selected from the group consisting of:
   (d) a variable light (VL) CDR1 that has the amino acid sequence of SEQ ID NO:8,
   (e) a VL CDR2 that has the amino acid sequence of SEQ ID NO:38, and
   (f) a VL CDR3 that has the amino acid sequence of SEQ ID NO:90.

3. The antibody of claim 1, wherein one of said light chain variable region CDRs is variable light (VL) CDR1 that has the amino acid sequence of SEQ ID NO:8.

4. The antibody of claim 2, wherein said VL CDR2 of (e) has the amino acid sequence of SEQ ID NO:9 or SEQ ID NO:29 and/or said VL CDR3 of (f) has the amino acid sequence of SEQ ID NO:10, 30, 43, 56, 69 or 82.

5. The antibody of claim 2, comprising one of each of the light chain CDR domains (d), (e), and (f).

6. The antibody of claim 1, wherein said three light chain variable region CDRs have the amino acid sequences of SEQ ID NOs: 8, 9 and 10, or SEQ ID NOs: 8, 29 and 30, or SEQ ID NOs: 8, 29 and 43, or SEQ ID NOs: 8, 29 and 56, or SEQ ID NOs: 8, 29 and 69, or SEQ ID NOs: 8, 29 and 82.

7. The antibody of claim 1, wherein said heavy chain variable region comprises the amino acid sequence of SEQ ID NO:3.

8. The antibody of claim 1, wherein said light chain variable region comprises the amino acid sequence of SEQ ID NO:4, 27, 40, 53, 66 or 79.

9. The antibody of claim 1, wherein said antibody comprises the amino acid sequence of SEQ ID NO:21, 36, 49, 62, 75 or 88.

10. The antibody of claim 1, wherein said antibody is capable of binding to both human and monkey EpCAM.

11. The antibody of claim 1, wherein said antibody is a fully human antibody.

12. The antibody of claim 1, wherein said antibody comprises all or a portion of an antibody heavy chain constant region and/or an antibody light chain constant region.

13. The antibody of claim 12, wherein said antibody is an IgG antibody.

14. The antibody of claim 13, wherein said antibody comprises a heavy chain that comprises the amino acid sequence of SEQ ID NO:24 and optionally a light chain that comprises the amino acid sequence of SEQ ID NO:25, 51, 64 or 77.

15. The antibody of claim 1, wherein said antibody is an antigen binding fragment of an antibody.

16. The antibody 15, wherein said antigen binding fragment of said antibody is a Fab', Fab, F(ab')$_2$, single domain antibody, TandAbs dimer, Fv, scFv, dsFv, ds-scFv, Fd, linear antibody, minibody, diabody, bispecific antibody fragment, bibody, tribody, sc-diabody, kappa(lamda) body, BiTE, DVD-Ig, SIP, SMIP, or DART.

17. The antibody of claim 1, wherein said antibody is attached to at least a second diagnostic or therapeutic agent.

18. The antibody of claim 17, wherein said antibody is attached to a radiotherapeutic agent, chemotherapeutic agent, anti-angiogenic agent, apoptosis-inducing agent, anti-tubulin drug, anti-cellular or cytotoxic agent, steroid, cytokine, chemokine, ATPase inhibitor, another antibody, or coagulant.

19. The antibody of claim 1, wherein said antibody is comprised within a pharmaceutically acceptable composition.

20. An immunoconjugate comprising the antibody of claim 1 attached to at least a second therapeutic or diagnostic agent.

21. The immunoconjugate of claim 20, wherein said antibody is attached to a radiotherapeutic agent, chemotherapeutic agent, anti-angiogenic agent, apoptosis-inducing agent, anti-tublin drug, anti-cellular or cytotoxic agent, steroid, cytokine, chemokine, ATPase inhibitor, another antibody, or coagulant.

22. The immunoconjugate of claim 21, wherein said antibody is attached to another antibody and said immunoconjugate comprises a bispecific antibody or diabody.

23. A compostion comprising at least a first antibody according to claim 1 or an immunoconjugate thereof.

24. The compostion of claim 23, wherein said composition is a pharmaceutically acceptable composition.

25. The composition of claim 24, wherein said composition further comprises at least a second therapeutic agent.

26. A kit comprising, in at least a first container:
(a) the antibody of claim 1;
(b) an immunoconjugate comprising the antibody of claim 1 attached to at least a second therapeutic or diagnostic agent; or
(c) a composition comprising at least the antibody of claim 1 or an immunoconjugate thereof.

* * * * *

SEQUENCE LISTING

<160> NUMBER OF SEQ ID NOS: 97

<210> SEQ ID NO 1
<211> LENGTH: 345
<212> TYPE: DNA
<213> ORGANISM: Homo sapiens

<400> SEQUENCE: 1

```
caggtccagc tggtgcagtc tggggctgag gtgaagaagc ctgggtcctc ggtgaaggtc      60
tcctgcaagg cttctggagg cacccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaggcctt     300
ctatggaact actggggcca gggaaccctg gtcaccgtct cctca                     345
```

<210> SEQ ID NO 2
<211> LENGTH: 327
<212> TYPE: DNA
<213> ORGANISM: Homo sapiens

<400> SEQUENCE: 2

```
gaaattgtaa tgacacagtc tccagccacc ctgtctgtgt ctccagggga aagagccacc    60
ctctcctgca gggccagtca gagtgttagc agcaacttag cctggtacca gcagaaacct   120
ggccaggctc ccaggctcat catctatggt gcatccacca cggcctctgg tatcccagcc   180
aggttcagtg ccagtgggtc tgggacagac ttcactctca ccatcagcag cctgcagtct   240
gaagattttg cagtttatta ctgtcagcag tataataact ggcctccggc gtacactttt   300
ggccagggga ccaagctgga gatcaaa                                       327
```

<210> SEQ ID NO 3
<211> LENGTH: 115
<212> TYPE: PRT
<213> ORGANISM: Homo sapiens

<400> SEQUENCE: 3

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Leu Trp Asn Tyr Trp Gly Gln Gly Thr Leu Val Thr
            100                 105                 110

Val Ser Ser
        115
```

<210> SEQ ID NO 4
<211> LENGTH: 109
<212> TYPE: PRT
<213> ORGANISM: Homo sapiens

<400> SEQUENCE: 4

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Ile Ile
        35                  40                  45

Tyr Gly Ala Ser Thr Thr Ala Ser Gly Ile Pro Ala Arg Phe Ser Ala
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Ala Tyr Thr Phe Gly Gln Gly Thr Lys Leu Glu Ile Lys
            100                 105
```

-continued

<210> SEQ ID NO 5
<211> LENGTH: 5
<212> TYPE: PRT
<213> ORGANISM: Homo sapiens

<400> SEQUENCE: 5

Ser Tyr Ala Ile Ser
1               5

<210> SEQ ID NO 6
<211> LENGTH: 17
<212> TYPE: PRT
<213> ORGANISM: Homo sapiens

<400> SEQUENCE: 6

Gly Ile Ile Pro Ile Phe Gly Thr Ala Asn Tyr Ala Gln Lys Phe Gln
1               5                   10                  15

Gly

<210> SEQ ID NO 7
<211> LENGTH: 6
<212> TYPE: PRT
<213> ORGANISM: Homo sapiens

<400> SEQUENCE: 7

Gly Leu Leu Trp Asn Tyr
1               5

<210> SEQ ID NO 8
<211> LENGTH: 11
<212> TYPE: PRT
<213> ORGANISM: Homo sapiens

<400> SEQUENCE: 8

Arg Ala Ser Gln Ser Val Ser Ser Asn Leu Ala
1               5                   10

<210> SEQ ID NO 9
<211> LENGTH: 7
<212> TYPE: PRT
<213> ORGANISM: Homo sapiens

<400> SEQUENCE: 9

Gly Ala Ser Thr Thr Ala Ser
1               5

<210> SEQ ID NO 10
<211> LENGTH: 11
<212> TYPE: PRT
<213> ORGANISM: Homo sapiens

<400> SEQUENCE: 10

Gln Gln Tyr Asn Asn Trp Pro Pro Ala Tyr Thr
1               5                   10

<210> SEQ ID NO 11
<211> LENGTH: 30
<212> TYPE: PRT
<213> ORGANISM: Homo sapiens

<400> SEQUENCE: 11

Gln Val Gln Leu Val Gln Ser Gly Ala Glu Val Lys Lys Pro Gly Ser
1               5                   10                  15

```
Ser Val Lys Val Ser Cys Lys Ala Ser Gly Gly Thr Phe Ser
        20                  25                  30

<210> SEQ ID NO 12
<211> LENGTH: 14
<212> TYPE: PRT
<213> ORGANISM: Homo sapiens

<400> SEQUENCE: 12

Trp Val Arg Gln Ala Pro Gly Gln Gly Leu Glu Trp Met Gly
1               5                   10

<210> SEQ ID NO 13
<211> LENGTH: 32
<212> TYPE: PRT
<213> ORGANISM: Homo sapiens

<400> SEQUENCE: 13

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 14
<211> LENGTH: 11
<212> TYPE: PRT
<213> ORGANISM: Homo sapiens

<400> SEQUENCE: 14

Trp Gly Gln Gly Thr Leu Val Thr Val Ser Ser
1               5                   10

<210> SEQ ID NO 15
<211> LENGTH: 23
<212> TYPE: PRT
<213> ORGANISM: Homo sapiens

<400> SEQUENCE: 15

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 16
<211> LENGTH: 15
<212> TYPE: PRT
<213> ORGANISM: Homo sapiens

<400> SEQUENCE: 16

Trp Tyr Gln Gln Lys Pro Gly Gln Ala Pro Arg Leu Ile Ile Tyr
1               5                   10                  15

<210> SEQ ID NO 17
<211> LENGTH: 32
<212> TYPE: PRT
<213> ORGANISM: Homo sapiens

<400> SEQUENCE: 17

Gly Ile Pro Ala Arg Phe Ser Ala Ser Gly Ser Gly Thr Asp Phe Thr
1               5                   10                  15

Leu Thr Ile Ser Ser Leu Gln Ser Glu Asp Phe Ala Val Tyr Tyr Cys
            20                  25                  30
```

-continued

<210> SEQ ID NO 18
<211> LENGTH: 10
<212> TYPE: PRT
<213> ORGANISM: Homo sapiens

<400> SEQUENCE: 18

Phe Gly Gln Gly Thr Lys Leu Glu Ile Lys
1               5                   10

<210> SEQ ID NO 19
<211> LENGTH: 21
<212> TYPE: PRT
<213> ORGANISM: Artificial Sequence
<220> FEATURE:
<223> OTHER INFORMATION: Linker

<400> SEQUENCE: 19

Lys Leu Ser Gly Ser Ala Ser Ala Pro Lys Leu Glu Glu Gly Glu Phe
1               5                   10                  15

Ser Glu Ala Arg Val
            20

<210> SEQ ID NO 20
<211> LENGTH: 735
<212> TYPE: DNA
<213> ORGANISM: Homo sapiens

<400> SEQUENCE: 20
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaggcctt     300
ctatggaact actggggcca gggaaccctg gtcaccgtct cctcaaagct ttcagggagt     360
gcatccgccc caaaacttga agaaggtgaa ttttcagaag cacgcgtaga aattgtaatg     420
acacagtctc cagccaccct gtctgtgtct caggggaaa  gagccaccct ctcctgcagg     480
gccagtcaga gtgttagcag caacttagcc tggtaccagc agaaacctgg ccaggctccc     540
aggctcatca tctatggtgc atccaccacg gcctctggta tcccagccag gttcagtgcc     600
agtgggtctg ggacagactt cactctcacc atcagcagcc tgcagtctga gattttgca      660
gtttattact gtcagcagta taataactgg cctccggcgt acacttttgg ccaggggacc     720
aagctggaga tcaaa                                                      735

<210> SEQ ID NO 21
<211> LENGTH: 245
<212> TYPE: PRT
<213> ORGANISM: Homo sapiens

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Leu Leu Trp Asn Tyr Trp Gly Gln Gly Thr Leu Val Thr
            100                 105                 110

Val Ser Ser Lys Leu Ser Gly Ser Ala Ser Ala Pro Lys Leu Glu Glu
        115                 120                 125

Gly Glu Phe Ser Glu Ala Arg Val Glu Ile Val Met Thr Gln Ser Pro
    130                 135                 140

Ala Thr Leu Ser Val Ser Pro Gly Glu Arg Ala Thr Leu Ser Cys Arg
145                 150                 155                 160

Ala Ser Gln Ser Val Ser Ser Asn Leu Ala Trp Tyr Gln Gln Lys Pro
                165                 170                 175

Gly Gln Ala Pro Arg Leu Ile Ile Tyr Gly Ala Ser Thr Thr Ala Ser
            180                 185                 190

Gly Ile Pro Ala Arg Phe Ser Ala Ser Gly Ser Gly Thr Asp Phe Thr
        195                 200                 205

Leu Thr Ile Ser Ser Leu Gln Ser Glu Asp Phe Ala Val Tyr Tyr Cys
    210                 215                 220

Gln Gln Tyr Asn Asn Trp Pro Pro Ala Tyr Thr Phe Gly Gln Gly Thr
225                 230                 235                 240

Lys Leu Glu Ile Lys
                245

<210> SEQ ID NO 22
<211> LENGTH: 1335
<212> TYPE: DNA
<213> ORGANISM: Homo sapiens

<400> SEQUENCE: 22
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gccttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaggcctt     300
ctatggaact actggggcca gggaaccctg gtcaccgtct cctcagcctc caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaactcctgg ggggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc agcccccatc gagaaaacca tctccaaagc caaagggcag    1020
ccccgagaac cacaggtgta caccctgccc ccatcccggg atgagctgac caagaaccag    1080
```

-continued

```
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                      1335
```

<210> SEQ ID NO 23
<211> LENGTH: 648
<212> TYPE: DNA
<213> ORGANISM: Homo sapiens

<400> SEQUENCE: 23

```
gaaattgtaa tgacacagtc tccagccacc ctgtctgtgt ctccagggga aagagccacc     60
ctctcctgca gggccagtca gagtgttagc agcaacttag cctggtacca gcagaaacct    120
ggccaggctc ccaggctcat catctatggt gcatccacca cggcctctgg tatcccagcc    180
aggttcagtg ccagtgggtc tgggacagac ttcactctca ccatcagcag cctgcagtct    240
gaagattttg cagtttatta ctgtcagcag tataataact ggcctccggc gtacactttt    300
ggccagggga ccaagctgga gatcaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt                  648
```

<210> SEQ ID NO 24
<211> LENGTH: 445
<212> TYPE: PRT
<213> ORGANISM: Homo sapiens

<400> SEQUENCE: 24

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Leu Trp Asn Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 25
<211> LENGTH: 216
<212> TYPE: PRT
<213> ORGANISM: Homo sapiens

<400> SEQUENCE: 25

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Ile Ile
        35                  40                  45

Tyr Gly Ala Ser Thr Thr Ala Ser Gly Ile Pro Ala Arg Phe Ser Ala
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Ala Tyr Thr Phe Gly Gln Gly Thr Lys Leu Glu Ile Lys Arg Thr Val
            100                 105                 110
```

```
Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
    195                 200                 205

Lys Ser Phe Asn Arg Gly Glu Cys
    210                 215

<210> SEQ ID NO 26
<211> LENGTH: 327
<212> TYPE: PRT
<213> ORGANISM: Homo sapiens

<400> SEQUENCE: 26

Gly Ala Ala Ala Cys Gly Ala Cys Ala Cys Ala Cys Gly Cys
1               5                   10                  15

Ala Gly Thr Cys Thr Cys Cys Ala Gly Cys Ala Cys Cys Thr
                20                  25                  30

Gly Thr Cys Thr Gly Thr Gly Cys Thr Cys Ala Gly Gly Gly
            35                  40                  45

Gly Ala Ala Gly Ala Gly Cys Cys Ala Cys Cys Thr Cys Thr
50                  55                  60

Cys Cys Thr Gly Cys Ala Gly Gly Cys Cys Ala Gly Thr Cys Ala
65                  70                  75                  80

Gly Ala Gly Thr Gly Thr Thr Ala Gly Cys Ala Gly Cys Ala Ala Cys
            85                  90                  95

Thr Thr Ala Gly Cys Cys Thr Gly Gly Thr Ala Cys Cys Ala Gly Cys
                100                 105                 110

Ala Gly Ala Ala Ala Cys Cys Thr Gly Gly Cys Cys Ala Gly Gly Cys
            115                 120                 125

Thr Cys Cys Cys Ala Gly Gly Cys Thr Cys Cys Thr Cys Ala Thr Cys
130                 135                 140

Thr Ala Thr Gly Gly Thr Gly Cys Ala Thr Cys Cys Ala Cys Cys Ala
145                 150                 155                 160

Gly Gly Gly Cys Cys Ala Cys Thr Gly Thr Ala Thr Cys Cys
                165                 170                 175

Ala Gly Cys Cys Ala Gly Gly Thr Thr Cys Ala Gly Thr Gly Gly Cys
            180                 185                 190

Ala Gly Thr Gly Gly Gly Thr Cys Thr Gly Gly Ala Cys Ala Gly
                195                 200                 205

Ala Gly Thr Thr Cys Ala Cys Thr Cys Thr Cys Ala Cys Cys Ala Thr
    210                 215                 220

Cys Ala Gly Cys Ala Gly Cys Cys Thr Gly Cys Ala Gly Thr Cys Thr
225                 230                 235                 240

Gly Ala Ala Gly Ala Thr Thr Thr Thr Gly Cys Ala Gly Thr Thr
        245                 250                 255

Ala Thr Thr Ala Cys Thr Gly Thr Cys Ala Gly Cys Ala Gly Thr Ala
                260                 265                 270
```

```
Thr Ala Ala Thr Ala Ala Cys Thr Gly Gly Cys Cys Thr Cys Cys Gly
        275                 280                 285

Gly Gly Gly Thr Thr Cys Ala Cys Thr Thr Cys Gly Gly Cys Cys
        290                 295                 300

Cys Thr Gly Gly Gly Ala Cys Cys Ala Ala Gly Thr Gly Gly Ala
305                 310                 315                 320

Thr Ala Thr Cys Ala Ala Ala
            325

<210> SEQ ID NO 27
<211> LENGTH: 109
<212> TYPE: PRT
<213> ORGANISM: Homo sapiens

<400> SEQUENCE: 27

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Gly Phe Thr Phe Gly Pro Gly Thr Lys Val Asp Ile Lys
            100                 105

<210> SEQ ID NO 28
<211> LENGTH: 11
<212> TYPE: PRT
<213> ORGANISM: Homo sapiens

<400> SEQUENCE: 28

Arg Ala Ser Gln Ser Val Ser Ser Asn Leu Ala
1               5                   10

<210> SEQ ID NO 29
<211> LENGTH: 7
<212> TYPE: PRT
<213> ORGANISM: Homo sapiens

<400> SEQUENCE: 29

Gly Ala Ser Thr Arg Ala Thr
1               5

<210> SEQ ID NO 30
<211> LENGTH: 11
<212> TYPE: PRT
<213> ORGANISM: Homo sapiens

<400> SEQUENCE: 30

Gln Gln Tyr Asn Asn Trp Pro Pro Gly Phe Thr
1               5                   10

<210> SEQ ID NO 31
<211> LENGTH: 23
<212> TYPE: PRT
<213> ORGANISM: Homo sapiens
```

<400> SEQUENCE: 31

Glu Thr Thr Leu Thr Gln Ser Pro Ala Thr Leu Ser Val Ser Pro Gly
1               5                   10                  15
Glu Arg Ala Thr Leu Ser Cys
            20

<210> SEQ ID NO 32
<211> LENGTH: 15
<212> TYPE: PRT
<213> ORGANISM: Homo sapiens

<400> SEQUENCE: 32

Trp Tyr Gln Gln Lys Pro Gly Gln Ala Pro Arg Leu Leu Ile Tyr
1               5                   10                  15

<210> SEQ ID NO 33
<211> LENGTH: 32
<212> TYPE: PRT
<213> ORGANISM: Homo sapiens

<400> SEQUENCE: 33

Gly Ile Pro Ala Arg Phe Ser Gly Ser Gly Ser Gly Thr Glu Phe Thr
1               5                   10                  15
Leu Thr Ile Ser Ser Leu Gln Ser Glu Asp Phe Ala Val Tyr Tyr Cys
            20                  25                  30

<210> SEQ ID NO 34
<211> LENGTH: 10
<212> TYPE: PRT
<213> ORGANISM: Homo sapiens

<400> SEQUENCE: 34

Phe Gly Pro Gly Thr Lys Val Asp Ile Lys
1               5                   10

<210> SEQ ID NO 35
<211> LENGTH: 735
<212> TYPE: DNA
<213> ORGANISM: Homo sapiens

<400> SEQUENCE: 35
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatccta tctttggtac agcaaactac       180
gcacagaagt tccagggcag agtcacgatt accgcggacg aatccacgag cacagcctac     240
atggagctga gcagcctgag atctgaggac acggccgtgt attactgtgc gagaggcctt     300
ctatggaact actggggcca gggaaccctg gtcaccgtct cctcaaagct ttcagggagt     360
gcatccgccc caaaacttga agaaggtgaa ttttcagaag cacgcgtaga aacgacactc     420
acgcagtctc cagccaccct gtctgtgtct cagggggaaa gagccaccct ctcctgcagg     480
gccagtcaga gtgttagcag caacttagcc tggtaccagc agaaacctgg ccaggctccc     540
aggctcctca tctatggtgc atccaccagg gccactggta tcccagccag gttcagtggc     600
agtgggtctg ggacagagtt cactctcacc atcagcagcc tgcagtctga agattttgca     660
gtttattact gtcagcagta taataactgg cctccggggt tcactttcgg ccctgggacc     720
aaagtggata tcaaa                                                     735

```
<210> SEQ ID NO 36
<211> LENGTH: 245
<212> TYPE: PRT
<213> ORGANISM: Homo sapiens

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Leu Trp Asn Tyr Trp Gly Gln Gly Thr Leu Val Thr
            100                 105                 110

Val Ser Ser Lys Leu Ser Gly Ser Ala Ser Ala Pro Lys Leu Glu Glu
        115                 120                 125

Gly Glu Phe Ser Glu Ala Arg Val Glu Thr Thr Leu Thr Gln Ser Pro
    130                 135                 140

Ala Thr Leu Ser Val Ser Pro Gly Glu Arg Ala Thr Leu Ser Cys Arg
145                 150                 155                 160

Ala Ser Gln Ser Val Ser Ser Asn Leu Ala Trp Tyr Gln Gln Lys Pro
                165                 170                 175

Gly Gln Ala Pro Arg Leu Leu Ile Tyr Gly Ala Ser Thr Arg Ala Thr
            180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln Gln Tyr Asn Asn Trp Pro Pro Gly Phe Thr Phe Gly Pro Gly Thr
225                 230                 235                 240

Lys Val Asp Ile Lys
                245

<210> SEQ ID NO 37
<211> LENGTH: 7
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (7)..(7)
<223> OTHER INFORMATION: Xaa can be any amino acid

<400> SEQUENCE: 37

Gly Ala Ser Thr Xaa Ala Xaa
1               5

<210> SEQ ID NO 38
<211> LENGTH: 7
<212> TYPE: PRT
```

```
<213> ORGANISM: Artificial sequence
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: Xaa can be Arg or Thr
<220> FEATURE:
<221> NAME/KEY: misc_feature
<222> LOCATION: (7)..(7)
<223> OTHER INFORMATION: Xaa can be Thr or Ser

<400> SEQUENCE: 38

Gly Ala Ser Thr Xaa Ala Xaa
1               5

<210> SEQ ID NO 39
<211> LENGTH: 327
<212> TYPE: DNA
<213> ORGANISM: Homo sapiens

<400> SEQUENCE: 39
gaaacgacac tcacgcagtc tccagccacc ctgtctttgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcac tataatgact ggcctcccac gtggacgttc   300
ggccaaggga ccaagctgga gatcaaa                                      327

<210> SEQ ID NO 40
<211> LENGTH: 109
<212> TYPE: PRT
<213> ORGANISM: Homo sapiens

<400> SEQUENCE: 40

Glu Thr Thr Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Asn Asp Trp Pro Pro
                85                  90                  95

Thr Trp Thr Phe Gly Gln Gly Thr Lys Leu Glu Ile Lys
            100                 105

<210> SEQ ID NO 41
<211> LENGTH: 11
<212> TYPE: PRT
<213> ORGANISM: Homo sapiens

<400> SEQUENCE: 41

Arg Ala Ser Gln Ser Val Ser Ser Asn Leu Ala
1               5                   10

<210> SEQ ID NO 42
<211> LENGTH: 7
```

```
<212> TYPE: PRT
<213> ORGANISM: Homo sapiens

<400> SEQUENCE: 42

Gly Ala Ser Thr Arg Ala Thr
1               5

<210> SEQ ID NO 43
<211> LENGTH: 11
<212> TYPE: PRT
<213> ORGANISM: Homo sapiens

<400> SEQUENCE: 43

Gln His Tyr Asn Asp Trp Pro Pro Thr Trp Thr
1               5                   10

<210> SEQ ID NO 44
<211> LENGTH: 23
<212> TYPE: PRT
<213> ORGANISM: Homo sapiens

<400> SEQUENCE: 44

Glu Thr Thr Leu Thr Gln Ser Pro Ala Thr Leu Ser Leu Ser Pro Gly
1               5                   10                  15

Glu Arg Ala Thr Leu Ser Cys
            20

<210> SEQ ID NO 45
<211> LENGTH: 15
<212> TYPE: PRT
<213> ORGANISM: Homo sapiens

<400> SEQUENCE: 45

Trp Tyr Gln Gln Lys Pro Gly Gln Ala Pro Arg Leu Leu Ile Tyr
1               5                   10                  15

<210> SEQ ID NO 46
<211> LENGTH: 32
<212> TYPE: PRT
<213> ORGANISM: Homo sapiens

<400> SEQUENCE: 46

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 47
<211> LENGTH: 10
<212> TYPE: PRT
<213> ORGANISM: Homo sapiens

<400> SEQUENCE: 47

Phe Gly Gln Gly Thr Lys Leu Glu Ile Lys
1               5                   10

<210> SEQ ID NO 48
<211> LENGTH: 735
<212> TYPE: DNA
<213> ORGANISM: Homo sapiens

<400> SEQUENCE: 48
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
```

```
cctggacaag ggcttgagtg gatgggaggg atcatccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaggcctt    300
ctatggaact actggggcca gggaaccctg gtcaccgtct cctcaaagct tcagggagt     360 gcatccgccc caaaacttga agaaggtgaa ttttcagaag cacgcgtaga acgacactc     420 acgcagtctc cagccaccct gtctttgtct ccaggggaaa gagccaccct ctcctgcagg    480
gccagtcaga gtgttagcag caacttagcc tggtaccagc agaaacctgg ccaggctccc    540
aggctcctca tctatggtgc atccaccagg gccactggta tcccagccag gttcagtggc    600
agtgggtctg ggacagagtt cactctcacc atcagcagcc tgcagtctga agattttgca    660
gtttattact gtcagcacta taatgactgg cctcccacgt ggacgttcgg ccaagggacc    720
aagctggaga tcaaa                                                     735
```

```
<210> SEQ ID NO 49
<211> LENGTH: 245
<212> TYPE: PRT
<213> ORGANISM: Homo sapiens

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Leu Trp Asn Tyr Trp Gly Gln Gly Thr Leu Val Thr
            100                 105                 110

Val Ser Ser Lys Leu Ser Gly Ser Ala Ser Ala Pro Lys Leu Glu Glu
        115                 120                 125

Gly Glu Phe Ser Glu Ala Arg Val Glu Thr Thr Leu Thr Gln Ser Pro
    130                 135                 140

Ala Thr Leu Ser Leu Ser Pro Gly Glu Arg Ala Thr Leu Ser Cys Arg
145                 150                 155                 160

Ala Ser Gln Ser Val Ser Ser Asn Leu Ala Trp Tyr Gln Gln Lys Pro
                165                 170                 175

Gly Gln Ala Pro Arg Leu Leu Ile Tyr Gly Ala Ser Thr Arg Ala Thr
            180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln His Tyr Asn Asp Trp Pro Pro Thr Trp Thr Phe Gly Gln Gly Thr
225                 230                 235                 240

Lys Leu Glu Ile Lys
                245
```

<210> SEQ ID NO 50
<211> LENGTH: 648
<212> TYPE: DNA
<213> ORGANISM: Homo sapiens

<400> SEQUENCE: 50

```
gaaacgacac tcacgcagtc tccagccacc ctgtctttgt ctccagggga aagagccacc      60
ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcac tataatgact ggcctcccac gtggacgttc     300
ggccaaggga ccaagctgga gatcaaacga actgtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata acgccctcca atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaacaggg gagagtgt                  648
```

<210> SEQ ID NO 51
<211> LENGTH: 216
<212> TYPE: PRT
<213> ORGANISM: Homo sapiens

<400> SEQUENCE: 51

```
Glu Thr Thr Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Asn Asp Trp Pro Pro
                85                  90                  95

Thr Trp Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 52
<211> LENGTH: 327
<212> TYPE: DNA
<213> ORGANISM: Homo sapiens

<400> SEQUENCE: 52
gatattgtga tgactcagac tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcctccgtc gtggacgttc   300
ggccaaggga ccaaggtgga gatcaaa                                       327

<210> SEQ ID NO 53
<211> LENGTH: 109
<212> TYPE: PRT
<213> ORGANISM: Homo sapiens

<400> SEQUENCE: 53

Asp Ile Val Met Thr Gln Thr Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Ser Trp Thr Phe Gly Gln Gly Thr Lys Val Glu Ile Lys
            100                 105

<210> SEQ ID NO 54
<211> LENGTH: 11
<212> TYPE: PRT
<213> ORGANISM: Homo sapiens

<400> SEQUENCE: 54

Arg Ala Ser Gln Ser Val Ser Ser Asn Leu Ala
1               5                   10

<210> SEQ ID NO 55
<211> LENGTH: 7
<212> TYPE: PRT
<213> ORGANISM: Homo sapiens

<400> SEQUENCE: 55

Gly Ala Ser Thr Arg Ala Thr
1               5

<210> SEQ ID NO 56
<211> LENGTH: 11
<212> TYPE: PRT
<213> ORGANISM: Homo sapiens

<400> SEQUENCE: 56

Gln Gln Tyr Asn Asn Trp Pro Pro Ser Trp Thr
1               5                   10

<210> SEQ ID NO 57
<211> LENGTH: 23
<212> TYPE: PRT
<213> ORGANISM: Homo sapiens

<400> SEQUENCE: 57

Asp Ile Val Met Thr Gln Thr Pro Ala Thr Leu Ser Val Ser Pro Gly
1               5                   10                  15

Glu Arg Ala Thr Leu Ser Cys
            20

<210> SEQ ID NO 58
<211> LENGTH: 15
<212> TYPE: PRT
<213> ORGANISM: Homo sapiens

<400> SEQUENCE: 58

Trp Tyr Gln Gln Lys Pro Gly Gln Ala Pro Arg Leu Leu Ile Tyr
1               5                   10                  15

<210> SEQ ID NO 59
<211> LENGTH: 32
<212> TYPE: PRT
<213> ORGANISM: Homo sapiens

<400> SEQUENCE: 59

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 60
<211> LENGTH: 10
<212> TYPE: PRT
<213> ORGANISM: Homo sapiens

<400> SEQUENCE: 60

Phe Gly Gln Gly Thr Lys Val Glu Ile Lys
1               5                   10

<210> SEQ ID NO 61
<211> LENGTH: 735
<212> TYPE: DNA
<213> ORGANISM: Homo sapiens

<400> SEQUENCE: 61
caggtccagc tggtgcagtc tggggctgag gtgaagaagc ctgggtcctc ggtgaaggtc        60
tcctgcaagg cttctggagg caccttcagc agctatgcta tcagctgggt gcgacaggcc       120
cctggacaag gcttgagtg gatgggaggg atcatcccta tctttggtac agcaaactac        180
gcacagaagt tccagggcag agtcacgatt accgcggacg aatccacgag cacagcctac       240
atggagctga gcagcctgag atctgaggac acggccgtgt attactgtgc gagaggcctt       300
ctatggaact actggggcca gggaaccctg gtcaccgtct cctcaaagct tcagggagt        360 gcatccgccc caaaacttga gaaggtgaa ttttcagaag cacgcgtaga tattgtgatg        420
actcagactc agccaccctt gtctgtgtct ccaggggaaa gagccaccct ctcctgcagg       480
gccagtcaga gtgttagcag caacttagcc tggtaccagc agaaacctgg ccaggctccc       540
aggctcctca tctatggtgc atccaccagg gccactggta tcccagccag gttcagtggc       600
agtgggtctg ggacagagtt cactctcacc atcagcagcc tgcagtctga agattttgca       660

```
gtttattact gtcagcagta taataactgg cctccgtcgt ggacgttcgg ccaagggacc    720
aaggtggaga tcaaa                                                    735
```

<210> SEQ ID NO 62
<211> LENGTH: 245
<212> TYPE: PRT
<213> ORGANISM: Homo sapiens

<400> SEQUENCE: 62

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Leu Trp Asn Tyr Trp Gly Gln Gly Thr Leu Val Thr
            100                 105                 110

Val Ser Ser Lys Leu Ser Gly Ser Ala Ser Ala Pro Lys Leu Glu Glu
        115                 120                 125

Gly Glu Phe Ser Glu Ala Arg Val Asp Ile Val Met Thr Gln Thr Pro
    130                 135                 140

Ala Thr Leu Ser Val Ser Pro Gly Glu Arg Ala Thr Leu Ser Cys Arg
145                 150                 155                 160

Ala Ser Gln Ser Val Ser Ser Asn Leu Ala Trp Tyr Gln Gln Lys Pro
                165                 170                 175

Gly Gln Ala Pro Arg Leu Leu Ile Tyr Gly Ala Ser Thr Arg Ala Thr
            180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln Gln Tyr Asn Asn Trp Pro Pro Ser Trp Thr Phe Gly Gln Gly Thr
225                 230                 235                 240

Lys Val Glu Ile Lys
                245
```

<210> SEQ ID NO 63
<211> LENGTH: 648
<212> TYPE: DNA
<213> ORGANISM: Homo sapiens

<400> SEQUENCE: 63

```
gatattgtga tgactcagac tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcctccgtc gtggacgttc   300
ggccaaggga ccaaggtgga aatcaaacga actgtggctg caccatctgt cttcatcttc   360
```

```
ccgccatctg atgagcagtt gaaatctgga actgcctctg ttgtgtgcct gctgaataac    420
ttctatccca gagaggccaa agtacagtgg aaggtggata cgccctcca atcgggtaac    480 tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt               648
```

<210> SEQ ID NO 64
<211> LENGTH: 216
<212> TYPE: PRT
<213> ORGANISM: Homo sapiens

<400> SEQUENCE: 64

```
Asp Ile Val Met Thr Gln Thr Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Ser Trp Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 65
<211> LENGTH: 327
<212> TYPE: DNA
<213> ORGANISM: Homo sapiens

<400> SEQUENCE: 65

```
gaaacgacac tcacgcagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataataact ggcctccgat gtacactttt    300
ggccagggga ccaaggtgga gatcaaa                                        327
```

<210> SEQ ID NO 66
<211> LENGTH: 109
<212> TYPE: PRT
<213> ORGANISM: Homo sapiens

<400> SEQUENCE: 66

Glu Thr Thr Leu Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Asn Trp Pro Pro
                85                  90                  95
Met Tyr Thr Phe Gly Gln Gly Thr Lys Val Glu Ile Lys
            100                 105

<210> SEQ ID NO 67
<211> LENGTH: 11
<212> TYPE: PRT
<213> ORGANISM: Homo sapiens

<400> SEQUENCE: 67

Arg Ala Ser Gln Ser Val Ser Ser Asn Leu Ala
1               5                   10

<210> SEQ ID NO 68
<211> LENGTH: 7
<212> TYPE: PRT
<213> ORGANISM: Homo sapiens

<400> SEQUENCE: 68

Gly Ala Ser Thr Arg Ala Thr
1               5

<210> SEQ ID NO 69
<211> LENGTH: 11
<212> TYPE: PRT
<213> ORGANISM: Homo sapiens

<400> SEQUENCE: 69

Gln Gln Tyr Asn Asn Trp Pro Pro Met Tyr Thr
1               5                   10

<210> SEQ ID NO 70
<211> LENGTH: 23
<212> TYPE: PRT
<213> ORGANISM: Homo sapiens

<400> SEQUENCE: 70

Glu Thr Thr Leu Thr Gln Ser Pro Ala Thr Leu Ser Val Ser Pro Gly
1               5                   10                  15
Glu Arg Ala Thr Leu Ser Cys
            20

<210> SEQ ID NO 71
<211> LENGTH: 15

```
<212> TYPE: PRT
<213> ORGANISM: Homo sapiens

<400> SEQUENCE: 71

Trp Tyr Gln Gln Lys Pro Gly Gln Ala Pro Arg Leu Leu Ile Tyr
1               5                   10                  15

<210> SEQ ID NO 72
<211> LENGTH: 32
<212> TYPE: PRT
<213> ORGANISM: Homo sapiens

<400> SEQUENCE: 72

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 73
<211> LENGTH: 10
<212> TYPE: PRT
<213> ORGANISM: Homo sapiens

<400> SEQUENCE: 73

Phe Gly Gln Gly Thr Lys Val Glu Ile Lys
1               5                   10

<210> SEQ ID NO 74
<211> LENGTH: 735
<212> TYPE: DNA
<213> ORGANISM: Homo sapiens

<400> SEQUENCE: 74
caggtccagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaggg atcatcccta tctttggtac agcaaactac   180
gcacagaagt tccagggcag agtcacgatt accgcggacg aatccacgag cacagcctac   240
atggagctga gcagcctgag atctgaggac acggccgtgt attactgtgc gagaggcctt   300
ctatggaact actggggcca gggaaccctg gtcaccgtct cctcaaagct ttcagggagt   360
gcatccgccc caaaacttga gaaggtgaa ttttcagaag cacgcgtaga aacgacactc    420
acgcagtctc cagccaccct gtctgtgtct caggggaaa gagccaccct ctcctgcagg    480
gccagtcaga gtgttagcag caacttagcc tggtaccagc agaaacctgg ccaggctccc   540
aggctcctca tctatggtgc atccaccagg gccactggta tcccagccag gttcagtggc   600
agtgggtctg ggacagagtt cactctcacc atcagcagcc tgcagtctga agattttgca   660
gtttattact gtcagcagta taataactgg cctccgatgt acacttttgg ccaggggacc   720
aaggtggaga tcaaa                                                    735

<210> SEQ ID NO 75
<211> LENGTH: 245
<212> TYPE: PRT
<213> ORGANISM: Homo sapiens

<400> SEQUENCE: 75

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Leu Leu Trp Asn Tyr Trp Gly Gln Gly Thr Leu Val Thr
            100                 105                 110

Val Ser Ser Lys Leu Ser Gly Ser Ala Ser Ala Pro Lys Leu Glu Glu
        115                 120                 125

Gly Glu Phe Ser Glu Ala Arg Val Glu Thr Thr Leu Thr Gln Ser Pro
    130                 135                 140

Ala Thr Leu Ser Val Ser Pro Gly Glu Arg Ala Thr Leu Ser Cys Arg
145                 150                 155                 160

Ala Ser Gln Ser Val Ser Ser Asn Leu Ala Trp Tyr Gln Gln Lys Pro
                165                 170                 175

Gly Gln Ala Pro Arg Leu Leu Ile Tyr Gly Ala Ser Thr Arg Ala Thr
            180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln Gln Tyr Asn Asn Trp Pro Pro Met Tyr Thr Phe Gly Gln Gly Thr
225                 230                 235                 240

Lys Val Glu Ile Lys
            245

<210> SEQ ID NO 76
<211> LENGTH: 648
<212> TYPE: DNA
<213> ORGANISM: Homo sapiens

<400> SEQUENCE: 76
gaaacgacac tcacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcctccgat gtacactttt   300
ggccagggga ccaaggtgga aatcaaacga actgtggctg caccatctgt cttcatcttc   360
ccgccatctg atgagcagtt gaaatctgga actgcctctg ttgtgtgcct gctgaataac   420
ttctatccca gagaggccaa agtacagtgg aaggtggata cgccctccaa atcgggtaac   480
tcccaggaga gtgtcacaga gcaggacagc aaggacagca cctacagcct cagcagcacc   540
ctgacgctga gcaaagcaga ctacgagaaa cacaaagtct acgcctgcga agtcacccat   600
cagggcctga gctcgcccgt cacaaagagc ttcaacaggg gagagtgt              648

<210> SEQ ID NO 77
<211> LENGTH: 216
<212> TYPE: PRT
<213> ORGANISM: Homo sapiens

<400> SEQUENCE: 77

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Met Tyr Thr Phe Gly Gln Gly Thr Lys Val Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
            195                 200                 205

Lys Ser Phe Asn Arg Gly Glu Cys
            210                 215

<210> SEQ ID NO 78
<211> LENGTH: 327
<212> TYPE: DNA
<213> ORGANISM: Homo sapiens

<400> SEQUENCE: 78
gaaacgacac tcacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagaag tataataact ggcctccggc cttcactttc   300
ggccctggga ccaaagtgga tatcaaa                                       327

<210> SEQ ID NO 79
<211> LENGTH: 109
<212> TYPE: PRT
<213> ORGANISM: Homo sapiens

<400> SEQUENCE: 79

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

```
                Tyr Gly Ala Ser Thr Arg Ala Thr Gly Ile Pro Ala Arg Phe Ser Gly
                 50                  55                  60

Ser Gly Ser Gly Thr Glu Phe Thr Leu Thr Ile Ser Ser Leu Gln Ser
                 65                  70                  75                  80

Glu Asp Phe Ala Val Tyr Tyr Cys Gln Lys Tyr Asn Asn Trp Pro Pro
                                 85                  90                  95

Ala Phe Thr Phe Gly Pro Gly Thr Lys Val Asp Ile Lys
                                100                 105
```

<210> SEQ ID NO 80
<211> LENGTH: 11
<212> TYPE: PRT
<213> ORGANISM: Homo sapiens

<400> SEQUENCE: 80

```
Arg Ala Ser Gln Ser Val Ser Asn Leu Ala
  1               5                  10
```

<210> SEQ ID NO 81
<211> LENGTH: 7
<212> TYPE: PRT
<213> ORGANISM: Homo sapiens

<400> SEQUENCE: 81

```
Gly Ala Ser Thr Arg Ala Thr
  1               5
```

<210> SEQ ID NO 82
<211> LENGTH: 11
<212> TYPE: PRT
<213> ORGANISM: Homo sapiens

<400> SEQUENCE: 82

```
Gln Lys Tyr Asn Asn Trp Pro Pro Ala Phe Thr
  1               5                  10
```

<210> SEQ ID NO 83
<211> LENGTH: 23
<212> TYPE: PRT
<213> ORGANISM: Homo sapiens

<400> SEQUENCE: 83

```
Glu Thr Thr Leu Thr Gln Ser Pro Ala Thr Leu Ser Val Ser Pro Gly
  1               5                  10                  15

Glu Arg Ala Thr Leu Ser Cys
                 20
```

<210> SEQ ID NO 84
<211> LENGTH: 15
<212> TYPE: PRT
<213> ORGANISM: Homo sapiens

<400> SEQUENCE: 84

```
Trp Tyr Gln Gln Lys Pro Gly Gln Ala Pro Arg Leu Leu Ile Tyr
  1               5                  10                  15
```

<210> SEQ ID NO 85
<211> LENGTH: 32
<212> TYPE: PRT
<213> ORGANISM: Homo sapiens

<400> SEQUENCE: 85

```
Gly Ile Pro Ala Arg Phe Ser Gly Ser Gly Ser Gly Thr Glu Phe Thr
  1               5                  10                  15
```

Leu Thr Ile Ser Ser Leu Gln Ser Glu Asp Phe Ala Val Tyr Tyr Cys
            20                  25                  30

<210> SEQ ID NO 86
<211> LENGTH: 10
<212> TYPE: PRT
<213> ORGANISM: Homo sapiens

<400> SEQUENCE: 86

Phe Gly Pro Gly Thr Lys Val Asp Ile Lys
1               5                   10

<210> SEQ ID NO 87
<211> LENGTH: 735
<212> TYPE: DNA
<213> ORGANISM: Homo sapiens

<400> SEQUENCE: 87
caggtccagc tggtgcagtc tggggctgag gtgaagaagc tggggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaggcctt     300
ctatggaact actggggcca gggaaccctg gtcaccgtct cctcaaagct tcagggagt      360 gcatccgccc caaaacttga gaaggtgaa ttttcagaag cacgcgtaga acgacactc       420 acgcagtctc cagccaccct gtctgtgtct ccaggggaaa gagccaccct ctcctgcagg     480
gccagtcaga gtgttagcag caacttagcc tggtaccagc agaaacctgg ccaggctccc     540
aggctcctca tctatggtgc atccaccagg gccactggta tcccagccag gttcagtggc     600
agtgggtctg ggacagagtt cactctcacc atcagcagcc tgcagtctga agattttgca     660
gtttattact gtcagaagta taataactgg cctccggcct tcactttcgg ccctgggacc     720
aaagtggata tcaaa                                                      735

<210> SEQ ID NO 88
<211> LENGTH: 245
<212> TYPE: PRT
<213> ORGANISM: Homo sapiens

<400> SEQUENCE: 88

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Leu Trp Asn Tyr Trp Gly Gln Gly Thr Leu Val Thr
            100                 105                 110

Val Ser Ser Lys Leu Ser Gly Ser Ala Ser Ala Pro Lys Leu Glu Glu
        115                 120                 125

```
Gly Glu Phe Ser Glu Ala Arg Val Glu Thr Thr Leu Thr Gln Ser Pro
        130                 135                 140

Ala Thr Leu Ser Val Ser Pro Gly Glu Arg Ala Thr Leu Ser Cys Arg
145                 150                 155                 160

Ala Ser Gln Ser Val Ser Asn Leu Ala Trp Tyr Gln Lys Pro
                165                 170                 175

Gly Gln Ala Pro Arg Leu Leu Ile Tyr Gly Ala Ser Thr Arg Ala Thr
            180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
        210                 215                 220

Gln Lys Tyr Asn Asn Trp Pro Pro Ala Phe Thr Phe Gly Pro Gly Thr
225                 230                 235                 240

Lys Val Asp Ile Lys
                245

<210> SEQ ID NO 89
<211> LENGTH: 11
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (9)..(9)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be any amino acid

<400> SEQUENCE: 89

Gln Xaa Tyr Asn Xaa Trp Pro Pro Xaa Xaa Thr
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be Gln or His or Lys
<220> FEATURE:
<221> NAME/KEY: misc_feature
<222> LOCATION: (5)..(5)
<223> OTHER INFORMATION: Xaa can be Asn or Asp
<220> FEATURE:
<221> NAME/KEY: misc_feature
<222> LOCATION: (9)..(9)
<223> OTHER INFORMATION: Xaa can be Gly or Thr or Ser or Met or Ala
<220> FEATURE:
<221> NAME/KEY: misc_feature
<222> LOCATION: (10)..(10)
<223> OTHER INFORMATION: Xaa can be Phe or Trp or Tyr

<400> SEQUENCE: 90
```

Gln Xaa Tyr Asn Xaa Trp Pro Pro Xaa Xaa Thr
1               5                   10

<210> SEQ ID NO 91
<211> LENGTH: 457
<212> TYPE: PRT
<213> ORGANISM: Artificial Sequence
<220> FEATURE:
<223> OTHER INFORMATION: MT201 IgG Heavy Chain

<400> SEQUENCE: 91

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Met Gly Trp Gly Ser Gly Trp Arg Pro Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu

```
                 355                 360                 365
Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 92
<211> LENGTH: 214
<212> TYPE: PRT
<213> ORGANISM: Artificial Sequence
<220> FEATURE:
<223> OTHER INFORMATION: MT201 IgG Light Chain

<400> SEQUENCE: 92

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 93
<211> LENGTH: 446
<212> TYPE: PRT
<213> ORGANISM: Artificial Sequence
<220> FEATURE:
<223> OTHER INFORMATION: MOC31 IgG Heavy Chain
```

<400> SEQUENCE: 93

```
Gln Val Lys Leu Gln Gln Ser Gly Pro Glu Leu Lys Lys Pro Gly Glu
 1               5                  10                  15
Thr Val Lys Ile Ser Cys Lys Ala Ser Gly Tyr Thr Phe Thr Asn Tyr
            20                  25                  30
Gly Met Asn Trp Val Lys Gln Ala Pro Gly Lys Gly Leu Lys Trp Met
        35                  40                  45
Gly Trp Ile Asn Thr Tyr Thr Gly Glu Ser Thr Tyr Ala Asp Asp Phe
    50                  55                  60
Lys Gly Arg Phe Ala Phe Ser Leu Glu Thr Ser Ala Ser Ala Ala Tyr
65                  70                  75                  80
Leu Gln Ile Asn Asn Leu Lys Asn Glu Asp Thr Ala Thr Tyr Phe Cys
                85                  90                  95
Ala Arg Phe Ala Ile Lys Gly Asp Tyr Trp Gly Gln Gly Thr Thr Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
```

```
Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445

<210> SEQ ID NO 94
<211> LENGTH: 219
<212> TYPE: PRT
<213> ORGANISM: Artificial Sequence
<220> FEATURE:
<223> OTHER INFORMATION: MOC31 IgG Light Chain

<400> SEQUENCE: 94

Asp Ile Val Leu Thr Gln Ser Pro Phe Ser Asn Pro Val Thr Leu Gly
1               5                   10                  15

Thr Ser Ala Ser Ile Ser Cys Arg Ser Thr Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Ile Pro Arg Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 95
<211> LENGTH: 495
<212> TYPE: PRT
<213> ORGANISM: Artificial Sequence
<220> FEATURE:
<223> OTHER INFORMATION: Human EpCAM/Fc fusion

<400> SEQUENCE: 95

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Asn Arg Gln Cys Gln Cys
        35                  40                  45

Thr Ser Val Gly Ala Gln Asn Thr Val Ile Cys Ser Lys Leu Ala Ala
    50                  55                  60
```

```
Lys Cys Leu Val Met Lys Ala Glu Met Asn Gly Ser Lys Leu Gly Arg
 65                  70                  75                  80

Arg Ala Lys Pro Glu Gly Ala Leu Gln Asn Asn Asp Gly Leu Tyr Asp
                 85                  90                  95

Pro Asp Cys Asp Glu Ser Gly Leu Phe Lys Ala Lys Gln Cys Asn Gly
            100                 105                 110

Thr Ser Thr Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Ala Ala Asp Lys Thr His
            260                 265                 270

Thr Cys Pro Pro Cys Pro Ala Pro Glu Leu Leu Gly Gly Pro Ser Val
        275                 280                 285

Phe Leu Phe Pro Pro Lys Pro Lys Asp Thr Leu Met Ile Ser Arg Thr
290                 295                 300

Pro Glu Val Thr Cys Val Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Ala Leu Pro Ala Pro Ile Glu Lys Thr Ile
370                 375                 380

Ser Lys Ala Lys Gly Gln Pro Arg Glu Pro Gln Val Tyr Thr Leu Pro
385                 390                 395                 400

Pro Ser Arg Asp Glu Leu Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Lys Leu Thr Val Asp Lys Ser Arg
450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys
                485                 490                 495
```

<210> SEQ ID NO 96
<211> LENGTH: 496
<212> TYPE: PRT
<213> ORGANISM: Artificial Sequence
<220> FEATURE:
<223> OTHER INFORMATION: Cynomolgus EpCAM/Fc fusion

<400> SEQUENCE: 96

```
Met Ala Pro Pro Gln Val Leu Ala Phe Gly Leu Leu Leu Ala Ala Ala
1               5                   10                  15

Thr Ala Thr Phe Ala Ala Ala Gln Lys Glu Cys Val Cys Glu Asn Tyr
            20                  25                  30

Lys Leu Ala Val Asn Cys Phe Leu Asn Asp Asn Gly Gln Cys Gln Cys
        35                  40                  45

Thr Ser Ile Gly Ala Gln Asn Thr Val Leu Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Thr Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140

Ile Ile Glu Leu Lys His Lys Ala Arg Glu Lys Pro Tyr Asp Val Gln
145                 150                 155                 160

Ser Leu Arg Thr Ala Leu Glu Glu Ala Ile Lys Thr Arg Tyr Gln Leu
                165                 170                 175

Asp Pro Lys Phe Ile Thr Asn Ile Leu Tyr Glu Asp Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
    210                 215                 220

Leu Phe His Ser Lys Lys Met Asp Leu Arg Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Ala Ala Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365
```

```
Lys Cys Lys Val Ser Asn Lys Ala Leu Pro Ala Pro Ile Glu Lys Thr
        370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
                420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
        450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 97
<211> LENGTH: 751
<212> TYPE: DNA
<213> ORGANISM: Artificial Sequence
<220> FEATURE:
<223> OTHER INFORMATION: scFv 3-17I  with restriction sites

<400> SEQUENCE: 97
ccatggccca ggtccagctg gtgcagtctg gggctgaggt gaagaagcct gggtcctcgg      60
tgaaggtctc ctgcaaggct tctggaggca ccttcagcag ctatgctatc agctgggtgc    120
gacaggcccc tggacaaggg cttgagtgga tgggagggat catccctatc tttggtacag    180
caaactacgc acagaagttc cagggcagag tcacgattac cgcggacgaa tccacgagca    240
cagcctacat ggagctgagc agcctgagat ctgaggacac ggccgtgtat tactgtgcga    300
gaggccttct atggaactac tggggccagg gaaccctggt caccgtctcc tcaaagcttt    360
cagggagtgc atccgcccca aaacttgaag aaggtgaatt ttcagaagca cgcgtagaaa    420
ttgtaatgac acagtctcca gccaccctgt ctgtgtctcc aggggaaaga gccaccctct    480
cctgcagggc cagtcagagt gttagcagca acttagcctg gtaccagcag aaacctggcc    540
aggctcccag gctcatcatc tatggtgcat ccaccacggc ctctggtatc ccagccaggt    600
tcagtgccag tgggtctggg acagacttca ctctcaccat cagcagcctg cagtctgaag    660
attttgcagt ttattactgt cagcagtata taactggcc tccggcgtac acttttggcc    720
aggggaccaa gctggagatc aaagcggccg c                                   751
```